United States Patent
Avrameas et al.

(10) Patent No.: US 8,003,595 B2
(45) Date of Patent: Aug. 23, 2011

(54) AMINO ACID SEQUENCES FACILITATING PENETRATION OF A SUBSTANCE OF INTEREST INTO CELLS AND/OR CELL NUCLEI

(75) Inventors: Eustrate Avrameas, Athens (GR); Therese Ternynck, Paris (FR)

(73) Assignee: Cellectis, Romainville (FR)

(*) Notice: Subject to any disclaimer, the term of this patent is extended or adjusted under 35 U.S.C. 154(b) by 1082 days.

(21) Appl. No.: 10/231,889

(22) Filed: Aug. 29, 2002

(65) Prior Publication Data

US 2003/0199677 A1 Oct. 23, 2003

Related U.S. Application Data

(63) Continuation-in-part of application No. PCT/FR00/02621, filed on Mar. 1, 2000, and a continuation-in-part of application No. PCT/FR01/00613, filed on Mar. 1, 2001.

(60) Provisional application No. 60/316,063, filed on Aug. 30, 2001.

(30) Foreign Application Priority Data

Mar. 1, 2000 (FR) ..................................... 00 02621

(51) Int. Cl.
C07K 16/46 (2006.01)
A61K 38/00 (2006.01)
C07G 11/00 (2006.01)
C07G 3/00 (2006.01)

(52) U.S. Cl. ....... 514/1.1; 530/326; 530/391.7; 530/402
(58) Field of Classification Search .................. None
See application file for complete search history.

(56) References Cited

U.S. PATENT DOCUMENTS

| | | | |
|---|---|---|---|
| 3,710,795 A | 1/1973 | Higuchi et al. | |
| 4,526,888 A | 7/1985 | Williams et al. | |
| 5,262,564 A | 11/1993 | Kun et al. | |
| 5,521,291 A | 5/1996 | Curiel et al. | |
| 5,547,929 A | 8/1996 | Anderson et al. | |
| 5,624,894 A | 4/1997 | Bodor | |
| 5,635,383 A | 6/1997 | Wu et al. | |
| 6,043,339 A * | 3/2000 | Lin et al. ....................... | 530/300 |
| 6,066,485 A | 5/2000 | Guthridge et al. | |
| 6,274,712 B1 * | 8/2001 | Springer et al. .............. | 530/399 |
| 6,635,248 B1 | 10/2003 | Ternynck et al. | |
| 6,750,321 B1 * | 6/2004 | Chen et al. .................... | 530/317 |
| 6,855,801 B1 | 2/2005 | San Antonio | |
| 7,049,286 B2 | 5/2006 | Tchelingerian | |
| 7,112,562 B2 | 9/2006 | Tchelingerian | |
| 2003/0153490 A1 * | 8/2003 | Tchelingerian .................. | 514/3 |
| 2003/0199677 A1 | 10/2003 | Avrameas et al. | |
| 2004/0123343 A1 | 6/2004 | La Rosa et al. | |
| 2007/0042492 A1 | 2/2007 | Avrameas | |
| 2007/0259813 A1 | 11/2007 | Arranz | |

FOREIGN PATENT DOCUMENTS

| | | |
|---|---|---|
| FR | 2 766 826 | 2/1999 |
| WO | WO 90/12587 | 11/1990 |
| WO | WO 91/04315 | 4/1991 |
| WO | WO 94/28921 | 12/1994 |
| WO | WO 96/08274 | 3/1996 |
| WO | WO 96/38163 | 12/1996 |
| WO | WO 97/02840 | 1/1997 |
| WO | WO 98/40401 | 9/1998 |
| WO | WO 98/56938 | 12/1998 |
| WO | WO 99/06632 | 2/1999 |
| WO | WO 99/07414 | 2/1999 |
| WO | WO 99/32136 | 7/1999 |
| WO | WO 99/67284 A2 * | 12/1999 |
| WO | WO 00/45831 | 8/2000 |
| WO | WO 0164738 A2 | 9/2001 |
| WO | WO 03/018636 | 3/2003 |
| WO | WO 03/092736 | 11/2003 |
| WO | WO 03/106491 | 12/2003 |
| WO | WO 2004/011033 | 2/2004 |
| WO | WO 2005/016960 | 2/2005 |

OTHER PUBLICATIONS

Ngo et al. The Protein Folding Problem and Tertiary Structure Prediction, Merz and LeGrand, Birkhauser Boston, pp. 491-495, 1995.*
Grieb et al. Biochem. Biophys. Res. Comm. 1998, vol. 246, pp. 182-191.*
Fromm et al. Arch. Biochem. Biophsy. 1997, vol. 343, No. 1, pp. 92-100.*
A_Genseq Accession No. AAW99570. Jun. 22, 1999, 2 pages.*
Ma et al. Biotech. Bioeng. 1992, 40: 530-536.*
Brian R. Stoll et al., "A mechanistic analysis of carrier-mediated oral delivery of protein therapeutics," Journal of Controlled Release, 64 (2000) 217, 218, Elsevier, XP-002241926.
International Search Report dated Sep. 17, 2003 for PCT/IB02/03916.
Written Opinion dated Sep. 22, 2003 for PCT/IB02/03916, first two pages only.
Amara, et al, J. Biol. Chem., vol. 274, p. 23916-23925, 1999.
Arkonac, et al., J. Biol. Chem., vol. 273, p. 4400-4405, 1998.
Avrameas, et al., Proc. Natl. Acad. Sci., vol. 95, p. 5601-5606, 1998.
Campanelli, et al., Development, vol. 122, p. 1663-1672, 1996.
Cardin, et al., Biochem. Biophys. Res. Com., vol. 154, p. 741-745, 1988.
Cardin & Weintraub, Arteriosclerosis, vol. 9, p. 21-32, 1989.
David, FASEB J., vol. 7, p. 1023-1030, 1993.
Fowlkes, et al., Endocrinol., vol: 138, p. 2280-2285, 1997.
GenBank Accession No. 600165A, 1992.
GenBank Accession No. 550085A, 1992.

(Continued)

Primary Examiner — Gerald R Ewoldt
Assistant Examiner — Marianne Dibrino
(74) Attorney, Agent, or Firm — Arent Fox LLP

(57) ABSTRACT

The invention concerns an amino acid sequence capable of facilitating penetration of a substance of interest into cells and/or cell nuclei, characterized in that it is capable of reacting in vivo with aminoglycans. Optionally the sequence is derived from a protein of human origin.

4 Claims, 24 Drawing Sheets

OTHER PUBLICATIONS

GenBank Accession No. AAH05255, Jul. 2001.
GenBank Accession No. AAA59179, 1995.
Xu, et al., Glyconjug J., vol. 13, p. 81-90, 1996.
Hasan, et al., J. Immunol., vol. 162, p. 1064-1070, 1999.
Hirabayashi, et al., Scand. J. Immunol., vol. 37, p. 533-540, 1993.
Inoue, et al., FEBS, vol. 269, p. 89-92, 1990.
Javadpour, et al., J. Med. Chem., vol. 39, p. 3107-3113, 1996.
Kalsi, et al., Lupus, vol. 4, p. 375-389, 1995.
Lortat-Jacob & Grimaud, FEBS, vol. 280, p. 152-154, 1991.
Maher, et al., Mol. Cell. Biol., vol. 9, p. 2251-2253, 1989.
Bernfield, et al., Annu. Rev. Cell. Biol., vol. 8, p. 365-393, 1992.
Pohl, et al., FEBS, vol. 272, p. 200-204, 1990.
Stevenson, et al., J. Autoimmunity, vol. 6, p. 809-825, 1993.
Yayon, et al., Cell, vol. 64, p. 841-848, 1991.
Partial International Search Report for PCT/IB02/03916, mailed Jun. 23, 2003.
PCT Written Opinion for PCT/IB02/03916, 2003.
Avrameas, et al. (1999) Bioconjugate Chemistry 10(1) : 87-93.
Bosanquet (1986) Cancer Chemother. Pharmacol. 18: 176-179.
Caldwell, et al. (1996) Int. J. Biochem. Cell Biol. 28: 203-216.
Castellot, et al. (May 1986) J. Cell Biol. 102: 1979-1984.
Darveau, et al. (1991) Antimicrobial Agents and Chemotherapy 35(6): 1153-1159.
Dini, et al. (1996) Cellular and Molecular Biology 42(2): 269-277.
Esko, et al. (1985) Proc. Natl. Acad. Sci. 82: 3197-3201.
Guevara, et al. (1999) Journal of Protein Chemistry 18(8): 845-857.
Gueritte-Voegelein (1991) J. Med. Chem. 34: 992-998.
Hirsch (1991) New Engl. J. Med. 324: 1565-1574.
Kallunski & Tryggvason (Jan. 1992) The Journal of Cell Biology 116(2): 559-571.
Lookene, et al. (2000) Biochemistry 39: 230-236.
Margalit, et al. (1993) Journal of Biological Chemistry 265(26): 19228-19231.
Mesri, et al. (1994) Journal of Cell Science 107 : 2599-2608.
Morrow J. Biol. Chem. 273(32): 20114-20120, 1998.
Niidome, et al. (1999) Bioconjugate Chemistry 10(5): 773-780.
Nogales (1999) Cell. Mol. Life Sci. 56: 133-142.
Ohta, et al. (Apr. 1994) Free Radical Biology & Medicine 16(4): 501-507.
Olofsson, et al. (1999) Journal of Clinical Investigation 4: 885-894.
Park, et al. (Mar. 6, 1998) Biochem. Biophys. Res. Commun. 244(1): 253-257.
Pasqualini, et al. (1997) Nature Biotech. 15: 542-546.
Robinson (1963) Adv. Lip. Res. 1:1 133-182.
Rostand and Esko (Jan. 1997) Infection and Immunity 65(1): 1-8.
Ruoslahti & Yamazuchi (Mar. 1991) Cell 64: 867-869.
Silber, et al. (Nov. 15, 1994) Blood 84(10): 3440-3446.
Tabosa Do Egito, et al. (Sep. 1996) J. Antimicrob. Chemother. 38(3): 485-497.
Ternynck, et al. (1987) "Techniques immunoenzymatiques" Editions INSERM pp. 29-121.
Travis J. (Oct. 5, 1994) Journal of the National Cancer Institute 86(19): 1450-1457.
Wall and Wani (Feb. 15, 1995) Cancer Research 55: 753-760.
Weisgraber and Rall (1987) Journal of Biological Chemistry 262(23): 11097-11103.
Zunino, et al. (1999) Drug Resistance Updates 2: 351-357.
International Preliminary Examination Report for International Patent Application No. PCT/FR01/00613 mailed Sep. 2, 2006.
International Search Report for International Patent Application No. PCT/IB2004/002936 mailed Feb. 10, 2005.
International Search Report for International Patent Application No. PCT/FR2004/002142 mailed Apr. 26, 2005.
Written Opinion for International Patent Application No. PCT/FR2004/002142 mailed Apr. 26, 2005.
French Search Report for FR 0002621.

* cited by examiner

1 : RIBONUCLEASE A (RNase A)
2 : COUPLING TO PEPTIDE 10 (CYST.-PLH-CDR3 HUMAN)
3 : COUPLING TO PEPTIDE 10 (PLH-CDR3-CYST. HUMAN)

1 AND 2 : COUPLING WITH PEPTIDE 16 (P3CDR3 MOUSE)
3 : COUPLING TO PEPTIDE 5 (PLH-CDR3 MOUSE)
4 : COUPLING TO PEPTIDE 10 (PLH-CDR3 HUMAN)
5 : RIBONUCLEASE A (RNase A)
6 : PEPTIDE 16 (P3CDR3 MOUSE)

=> 24h

B

A

A

B

C

```
SEQUENCE LISTING

<160> NUMBER OF SEQ ID NOS: 57

<210> SEQ ID NO 1
<211> LENGTH: 7
<212> TYPE: PRT
<213> ORGANISM: Homo sapiens

<400> SEQUENCE: 1

Val Lys Arg Gly Leu Lys Leu
1               5

<210> SEQ ID NO 2
<211> LENGTH: 14
<212> TYPE: PRT
<213> ORGANISM: Homo sapiens

<400> SEQUENCE: 2

Val Lys Arg Gly Leu Lys Leu Val Lys Arg Gly Leu Lys Leu
1               5                   10

<210> SEQ ID NO 3
<211> LENGTH: 21
<212> TYPE: PRT
<213> ORGANISM: Homo sapiens

<400> SEQUENCE: 3

Val Lys Arg Gly Leu Lys Leu Val Lys Arg Gly Leu Lys Leu Val Lys
1               5                   10                  15

Arg Gly Leu Lys Leu
            20

<210> SEQ ID NO 4
<211> LENGTH: 11
<212> TYPE: PRT
<213> ORGANISM: Mus musculus x Rattus norvegicus

<400> SEQUENCE: 4

Arg Gln Lys Tyr Asn Lys Arg Ala Met Asp Tyr
1               5                   10

<210> SEQ ID NO 5
<211> LENGTH: 18
<212> TYPE: PRT
<213> ORGANISM: Homo sapiens - Mus musculus - Rattus norvegicus

<400> SEQUENCE: 5
```

Val Lys Arg Gly Leu Lys Leu Arg Gln Lys Tyr Asn Lys Arg Ala Met
1               5                   10                  15

Asp Tyr

<210> SEQ ID NO 6
<211> LENGTH: 20
<212> TYPE: PRT
<213> ORGANISM: Mus musculus x Rattus norvegicus

<400> SEQUENCE: 6

Thr Tyr Tyr Ser Asp Thr Val Lys Gly Arg Phe Thr Arg Gln Lys Tyr
1               5                   10                  15

Asn Lys Arg Ala
            20

<210> SEQ ID NO 7
<211> LENGTH: 26
<212> TYPE: PRT
<213> ORGANISM: Homo sapien - Mus musculus - Rattus norvegicus

<400> SEQUENCE: 7

Val Lys Arg Gly Leu Lys Leu Thr Tyr Tyr Ser Asp Thr Val Lys Gly
1               5                   10                  15

Arg Phe Thr Arg Gln Tyr Asn Lys Arg Ala
            20                  25

<210> SEQ ID NO 8
<211> LENGTH: 17
<212> TYPE: PRT
<213> ORGANISM: Homo sapiens

<400> SEQUENCE: 8

Val Arg Arg Ser Gly Arg Val Val Pro Ala Ala Pro Arg Asn Arg
1               5                   10                  15

Asp

<210> SEQ ID NO 9
<211> LENGTH: 24
<212> TYPE: PRT
<213> ORGANISM: Homo sapiens

<400> SEQUENCE: 9

Val Lys Arg Gly Leu Lys Leu Val Arg Arg Ser Gly Arg Val Val Val
1               5                   10                  15

Pro Ala Ala Pro Arg Asn Arg Asp
            20

<210> SEQ ID NO 10
<211> LENGTH: 19
<212> TYPE: PRT
<213> ORGANISM: Homo sapiens

<400> SEQUENCE: 10

Val Lys Arg Gly Leu Lys Leu Arg His Val Arg Pro Arg Val Thr Arg
1               5                   10                  15

Met Asp Val

<210> SEQ ID NO 11
<211> LENGTH: 19
<212> TYPE: PRT
<213> ORGANISM: Homo sapiens -continued

```
<400> SEQUENCE: 11

Val Lys Arg Gly Leu Lys Leu Gly Tyr Tyr Asp Phe Trp Ser Gly Pro
1               5                   10                  15

Gly Lys Asn

<210> SEQ ID NO 12
<211> LENGTH: 27
<212> TYPE: PRT
<213> ORGANISM: Mus musculus x Rattus norvegicus

<400> SEQUENCE: 12

Asn Val Lys Lys Pro Lys Leu Thr Tyr Tyr Ser Asp Thr Val Lys Gly
1               5                   10                  15

Arg Phe Thr Arg Gln Lys Tyr Asn Lys Arg Ala
            20                  25

<210> SEQ ID NO 13
<211> LENGTH: 31
<212> TYPE: PRT
<213> ORGANISM: Homo sapiens

<400> SEQUENCE: 13

Val Lys Arg Gly Leu Lys Leu Ser Gly Ser Thr Asn Tyr Asn Pro Ser
1               5                   10                  15

Leu Lys Ser Arg His Val Arg Pro Arg Val Thr Arg Met Asp Val
            20                  25                  30

<210> SEQ ID NO 14
<211> LENGTH: 28
<212> TYPE: PRT
<213> ORGANISM: Mus musculus x Rattus norvegicus

<400> SEQUENCE: 14

Arg Gln Lys Tyr Asn Lys Arg Ala Thr Tyr Tyr Ser Asp Thr Val Lys
1               5                   10                  15

Gly Arg Phe Thr Arg Gln Lys Tyr Asn Lys Arg Ala
            20                  25

<210> SEQ ID NO 15
<211> LENGTH: 24
<212> TYPE: PRT
<213> ORGANISM: Homo sapiens

<400> SEQUENCE: 15

Arg Gly Val Arg Pro Arg Val Thr Arg Met Asp Val Arg His Val Arg
1               5                   10                  15

Pro Arg Val Thr Arg Met Asp Val
            20

<210> SEQ ID NO 16
<211> LENGTH: 31
<212> TYPE: PRT
<213> ORGANISM: Homo sapiens

<400> SEQUENCE: 16

Arg His Val Arg Pro Arg Val Thr Arg Met Asp Val Val Lys Arg Gly
1               5                   10                  15

Leu Lys Leu Arg His Val Arg Pro Arg Val Thr Arg Met Asp Val
            20                  25                  30

<210> SEQ ID NO 17
<211> LENGTH: 8
```

```
<212> TYPE: PRT
<213> ORGANISM: Homo sapiens

<400> SEQUENCE: 17

Leu Arg Lys Arg Leu Leu Arg Asp
1               5

<210> SEQ ID NO 18
<211> LENGTH: 4
<212> TYPE: PRT
<213> ORGANISM: Homo sapiens

<400> SEQUENCE: 18

Lys Ser Arg Lys
1

<210> SEQ ID NO 19
<211> LENGTH: 8
<212> TYPE: PRT
<213> ORGANISM: Homo sapiens

<400> SEQUENCE: 19

Lys Ser Arg Lys Lys Ser Arg Lys
1               5

<210> SEQ ID NO 20
<211> LENGTH: 12
<212> TYPE: PRT
<213> ORGANISM: Homo sapiens

<400> SEQUENCE: 20

Arg Lys Gly Phe Tyr Lys Arg Lys Gln Cys Lys Pro
1               5                   10

<210> SEQ ID NO 21
<211> LENGTH: 17
<212> TYPE: PRT
<213> ORGANISM: Homo sapiens

<400> SEQUENCE: 21

Gly Arg Pro Arg Glu Ser Gly Lys Lys Arg Lys Arg Lys Arg Leu Lys
1               5                   10                  15

Pro

<210> SEQ ID NO 22
<211> LENGTH: 32
<212> TYPE: PRT
<213> ORGANISM: Mus musculis x Rattus norvegicus

<400> SEQUENCE: 22

Lys Lys Lys Lys Lys Lys Lys Lys Lys Lys Lys Thr Tyr Tyr Ser
1               5                   10                  15

Asp Thr Val Lys Gly Arg Phe Thr Arg Gln Lys Tyr Asn Lys Arg Ala
            20                  25                  30

<210> SEQ ID NO 23
<211> LENGTH: 30
<212> TYPE: PRT
<213> ORGANISM: Mus musculis x Rattus norvegicus

<400> SEQUENCE: 23

Lys Lys Lys Lys Lys Lys Lys Lys Lys Lys Val Lys Arg Gly
1               5                   10                  15

Leu Lys Leu Arg Gln Lys Tyr Asn Lys Arg Ala Met Asp Tyr
```

20          25          30

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Peptide
      Having Anti-Microbial Activity

<400> SEQUENCE: 24

Lys Leu Ala Lys Leu Ala Lys Lys Leu Ala Lys Leu Ala Lys
1               5                   10

<210> SEQ ID NO 25
<211> LENGTH: 18
<212> TYPE: PRT
<213> ORGANISM: Homo sapiens

<400> SEQUENCE: 25

Arg Lys Gly Lys Phe Tyr Lys Arg Lys Gln Cys Lys Pro Ser Arg Gly
1               5                   10                  15

Arg Lys

<210> SEQ ID NO 26
<211> LENGTH: 18
<212> TYPE: PRT
<213> ORGANISM: Homo sapiens

<400> SEQUENCE: 26

Ser Glu Arg Lys Lys Arg Arg Arg Glu Ser Arg Lys Lys Arg Arg Arg
1               5                   10                  15

Glu Ser

<210> SEQ ID NO 27
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: All amino acids are in configuration D

<400> SEQUENCE: 27

Ser Glu Arg Lys Lys Arg Arg Arg Glu Ser Arg Lys Lys Arg Arg Arg
1               5                   10                  15

Glu Ser

<210> SEQ ID NO 28
<211> LENGTH: 16
<212> TYPE: PRT
<213> ORGANISM: Homo sapiens

<400> SEQUENCE: 28

Arg Lys Lys Arg Arg Arg Gly Asp Arg Lys Lys Arg Arg Arg Gly Asp
1               5                   10                  15

<210> SEQ ID NO 29
<211> LENGTH: 15
<212> TYPE: PRT
<213> ORGANISM: Homo sapiens

<400> SEQUENCE: 29

Val Lys Arg Gly Leu Lys Leu Leu Arg Lys Arg Leu Leu Arg Asp
1               5                   10                  15

```
<210> SEQ ID NO 30
<211> LENGTH: 15
<212> TYPE: PRT
<213> ORGANISM: Homo sapiens

<400> SEQUENCE: 30

Gly Lys Arg Lys Lys Lys Gly Lys Leu Gly Lys Lys Arg Asp Pro
1               5                   10                  15

<210> SEQ ID NO 31
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: The amino acids are in front-back position

<400> SEQUENCE: 31

Pro Asp Arg Lys Lys Gly Leu Lys Gly Lys Lys Arg Lys Lys Gly
1               5                   10                  15

<210> SEQ ID NO 32
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: All amino acids are in configuration D

<400> SEQUENCE: 32

Gly Lys Arg Lys Lys Lys Gly Lys Leu Gly Lys Lys Arg Asp
1               5                   10

<210> SEQ ID NO 33
<211> LENGTH: 13
<212> TYPE: PRT
<213> ORGANISM: Homo sapiens

<400> SEQUENCE: 33

Gly Leu Lys Lys Asn Gly Ser Cys Lys Arg Gly Pro Arg
1               5                   10

<210> SEQ ID NO 34
<211> LENGTH: 15
<212> TYPE: PRT
<213> ORGANISM: Homo sapiens

<400> SEQUENCE: 34

Tyr Arg Ser Arg Lys Tyr Ser Ser Trp Tyr Tyr Ala Leu Lys Arg
1               5                   10                  15

<210> SEQ ID NO 35
<211> LENGTH: 14
<212> TYPE: PRT
<213> ORGANISM: Homo sapiens

<400> SEQUENCE: 35

Ser Arg Arg Ala Arg Arg Ser Pro Arg His Leu Gly Ser Gly
1               5                   10

<210> SEQ ID NO 36
<211> LENGTH: 10
<212> TYPE: PRT
<213> ORGANISM: Homo sapiens
```

```
<400> SEQUENCE: 36

Ala Lys Thr Gly Lys Arg Lys Arg Ser Gly
1               5                   10

<210> SEQ ID NO 37
<211> LENGTH: 13
<212> TYPE: PRT
<213> ORGANISM: Homo sapiens

<400> SEQUENCE: 37

Gln Gly Lys Ser Lys Arg Glu Lys Lys Asp Arg Val Phe
1               5                   10

<210> SEQ ID NO 38
<211> LENGTH: 12
<212> TYPE: PRT
<213> ORGANISM: Homo sapiens

<400> SEQUENCE: 38

Lys His Leu Lys Lys His Leu Lys Lys His Leu Lys
1               5                   10

<210> SEQ ID NO 39
<211> LENGTH: 17
<212> TYPE: PRT
<213> ORGANISM: Homo sapiens

<400> SEQUENCE: 39

Leu Arg Arg Glu Arg Gln Ser Arg Leu Arg Arg Glu Arg Ser Gln Ser
1               5                   10                  15

Arg

<210> SEQ ID NO 40
<211> LENGTH: 32
<212> TYPE: PRT
<213> ORGANISM: Homo sapiens

<400> SEQUENCE: 40

Lys Lys Lys Lys Lys Lys Lys Lys Lys Lys Lys Lys Lys Val Lys Arg
1               5                   10                  15

Gly Leu Lys Leu Arg His Val Arg Pro Arg Val Thr Arg Met Asp Val
                20                  25                  30

<210> SEQ ID NO 41
<211> LENGTH: 31
<212> TYPE: PRT
<213> ORGANISM: Homo sapiens

<400> SEQUENCE: 41

Lys Lys Lys Lys Lys Lys Lys Lys Lys Lys Lys Lys Lys Ser Glu Arg
1               5                   10                  15

Lys Lys Arg Arg Arg Glu Ser Arg Lys Lys Arg Arg Arg Glu Ser
                20                  25                  30

<210> SEQ ID NO 42
<211> LENGTH: 27
<212> TYPE: PRT
<213> ORGANISM: Homo sapiens

<400> SEQUENCE: 42

Lys Lys Lys Lys Lys Lys Lys Lys Lys Lys Lys Lys Lys Ser Arg Arg
1               5                   10                  15
```

```
Ala Arg Arg Ser Pro Arg His Leu Gly Ser Gly
            20                  25

<210> SEQ ID NO 43
<211> LENGTH: 21
<212> TYPE: PRT
<213> ORGANISM: Homo sapiens

<400> SEQUENCE: 43

Val Lys Arg Gly Leu Lys Leu Lys Leu Ala Lys Leu Ala Lys Lys Leu
1               5                   10                  15

Ala Lys Leu Ala Lys
            20

<210> SEQ ID NO 44
<211> LENGTH: 29
<212> TYPE: PRT
<213> ORGANISM: Homo sapiens

<400> SEQUENCE: 44

Lys Leu Ala Lys Leu Ala Lys Leu Ala Lys Leu Ala Lys Gly Lys
1               5                   10                  15

Arg Lys Lys Lys Gly Lys Leu Gly Lys Lys Arg Asp Pro
            20                  25

<210> SEQ ID NO 45
<211> LENGTH: 26
<212> TYPE: PRT
<213> ORGANISM: Homo sapiens

<400> SEQUENCE: 45

Lys Leu Ala Lys Leu Ala Lys Lys Leu Ala Lys Leu Ala Lys Lys His
1               5                   10                  15

Leu Lys Lys His Leu Lys Lys His Leu Lys
            20                  25

<210> SEQ ID NO 46
<211> LENGTH: 18
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Residue of glycine-phthaloyl in N-terminal
      position (Xaa)

<400> SEQUENCE: 46

Xaa Gly Arg Lys Lys Arg Arg Arg Glu Ser Arg Lys Lys Arg Arg Arg
1               5                   10                  15

Glu Ser

<210> SEQ ID NO 47
<211> LENGTH: 18
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Has a salicylic motif (named Xaa) in N-
      terminal position.

<400> SEQUENCE: 47

Xaa Gly Arg Pro Arg Glu Ser Gly Lys Lys Arg Lys Arg Lys Arg Leu
1               5                   10                  15

Lys Pro
```

```
<210> SEQ ID NO 48
<211> LENGTH: 19
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Has a salicylic motif (named X) in C-terminal
      position

<400> SEQUENCE: 48

Gly Arg Pro Arg Glu Ser Gly Lys Lys Arg Lys Arg Lys Arg Leu Lys
1               5                   10                  15

Xaa Pro Gly

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: PAV1U PCR
      Primer

<400> SEQUENCE: 49
gatccgtaaa acgaggacta aaactacgac acgtacgacc acgagtaaca cgaatggacg      60
taa                                                                   63

<210> SEQ ID NO 50
<211> LENGTH: 63
<212> TYPE: DNA
<213> ORGANISM: Artificial Sequence
<220> FEATURE:
<223> OTHER INFORMATION: Description of Artificial Sequence: PAV1L PCR
      Primer

<400> SEQUENCE: 50
gatcttacgt ccattcgtgt tactcgtggt cgtacgtgtc gtagttttag tcctcgtttt      60
acg                                                                   63

<210> SEQ ID NO 51
<211> LENGTH: 51
<212> TYPE: PRT
<213> ORGANISM: Homo sapiens

<400> SEQUENCE: 51

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 52
<211> LENGTH: 51
<212> TYPE: PRT
<213> ORGANISM: Homo sapiens

<400> SEQUENCE: 52

Gly Ile Val Glu Gln Cys Cys Thr Ser Ile Cys Ser Leu Tyr Gln Leu
1               5                   10                  15
```

```
Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Lys Pro Thr
    50

<210> SEQ ID NO 53
<211> LENGTH: 51
<212> TYPE: PRT
<213> ORGANISM: Homo sapiens

<400> SEQUENCE: 53

Gly Ile Val Glu Gln Cys Ser Thr Ser Ile Cys Ser Leu Tyr Gln Leu
1               5                   10                  15

Glu Asn Tyr Ser Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 54
<211> LENGTH: 51
<212> TYPE: PRT
<213> ORGANISM: Bos sp.

<400> SEQUENCE: 54

Gly Ile Val Glu Gln Cys Cys Ala Ser Val Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Ala
    50

<210> SEQ ID NO 55
<211> LENGTH: 51
<212> TYPE: PRT
<213> ORGANISM: Sus sp.

<400> SEQUENCE: 55

Gly Ile Val Glu Glu Cys Cys Lys Gly Val Cys Ser Met Tyr Gln Leu
1               5                   10                  15

Glu Asn Tyr Cys Asn Phe Pro Asn Gln His Leu Cys Gly Ser His Leu
            20                  25                  30

Val Glu Ala Leu Tyr Leu Val Cys Gly Glu Lys Gly Phe Tyr Tyr Ile
        35                  40                  45

Pro Arg Met
    50

<210> SEQ ID NO 56
<211> LENGTH: 21
<212> TYPE: PRT
<213> ORGANISM: Homo sapiens

<400> SEQUENCE: 56

Val Lys Arg Gly Leu Lys Leu Val Lys Arg Gly Leu Lys Val Lys
1               5                   10                  15
```

```
-continued

Arg Gly Leu Lys Arg
            20

<210> SEQ ID NO 57
<211> LENGTH: 19
<212> TYPE: PRT
<213> ORGANISM: Homo sapiens

<400> SEQUENCE: 57

Gly Arg Pro Arg Glu Ser Gly Lys Lys Arg Lys Arg Lys Arg Lys Arg
1               5                   10                  15

Leu Lys Pro
```

AMINO ACID SEQUENCES FACILITATING PENETRATION OF A SUBSTANCE OF INTEREST INTO CELLS AND/OR CELL NUCLEI

RELATED APPLICATIONS

This application is a continuation-in-part of PCT/FR00/02621, filed Mar. 1, 2000 and PCT/FR01/00613, filed Mar. 1, 2001; and claims the benefit of U.S. Ser. No. 60/316,063, filed Aug. 30, 2001 which are incorporated by reference in their entireties.

FIELD OF THE INVENTION

The general field of the invention relates to peptides that comprise amino acid sequences having the ability to facilitate penetration of a substance of interest into cells and/or cell nuclei.

BACKGROUND OF THE INVENTION

Several techniques have been developed thus far to transfer DNA into cells, but none demonstrate real satisfaction. One of them, derived from the Mandel and Higa technique, based on acquisition by *E. coli* susceptible to transformation by treatment with $CaCl_2$, consists of co-precipitating DNA with calcium phosphate or DEA dextran, and introducing the precipitate obtained directly into the cell or nucleus. This method, besides the fact that it is toxic, is not selective.

Another method of directly introducing DNA, electroporation, consists of giving the cells a brief electric shock of several thousand volts, which allows the DNA to pass through the cytoplasmic membrane and to be introduced into the cell. This method is very toxic to the cells, involving high mortality and great variability, depending on the cells used. Other methods use receptors on the membrane to screen the entry of the gene into the cells. The DNA can then penetrate into the cell through either a specific ligand of these receptors, or specific antibodies of membrane constituents. The DNA-ligand complex thus penetrates into the cell by a process of endocytosis. This process is limited due to the fact that there is major destruction of the complex used in the lysosomal vesicles. Several processes have been developed to eliminate these disadvantages, but none gives complete satisfaction.

U.S. Pat. No. 5,635,383 describes another type of complex vector, based on polylysine, for transferring nucleic acids into cells.

U.S. Pat. No. 5,521,291 describes another method based on the use of a conjugate formed from a virus linked to a substance having a strong affinity for DNA via an antibody. Such conjugates are hard to use, and certain risks are associated with the use of viruses.

To try to eliminate these disadvantages, a process was described in patent application No. WO 97/02840 that is used in vitro and consists of using anti-DNA murine antibodies, or their F(ab')2 and Fab' fragments, capable of penetrating inside live cells, as immunovectors for intracytoplasmic and/or intranuclear transfer of biologically active substances. Although these vectors are highly effective, they can be complicated to use in some applications. Using molecules the size and complexity of antibodies can also be a major disadvantage in their handling and implementation.

Patent application No. WO 99/07414 described how it was possible to use peptides in vitro, derived from anti-DNA murine antibodies, described in the above-mentioned application WO 97/02840, as intracytoplasmic and intranuclear internalization vectors for biologically active substances.

Although these murine-origin peptide vectors are coded by the germinal line and carry no mutation, and consequently, should be antigenically close to those encountered in humans, the risk of an immune reaction in humans cannot be excluded.

There is a need for peptides and amino acid sequences that eliminate the disadvantages described above, namely that can be used as, or in, a cell internalization vector in humans and would pose none of the risks mentioned above. Having tools that make it possible to transfer substances of interest effectively from the outside medium to the inside of cells, and more specifically cell nuclei, is a major advantage in the field of biotechnology, especially to produce proteins or peptides to regulate the expression of genes, to analyze and screen intracellular signaling paths, or to analyze the properties of a given substance on a cell. Another important application of such tools concerns the field of gene therapy since, up until the present time, the various gene therapy processes have run into the same need, not met in an optimal way, which is to be able to have vectors that can transfer biologically active ingredients into the cytoplasm and/or the cell nucleus from the host organism being treated, without thereby altering either the genome of the host or the biological properties of the active ingredients transferred.

SUMMARY OF THE INVENTION

The present invention is based in part on the discovery of peptides having the ability to facilitate penetration into a cell. In one aspect, the peptide comprises an amino acid sequence selected from the group consisting of a) $(XBBBXXBX)_n$; b) $(XBBXBX)_n$; c) $(BBX_mBBX_o)_n$; d) $(XBBXXBX)_n$; and e) $(BXBB)_n$, wherein B is a basic amino acid; X is a non-basic amino acid; each m is independently an integer from zero to five; each n is independently an integer between one and ten; and each o is independently an integer between zero to five. In various embodiments n is 2 or 3 and X is a hydrophobic amino acid. A preferred amino acid sequence of the invention is VKRGLKL (SEQ ID NO: 1). The peptide is further characterized by its ability to interact with aminoglycans. Preferred aminoglycans include heparin and chondroitin sulfate.

The peptide described above may further comprise an amino acid sequence selected from the group consisting of a) a CDR3 region of a human anti-DNA antibody; b) a CDR2 region of a human anti-DNA antibody; c) a CDR3 region of a murine anti-DNA antibody, and d) a CDR2 region of a murine anti-DNA antibody.

In another aspect, the invention provides a peptide having the ability to facilitate penetration into a cell, which comprises at least two or more domains, wherein one of the domains comprises an amino acid sequence selected from the group consisting of a) XBBBXXBX; b) XBBXBX; c) $BBX_mBBX_o$; d) XBBXXBX; and e) BXBB, and wherein a second domain comprises an amino acid sequence selected from the group consisting of a) XBBBXXBX; b) XBBXBX; c) $BBX_mBBX_o$; d) XBBXXBX; e) BXBB; and f) an antibody fragment, wherein B is a basic amino acid; X is a non-basic amino acid; each m is independently an integer from zero to five; each o is independently an integer between zero to five. In a preferred embodiment, the at least one domain comprises the amino acid sequence VKRGLKL (SEQ ID NO: 1).

In yet another aspect, the invention provides a peptide having the ability to facilitate penetration into a cell, which comprises at least two domains, wherein each of the domains comprises an amino acid sequence selected from the group consisting of a) a CDR3 region of an anti-DNA antibody; and b) a CDR2 region of an anti-DNA antibody.

The anti-DNA antibody is of human origin. Alternatively, the anti-DNA antibody is of murine origin. In one aspect, the peptide comprises a CDR2 region and a CDR3 region. A preferred peptide comprises the amino acid sequence of SEQ ID NO: 6. Alternatively, the peptide comprises at least two CDR3 regions. A preferred peptide comprises the amino acid sequence of SEQ ID NO: 15. In yet another embodiment the peptide comprises a CDR2 region flanked on each side by a CDR3 region. A preferred peptide comprises the amino acid sequence of SEQ ID NO: 14.

The peptides of the invention are derived from a human protein. Preferably, the peptides are derived from a human lipoprotein B. Most preferably the peptides of the invention comprise the amino acid sequence VKRGLKL (SEQ ID NO: 1). Alternatively, the peptides of the invention comprise an amino acid sequence of SEQ ID NOS: 2, 3, 5, 7, 9, 10, 25-48. In yet another embodiment the peptides of the invention may have the amino acid sequence selected from the group consisting of SEQ ID NOS: 2, 3, 5, 6, 7, 9, 10, 17-21, 25-48.

The peptides of the invention are linked to a substance of interest. Generally, the substance of interest is any active ingredient of a drug, whether it be a chemical, biochemical, natural or synthetic product. The molecules can be small, with a molecular weight of around 500 D, or large like proteins of several thousand Daltons. The substance of interest is directly active or alternatively can be activated in situ by the amino acid sequence, by a distinct agent or by environmental conditions.

In one aspect, the invention provides a method of producing a translocatable conjugate between a peptide of the invention and a substance of interest. This method includes coupling the substance of interest to anyone of the peptides of the invention to form a peptide-substance conjugate.

In another aspect, the invention provides a method of translocating a substance into the cytoplasm and the nucleus of a eukaryotic cell. This method includes coupling the substance to anyone of the peptides of the invention to form a peptide-substance conjugate and contacting a cell culture in the presence of the peptide-substance conjugate.

In another aspect, the invention provides a method of increasing the intracellular concentration of a substance within a eukaryotic cell. This method includes coupling the substance to any one of the peptides of the invention to form a peptide-substance conjugate and contacting the cell with the peptide-substance conjugate, under conditions promoting active metabolism of the eukaryotic cell.

In yet another aspect, the invention provides a composition comprising a therapeutically or prophylactically effective amount of anyone of the peptides of the invention conjugated to a therapeutically active substance, and an acceptable carrier.

Also disclosed is a kit comprising in one or more containers, a therapeutically or prophylactically effective amount of the composition of the invention.

The invention discloses a method of treating or preventing a disease. The method of the invention includes administering to a subject in which such treatment or prevention is desired a composition according to the invention in an amount sufficient to treat or prevent the disease in the subject.

The invention also provides a vector for intracytoplasmic and intranuclear transport. The vector includes anyone of the peptides of the invention. Preferred peptides contain the amino acid sequences of SEQ ID NOS: 5, 7, 10 or 13.

Also provided in the invention is a method for producing anyone of the peptides of the invention. The method includes transfecting a production cell with a vector comprising a nucleic acid molecule encoding the peptide operably linked to an expression control sequence, culturing the production cell under conditions that permit production of the peptide, and isolating the peptide.

In another aspect, the invention provides a peptide comprising an amino acid sequence capable of translocating into the cytoplasm and the nucleus of a cell, wherein the peptide is derived from a lipoprotein, the peptide comprises at least 4 basic amino acids, and is characterized by the ability to interact with aminoglycans in vivo, as measured by binding to at least one aminoglycan selected from the group consisting of heparin, heparin sulfate and chondroitin sulfate. The peptide may be derived from a human lipoprotein, and more preferably from human lipoprotein B.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

BRIEF DESCRIPTION OF THE FIGURES

FIG. 16A: 35A7-1047, 6 h; FIG. 16B: 35A7-HBP7 6 h; FIG. 16C: 35A7-HBP10, 6 h; FIG. 16D: 35A7-1047, 24 h; FIG. 16E: 35A7-HBP7, 24 h; FIG. 16F: 35A7-HBP10, 24 h.

FIG. 17A shows cells incubated and fixed and FIG. 17B shows cells dissociated and cultured before fixation.

FIG. 18A shows cells that were incubated for 6 hours and fixed, FIG. 18B shows cells fixed for 18 hours and fixed and FIG. 18C shows cells dissociated and cultured before fixation. Arrows indicate areas of greater fluorescence.

DETAILED DESCRIPTION OF THE INVENTION

Figure 1:
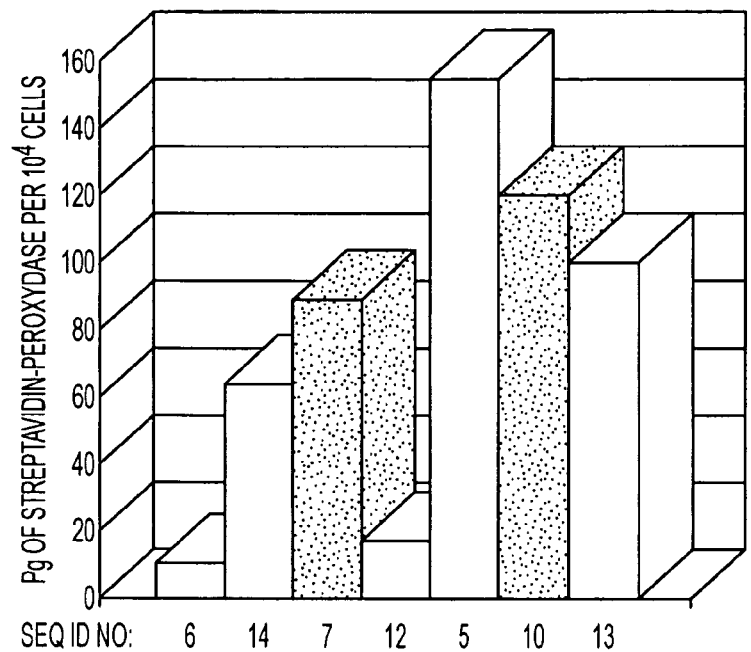
FIG. 1 is a bar graph illustrating internalization of streptavidin-peroxidase transported by various biotinylated peptides.

The present invention discloses peptides which comprise amino acid sequences that have the ability to facilitate penetration of a substance of interest inside cells. In one aspect, the amino acid sequence is characterized by the fact that it comes from a protein of human origin and is capable of reacting with aminoglycans. In the invention, one especially preferred amino acid sequence comes from a protein synthesized by a human cell. Advantageously, the protein synthesized by a human cell is chosen from among the proteins linked to heparin-type or chondroitin sulfate-type aminoglycans. For example, it is an amino acid sequence that comes from human lipoprotein B.

"Facilitate penetration" is understood to mean facilitating the passage or translocation of a substance across a biological membrane, i.e., from the outside medium into the intracellular medium, and quite specifically into the cytoplasm and/or the nucleus of the cell. The biological membrane can be those of prokaryotic or eukaryotic cells. They can include membranes of organelles, either single- or double-membrane bound organelles, as well as plasma membranes. The biological membranes are for example a phospholipid membrane, mitochondrial membrane, or nuclear membrane. This penetration can be determined by various processes, for example by a cell penetration test having a first incubation step for the amino acid sequence in the presence of culture cells, followed by a fixing step and permeabilization of those cells, and then revelation of the presence of the amino acid sequence inside the cell. The revelation step can be done with another incubation in the presence of antibodies marked and directed against the sequence, followed by detection in the cytoplasm or in immediate proximity of the cell nucleus, or even within it, of the immunologic reaction between the sequence and the marked antibodies. Revelation can also be done by marking an amino acid sequence in the invention and detecting the presence of the marking in the cell compartments. A cell penetration test was described in the above-mentioned patent application No. WO 97/02840.

Generally, the amino acid sequences of the invention include a high number of basic amino acids, as is the case in lysine, arginine or histidine, for example. "High number" should be understood as at least equal to 3.

One preferred type of amino acid sequence for use in the invention is composed of, or contains, at least one group of amino acids with one of the following formulae: a) (XBBBXXBX)n; b) (XBBXBX)n; c) (BBX$_m$BBX$_o$)n; d) (XBBXXBX)n; and e) (BXBB)n, wherein B is a basic amino acid; X is a non-basic, preferably hydrophobic amino acid, such as alanine, isoleucine, leucine, methionine, phenylalanine, tryptophan, valine or tyrosine; m is a whole number between 0 and 5; n is a whole number between 1 and 10, preferably between 1 and 3; and o is a whole number between 0 and 5.

Generally, the amino acid sequences have less than 100 amino acids, less than 50 amino acids is considered better, and less than 25 amino acids better yet. Advantageously, the amino acid sequences in the invention have between 6 and 25 amino acids.

Preferred amino acid sequences for use in this invention are those identified by SEQ ID NO: 2, 3, 5, 7, 9, 10, 13, 16, 17, 19, 20, 21, 23, 25, 26, 30, 33, 34, 35, 36, 37, 38 and 39. Among them, those especially preferred are the sequences identified by SEQ ID NO: 2, 3, 5, 7, 9, 10, 13, 16, 19, 20, 21, 23, 25, 26, 30, 36 and 38.

Another preferred type of peptide, for use in this invention, is composed of or includes at least two domains, one of those domains containing an amino acid sequence with the formula: a) XBBBXXBX; b) XBBXBX; c) BBX$_m$BBX$_o$; d) XBBXXBX; or e) BXBB, and the other of those domains having an amino acid sequence with the formula: a) XBBBXXBX; b) XBBXBX; c) BBX$_m$BBX$_o$; d) XBBXXBX; e) BXBB; or f) an antibody fragment, wherein B is a basic amino acid, X is a non-basic amino acid, preferably hydrophobic, m is a whole number between 0 and 5, o is a whole number between 0 and 5.

One particularly interesting amino acid sequence is the sequence SEQ ID NO: 1, to the extent that (1) in the state at least of dimer, it has the desired properties and (2) in the state of monomer or polymer, it gives another amino acid sequence to which it is coupled the properties or substantially potentiates those properties when the sequence already has them. Similarly, the peptides designated HBP3, (HBP3)$_2$, HBP6, HBP7, HBP10 and HBP13 have this potentiation capacity.

More specifically, in one case or another, the desired properties of these amino acid sequences are that they react with heparin, the chondroitin sulfates and their derivatives. The peptides binding to the GAG or, more generally, to the aminoglycans, and in particular to heparin, heparin sulfate and the chondroitin sulfates (peptides generally designated by HBP, for "heparin-binding peptide," even if heparin is only one example of aminoglycan) can be natural in origin, like the peptides described above, or artificial. They can be used in their natural or polymer (dimer, trimer, etc.) form.

It is known that a very large number of cell regulations depend on interactions between the proteins and the glycosaminoglycans (GAG) on the surface of cells (Cardin & Weintraub, Arteriosclerosis 9:21 (1989); Merton et al., Annu. Rev. Cell Biol. 8:365 (1992); David, FASEB J. 7:1023 (1993); Salmivira & Jalkanen, Experimentia 51:863 (1995); Caldwell et al., Int. J. Biochem. Cell Biol. 18:203 (1996); Fromm et al., Arch. Biochem. Bioph. 343:92 (1997)). Such interactions occur, for example, in the control of hemostasis (Hirsch, New Engl. J. Med. 324:1565 (1991)) in the proliferation of smooth muscle cells (Castellot et al., J. Cell Biol. 102:1979 (1986)), in the expression of the activity of the growth factors (Ruoslahti & Yamazuchi, Cell 64:867 (1991)), in the expression of the lipolytic activity of enzymes Robinson, Adv. Lip. Res. 1:1 (1963), in the integrity of the extracellular matrix (Kallunski & Tryggvason, J. Cell Biol. 116: 559 (1992)) and others. In a given system, these biological effects are due to the interaction of one or a limited number of proteins with the GAG on the cell surface. The GAG are constituents very well preserved in the course of evolution, present on the surface of all eukaryotic cells. The GAG are saccharide polymers; for example, heparin is a polymer of disaccharide α-1,4-2-iduronic acid→D-glucosamine and the chondroitin sulfates are polymers of disaccharide N-acetyl chondrosine, containing a very large number of sulfate groups and hence negatively charged. The proteins that react specifically with the GAG all contain, in their sequence, one or more peptide segments that are responsible for the interaction of those proteins with the GAG. The length of these segments varies from one protein to another, ranging from four to thirty amino acids. Nearly all these peptides are positively charged and contain a high number of basic amino acids, above all lysine and arginine. It has been shown that these amino acids participate in preponderant fashion in the interaction of these proteins with the GAG (Cardin & Weintraub, Arteriosclerosis 9:21 (1989); Merton et al., Annu. Rev. Cell Biol. 8:365 (1992); David, FASEB J. 7:1023 (1993); Salmivira & Jalkanen, Experimentia 51:863 (1995); Caldwell et al., Int. J. Biochem. Cell Biol. 18:203 (1996); Fromm et al., Arch. Biochem. Bioph. 343:92 (1997)).

"Heparin or chondroitin sulfate derivatives" or "aminoglycans like heparin or chondroitin sulfate" are understood to mean any product or sub-product as defined in the publications cited in references (Cardin & Weintraub, Arteriosclerosis 9:21 (1989); Merton et al., Annu. Rev. Cell Biol. 8:365 (1992); David, FASEB J. 7:1023 (1993)).

In one embodiment of the invention, the amino acid sequence is coded by the germinal line, and thus does not carry any mutations (substitution, deletion, addition, etc.). The seven sequences described in Table 1 below are particularly useful for intracytoplasmic transport. They are sequences (HBP1)$_3$, HBP6, (HBP3)$_2$, HBP7, HBP11, HBP13 and HBP2.

TABLE 1

| Identity | Sequence AA | % K Total residues | % R Total residues | % K + R | SEQ ID NO |
|---|---|---|---|---|---|
| (HBP1)$_3$ | VKRGLKLVKRGLKLVKRGLKL | 28 | 24 | 52 | 3 |
| HBP6 | GRPRESGKKRKRKRLKP | 32 | 31 | 63 | 21 |
| (HBP3)$_2$ | SERKKRRRESRKKRRRES | 22 | 44 | 67 | 26 |
| HBP7 | GKRKKKGKLGKKRDP | 46 | 13 | 60 | 30 |
| HBP11 | AKTGKRKRSG | 30 | 20 | 50 | 36 |
| HBP13 | KHLKKHLKKHLK | 50 | 0 | 50 | 38 |
| HBP2 | RKGKFYKRKQCKPSRGRK | 33 | 22 | 55 | 25 |

Two sequences are particularly useful for intranuclear transport. They are sequences HBP10 and HBP15. These two sequences are characterized by their high basic amino acid content, and more particularly by the fact that they do not contain any lysine residue, contrary to the sequences useful for intracytoplasmic transport.

Each of the sequences described in Table 1 has at least 20% lysine residues, and at least 50% of the residues are basic amino acids out of the total number of residues in the sequence.

The invention also shows that coupling peptides, or their polymer forms, with a ligand, whose function is to react with a receptor present on the cell membrane, substantially increases that ligand's capacity to attach itself to the cell membrane.

In another aspect, the invention is aimed at using the amino acid sequences defined above to prepare compositions designed to transfer substances of interest into cells. This capacity of the peptides in the invention is an advantage to allow the transport of active substances through biological membranes and, quite specifically, through the hematoencephalic, hematoretinal, intestinal and pulmonary barriers. The peptides in the invention have the interest of being able to be used in forms of administration adjusted to both the active substance to which they are coupled and to the type of cell targeted, particularly those requiring passage through the above barriers.

"Substance of interest" is understood to mean any product presenting an interest, particularly biological, pharmaceutical, diagnostic, tracing, or agro-food. They can be nucleic acids (ribonucleic acid, deoxyribonucleic acid) that can have various origins, and particularly, human, viral, animal, eukaryotic or prokaryotic, vegetable, synthetic, etc., and able to vary in size, ranging from a simple oligonucleotide to a genome or genome fragment. It can also be a viral genome or plasmid or a radio-opaque material. The substance can also be a protein, such as an enzyme, a hormone, a cytokine, an apolipoprotein, a growth factor, an antigen, an antibody, an antibody fragment, etc. The antibody can be a monoclonal antibody, such as IgG or IgM. The antibody fragment can be a single chain scFv. The substance of interest can also be a pharmaceutical composition such as a toxin, antibiotic, antiviral molecule or immune modulator. The scope of the invention extends to combinations of the amino acid sequence with a substance of interest as defined above.

A substance of interest is insulin. As used herein the term "insulin" shall be interpreted to encompass insulin analogs, natural extracted insulin, or recombinantly produced insulin that is biologically active. By biologically active is meant the molecule has the ability to suppress or prevent disease symptoms of diabetes, e.g. decrease serum glucose. Biologically active insulin includes preproinsulin, proinsulin, insulin alpha chain, insulin beta chain and mature insulin, e.g., alpha and beta chain. The insulin can be derived from any species such as human, bovine, porcine, equine, canine or murine.

The term is intended to encompass the polypeptide normally used in the treatment of diabetes in a substantially purified form but encompasses the use of the term in its commercially available pharmaceutical form, which includes additional excipients. Insulin for use in the present invention can be obtained from numerous commercial sources such as Novo Laboratories (Danbury, Conn.), Nordisk-USA (Rockville, Md.) and Eli Lilly and Co. (Indianapolis, Ind.).

Porcine-derived insulin, human semi-synthetic insulin (Nordisk-USA) and cloned recombinant insulin (Eli Lilly) can be used when practicing the method of the present invention. The insulin is preferably recombinantly produced and may be dehydrated or in solution.

The term "insulin analog" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which still has at least one function of native insulin such as for example, decreasing blood glucose levels. In general, the term "insulin analogs" of the present invention include "insulin lispro analogs", as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

Novel insulin A-chain mutants are also useful in this invention. The human insulin A-chain analogue preserves the native intra-molecular disulfide bond between the residues $Cys^{46}$ and $Cys^{A11}$ and two serines in positions 7 and 30 replace the cysteines implied in the two interchain disulfide bridge formed with the B-chain in the native insulin.

The insulin polypeptide, and/or nucleic acid encoding an insulin polypeptide can be constructed using insulin encoding sequences are known in the art. Sources for insulin polypeptides and nucleic acids encoding insulin polypeptides include GenBank Accession Nos. 600165A; 550085A; AAH05255; AAA59179 and are incorporated herein by reference in their entirety.

Exemplary insulin molecules include, but are not limited to,

The invention shows that coupling peptides with polypeptide vectors capable of penetrating inside cells substantially increases the translocation power of those vectors.

"Coupling" or "conjugating" is understood to mean any type of interaction allowing a physical association between the substance of interest and the vector. It can be cleavable or non-cleavable according to the biological medium and/or the substance of interest transported by the peptides of the invention or it can be cleavable by physical means applied to the organism to which the vector coupled to the active substance has been administered. Thus, the expression of the biological effect of the substance can require that it be released from the vector. Doxorubicin can be cited as an example of a substance of interest that is preferably released from the vector.

The peptides as defined above are capable of transporting inside cells substances that are combined with them covalently or non-covalently, and are thus effective vectors for intracellular transfer of the substances of interest.

In one embodiment, the invention concerns the use of the amino acid sequences in a peptide vector. These vectors, due to the properties of the amino acid sequences, can be used easily for intracytoplasmic and intranuclear transfer in humans, with no risk to them or any degradation of the substance of interest coupled to the vector.

To achieve this goal, it is necessary for a vector to be capable of transporting relatively large quantities of molecules inside cells and for it not to be recognized as a foreign antigen by the human immune system.

Table 1B below gives, for several peptides in the invention, their level of intracytoplasmic and/or intranuclear penetration coupled to a low-molecular weight marker allowing their detection as biotin or fluorescein (Tag) or to a biological substance of interest (Subst).

The results given in Table 1B are based on the experimental data reported hereinafter.

TABLE 1B

| Peptide | SEQ ID NO | Intracytoplasmic | | Intranuclear | |
| --- | --- | --- | --- | --- | --- |
| | | Tag | Subst | Tag | Subst |
| HBP1 | 1 | +/− | ND | − | − |
| (HBP1)₂ | 2 | +/− | + | − | − |
| (HBP1)₃ | 3 | ++ | ++ | +/− | +/− |
| | 4 | | | | |
| | 5 | | | | |
| | 6 | | | | |
| | 7 | | | | |
| | 8 | | | | |
| | 9 | | | | |
| | 10 | | | | |
| | 11 | | | | |
| | 12 | | | | |

```
GIVEQCCTSICSLYQLENYCNFVNQHLCGSHLVEALYLVCGERGFFYTPKT;  (SEQ ID NO: 51, human insulin)

GIVEQCCTSICSLYQLENYCNFVNQHLCGSHLVEALYLVCGERGFFYTKPT;  (SEQ ID NO: 52, human lyspro insulin)

GIVEQCSTSICSLYQLENYSNFVNQHLCGSHLVEALYLVCGERGFFYTPKT;  (SEQ ID NO: 53, human "mini-insulin")

GIVEQCCASVCSLYQLENYCNFVNQHLCGSHLVEALYLVCGERGFFYTPKA;  (SEQ ID NO: 54, bovine insulin) and GIVEECCKGVCSMYQLENYCNFPNQHLCGSHLVEALYLVCGEKGFYYIPRM.  (SEQ ID NO: 55, porcine insulin)
```

TABLE 1B-continued

| Peptide | SEQ ID NO | Intracytoplasmic Tag | Intracytoplasmic Subst | Intranuclear Tag | Intranuclear Subst |
|---|---|---|---|---|---|
|  | 13 |  |  |  |  |
|  | 14 |  |  |  |  |
|  | 15 |  |  |  |  |
|  | 16 |  |  |  |  |
| HBP4 | 17 | +/− | ND | − | − |
| HBP5 | 18 | +/− | ND | − | − |
| (HBP5)$_2$ | 19 | + | + | − | − |
| HBP2 | 20 | + | ++ | − | − |
| HBP6 | 21 | +++ | +++ | +/− | +/− |
|  | 22 |  |  |  |  |
|  | 23 |  |  |  |  |
|  | 24 |  |  |  |  |
|  | 25 |  |  |  |  |
| (HBP3)$_2$ | 26 | +++ | +++ | + | + |
|  | 27 |  |  |  |  |
|  | 28 |  |  |  |  |
|  | 29 |  |  |  |  |
| HBP7 | 30 | +++ | +++ | + | +/− |
|  | 31 |  |  |  |  |
|  | 32 |  |  |  |  |
| HBP8 | 33 | +/− | +/− | − | − |
| HBP9 | 34 | +/− | +/− | − | − |
| HBP10 | 35 | +/− | +/− | ++ | ++ |
| HBP11 | 36 | ++ | ++ | +/− | +/− |
| HBP12 | 37 | +/− | +/− | − | − |
| HBP13 | 38 | ++ | ++ | +/− | +/− |
| HBP15 | 39 | +/− | + | +++ | +++ |

These results indicate that the peptides that are capable of massive nuclear translocation are those whose positive charge is mainly comprised of the presence of arginine and the almost total absence of lysine.

The first group of peptides of the invention includes amino acid sequences capable of allowing penetration of a substance of interest inside the cell, but little or none inside the nucleus. Examples that can be cited are the peptides in sequences SEQ ID NO: 2, 3, 17, 18, 19, 20,21, 33, 34, 37 and 38.

The second group of peptides of the invention has amino acid sequences capable of allowing penetration of a substance of interest inside the cell and the cell nucleus. Examples that can be cited are the peptides in sequences SEQ ID NO: 26, 35 and 39. It has been found that these peptides can be used both in vivo and in vitro as agents for internalizing substances of interest into cells.

A vector in the invention is characterized by the fact that it is composed of, or includes, an amino acid sequence as defined above.

As a variation, the vector is based on coupling, on one hand, of amino acid sequences reacting with aminoglycans and, on the other hand, of new peptides derived from the variable part of human anti-DNA antibodies. The coupling of amino acid sequences reacting with aminoglycans and peptides derived from variable parts of human anti-DNA antibodies inside one and the same molecule results in the preparation of a peptide vector that is particularly effective in translocation and intracellular transfer of substances of interest, above all when the amino acid sequences reacting with the aminoglycans are human in origin.

This combination also gives rise to a translocation and transfer vector specially adapted for use in humans. Indeed, as indicated above, although the peptide vectors of murine origin known from WO 97/02840 are coded by the germinal line and carry no mutations, and consequently should be close to those encountered in humans in terms of antigens, it is possible that their injection into humans would induce an immune reaction. The peptide vector formed from HBP according to the invention and from peptides derived from anti-DNA antibodies, both of human origin, coded by the germinal line and carrying no mutations, prevents this problem.

The general characteristics of these peptides derived from human anti-DNA antibodies are close to those of the peptides of murine origin described in publication WO 99/07414, while they have additional properties that distinguish them from the latter, namely:

1) The ability to penetrate inside cells, they have to have an active cell metabolism (culture temperature between 25° C. and 39° C., preferably and 37° C.), while the murine peptides are clearly less dependent;

2) They react much less strongly with DNA than the murine vectors;

3) Their penetration capacity is not significantly influenced by the molecule they are going to transport inside the cell;

4) They penetrate better inside cells of human origin than inside cells of other origins.

The invention provides a vector composed of a HBP and one or more antibody fragments, preferably polyreactive, and more specifically one or more fragments that come from hypervariable regions of the antibody. Preferably, the vector that is the subject of the invention is characterized by the fact that it contains a fragment of the heavy chain of an antibody.

In the above-mentioned patent application WO 99/07414, only fragments of a monoclonal IgG were used, which is a monomer immunoglobulin that is small in size and has a low molecular weight. The invention shows that it is also possible to use a fragment that comes from an IgM, which is a pentamer immunoglobulin, with a very high molecular weight.

The subject of the invention is therefore a vector for cell internalization, characterized by the fact that it contains one or more HBP and one or more fragments of an IgM or an IgG. Preferably, the vector contains all or part of the CDR2 region of an antibody. As a variation, the vector contains all or part of the CDR3 region of an antibody. More specifically, the vector contains at least one CDR3 region of an anti-DNA human antibody, selected from the group consisting of RTT79, NE-1 and R172.

In another variation, the vector of the invention can also contain all or part of region CDR2, and all or part of region CDR3.

By "all or part" it is understood that the vector of the invention can contain either the whole CDR region concerned, or only part of it, provided that the vector retains the capacity to penetrate into the cells (functional homologue). By "part of CDR region" is understood a CDR region deprived of one or more terminal amino acids. It can also be a CDR region in which one or more internal residues have been deleted or substituted for other amino acids, preferably amino acids of the same nature (basic amino acids, for example).

Some of the examples given in this patent application are based on the use of SEQ ID NO: 1 which comes from human lipoprotein B, but for a person skilled in the art, it is obvious that any natural or artificial HBP can be used.

As indicated above, the vector of the invention is particularly well suited for intracellular and intranuclear transport and transfer of substances of interest.

Unlike other techniques of internalization of a substance of interest into a cell, the techniques of the present invention rely on energy. Penetration of the peptides is completely inhibited by incubating the cells at 4° C. It is also partly inhibited by inhibitors of cell metabolism, like sodium azide (inhibitor of ATPase) and genistein (inhibitor of tyrosine kinase and the bond to ATP). Therefore the mechanism for internalization of the peptides of the invention, and hence of the substances of interest coupled to the peptides, is dependent on energy. The vectorization using the peptides of the invention is therefore done via a receptor. The amino acid sequences of the invention are therefore characterized by their capacity to be fixed to a receptor located on the cell membrane and to cross the cell membrane via the receptor. Thus, the amino acid sequences of the invention are characterized by their capacity to be able to cross the cell membranes by an active mechanism, then to lodge in the cytoplasm and/or cell nucleus. They are therefore distinguished from the peptide transporters in the prior art that were capable of crossing the cell membrane in a passive way.

It is thus possible to have a vector whose use is not limited, when it passes into the cell, by the size of the substances being transported. Indeed, the vectors of the invention are capable of transporting drugs, ranging from small chemical molecules (low molecular weight) to proteins or plasmid-type nucleic acids (high molecular weight). The use of these vectors thus opens a new path in intracellular protein therapy or gene therapy. This special capacity of the vectors of the invention for penetration makes it possible to target "drugs" in the cells in a preferential way, thus contributing to a potential reduction in the toxicity of the drugs and a potential increase in the efficacy index.

The invention is therefore aimed at supplying a vector such as the one described above, characterized by the fact that it contains a substance of interest naturally, or not naturally, that can be incorporated into the cells and/or the nuclei of the cells.

More specifically, the subject of the invention is a vector whose penetration capacity is quite independent from the nature of the substance of interest that is coupled to it. This characteristic, proper to these human vectors compared to the murine vectors, is of primary interest in the planned use of these vectors. But the invention is also interested in vectors that are adapted to the substance of interest which is coupled to it.

However, the interaction must be solid enough that the vector does not dissociate before or during cell penetration. For this reason, the coupling preferred in the invention is covalent coupling, although it can be non-covalent coupling. The substance of interest can be coupled directly to the peptide either on one of those terminal ends or on a side chain or one of the amino acids. The substance of interest can also be coupled indirectly by a connecting arm either to one of the terminal ends of the peptides or to a side chain of one of the amino acids.

The coupling can be done by any chemical, biochemical, enzymatic or genetic coupling process known to a person skilled in the art, but it is generally preferred to use a homo-functional or heterofunctional bridging reagent like succinimidyl 4-(N-maleimidomethyl) cyclohexane-1-carboxylate (SMCC). Other coupling means that can be cited are those chosen from among: bi-functional or multi-functional agents containing alkyl, aryl, aralkyl or peptide groups; esters; aldehydes or alkyl, aryl or aralkyl acids; anhydride, sulfhydrile or carboxyl groups such as maleymil benzoic acid and maleymil propionic acid derivatives and succinimidyl derivatives; groups derived from bromide or cianogenic chloride, carbonyldiimidazole, succinimide esters or sulphonic halogenides.

In another embodiment of the invention, the substance of interest can also be coupled by any genetic engineering technique known to a person skilled in the art. "Genetic engineering" means using an expression vector in which the DNA coding for peptide vectors is cloned in phase in 5' and/or 3' of the complementary DNA of the gene of interest. Expression of the fusion protein is under the control of a promoter. The expression system can be used in a prokaryotic or eukaryotic host cell for the production of the fusion protein. In a first form of embodiment, the substance of interest is coupled at the N-terminal end of the amino acid sequence in the invention. In a second form of embodiment of the invention, the substance of interest is coupled at the C-terminal end of the sequence.

Surprisingly, it has been shown that the vector that is the subject of the invention is capable of potentiating the biological activity and, potentially, reducing the toxicity of the coupled substance. The invention therefore also has as its subject a vector characterized by the fact that it makes it possible to increase the biological activity of the substance of interest to which it is coupled.

It has also been shown that the vector of the invention permits transfection of cells in vitro.

In one embodiment of the invention, the vector is coupled to the substance of interest by at least one molecule (called an "anchoring molecule") that has a strong natural affinity for the substance of interest to be internalized. The natural affinity of the anchoring molecule for the substance of interest allows the transporter to interact non-covalently with the substance of interest, and hence to carry it along in intracellular travel.

Another especially interesting advantage of this type of transporter consists of the fact that, due to the natural affinity of the anchoring molecule for the substance of interest, these two elements are coupled in a totally natural way, with no chemical or biochemical interaction.

This type of transporter is particularly interesting in a case where the substance of interest, due to its size and/or its structure, proves difficult to couple directly to the amino acid sequence. This type of transporter can also prove particularly useful when the substance of interest is not very stable, and when any kind of chemical interaction for coupling it could degrade it or alter its activity.

In addition, the transporter in the invention cannot be specific for a single substance of interest, but can, on the contrary, permit internalization of several different substances of interest inside cells and/or cell nuclei.

The invention also concerns eukaryotic cells that contain an amino acid sequence of the invention. It also concerns eukaryotic cells that contain a vector and/or a transporter according to the invention. It also concerns any type of eukaryotic cell that has been transfected by a vector and/or transporter according to the invention.

The invention also concerns a process to transfer a substance of interest inside a cell in vitro and to increase the biological activity of the substances of interest that has the following steps:

a) coupling the substance to an amino acid sequence, to a vector or to a transporter according to the invention, as described above, and b) incubating the cell with the coupling product at a culture temperature that permits active metabolism of the cell.

Such a temperature is between 25° C. and 39° C., preferably 37° C.

This invention also concerns a composition having as its active ingredient either vectors or transporters loaded with at least one substance of interest according to the invention, or eukaryotic cells that have been transfected according to the invention. Its subject is also the use of such compositions for the formulation and preparation of biological, pharmaceutical, cosmetic and agro-food products.

The scope of the invention extends to pharmaceutically acceptable alkaline or acidic addition salts, hydrates, esters, solvates, precursors, metabolites or stereoisomers, of the vectors and transporters loaded with at least one substance of interest. The scope of the invention also extends to pharmaceutical formulations having a vector or transporter loaded with at least one substance of interest in combination with a pharmaceutically acceptable vehicle, diluent or excipient.

The expression "pharmaceutically acceptable salts" refers to non-toxic salts of the amino acid sequences in the invention that can generally be prepared by having the free base react with a suitable organic or inorganic acid. These salts retain their biological efficacy and the properties of the free bases. Representative examples of the salts that can be cited are water-soluble and water-insoluble salts, such as acetates, ansonates (4,4-diaminostilbenes-2,2'-disulfonates), benzene sulfonates, benzonates, bicarbonates, bisulfates, bitartrates, borates, bromides, butyrates, calcium edetates, camsylates, carbonates, chlorides, citrates, clavulariates, dichlorohydrates, edetates, edisylates, estolates, esylates, fumarates, gluceptates, gluconates, glutamates, glycolylarsanylates, hexafluorophosphates, hexylresorcinates, hydrabamines, hydrobromides, hydrochlorides, hydroxynaphthoates, iodides, isothionates, lactates, lactobionates, laurates, malates, maleates, mandelates, mesylates, methyl bromides, methyl nitrates, methyl sulfates, mucates, napsylates, nitrates, 3-hydroxy-2-naphthoates, oleates, oxalates, palmitates, pamoates (1,1-methylene-bis-2-hydroxy-3-naphtoates, emboates), pantothenates, phosphates/diphosphates, picrates, polygalacturonates, propionates, p-toluene sulfonates, salicylates, stearates, subacetates, succinates, sulfates, sulfosalicylates, suramates, tannates, tartrates, teoclates, tosylates, triethiodides, valerates and salts of N-methylglucamine ammonium.

A subject can be treated with a pharmaceutically effective quantity of a peptide, a vector or a transporter according to the invention, loaded with at least one substance of interest. The expression "pharmaceutically effective quantity" means a quantity capable of making the substance of interest penetrate sufficiently to induce the biological or medical response of a tissue, system, animal or human as expected by the researcher or attending physician.

The invention also covers pharmaceutical compositions suitable for the introduction of a substance of interest into a cell or cell nucleus. The compositions contain an effective quantity of a vector or transporter according to the invention, loaded with at least one substance of interest, alone or in combination with one or more pharmaceutically acceptable supports. The compositions are particularly useful in the sense that they have very low toxicity, or are non-toxic.

The vectors or transporters in the invention, or their salts, loaded with at least one substance of interest, can be administered by any of the routes of administration accepted for therapeutic agents. These processes include systemic administration, for example oral, nasal, parenteral or topical administration, for example transdermal or even central administration, for example by the intracranial surgical route or intraocular administration.

Oral administration can be used by means of tablets, gel capsules, soft capsules (including delayed or extended-release formulations), pills, powders, granules, elixirs, tinctures, suspensions, syrups and emulsions. This form of presentation is particularly suitable for passage through the intestinal barrier.

Parenteral administration is generally done by subcutaneous, intramuscular or intravenous injection or by infusion. The injectable compositions can be prepared in the traditional forms, either in suspension or liquid solution or in solid form for extemporaneous dissolution in a liquid. This form of presentation is more specifically adapted for passage through the hematoencephalic barrier.

One possibility of parenteral administration uses implantation of a slow or extended-release system that makes sure a constant dosage level is maintained, for example according to U.S. Pat. No. 3,710,795.

For intranasal administration, suitable intranasal vehicles can be used.

For transdermal administration, transdermal cutaneous stamps well known to a person skilled in the art can be used. A transdermal-release system permits continuous administration.

Other preferred topical preparations include creams, unguents, lotions, aerosol sprays and gels.

Based on the planned route of administration, the compounds can come in solid, semi-solid or liquid form.

For the solid compositions, such as tablets, pills, powders or granules in the free state or included in gel caps, the active ingredient can be combined with: a) diluents, for example lactose, dextrose, sucrose, mannitol, sorbitol, cellulose and/or glycine; b) lubricants, for example silicone, talc, stearic acid, its magnesium or calcium salt and/or polyethylene glycol; c) binders, for example magnesium and aluminum silicate, starch paste, gelatin, tragacanth gum, methyl cellulose, sodium carboxymethyl cellulose and/or polyvinyl pyrrolidone; if necessary, d) disintegrators, for example, starch, agar, alginic acid or its sodium salt, or effervescent mixtures; and/or e) absorbents, dyes, aromatic agents and sweeteners. The excipients can be, for example, mannitol, lactose, starch, magnesium stearate, sodium saccharine, talc, cellulose, glucose, sucrose, magnesium carbonate and pharmaceutical quality analogs.

For semi-solid compositions, such as suppositories, the excipient can be, for example, an emulsion or fatty suspension, or one with a polyalkylene glycol base, such as polypropylene glycol.

The liquid compositions, particularly injectables or those to be included in a soft capsule, can be prepared, for example, by dissolution, dispersion, etc. of the active ingredient in a pharmaceutically pure solvent such as, for example, water, physiological serum, aqueous dextrose, glycerol, ethanol, an oil and the like.

The vectors or transporters in the invention, loaded with at least one substance of interest, can also be administered in the form of liposome-type release systems, such as in the form of small unilamellar vesicles, large unilamellar vesicles and multilamellar vesicles. The liposomes can be made from a variety of phospholipids, containing cholesterol, stearoylamine or phosphatidyl cholines. In one embodiment, a film of liquid components can be hydrated with an aqueous solution of the drug to form a lipid layer encapsulating the medication, as described in U.S. Pat. No. 5,262,564.

The compounds in the invention can be sterilized and/or contain adjuvants and non-toxic auxiliary substances, such as preserving, stabilizing, wetting or emulsifying agents, agents promoting dissolution, salts to regulate osmotic pressure and/or buffers. They can also contain other substances that have therapeutic interest. The compositions are prepared, respectively, by traditional mixing, granulating or coating processes, and they contain around 0.1% to 75%, preferably around 1% to 50% active ingredient.

The vectors or transporters in the invention, loaded with at least one substance of interest, can also be coupled with soluble polymers, such as targetable drug supports. Such polymers can contain polyvinyl pyrrolidone, pyrane copolymer, polyhydroxypropyl-methacrylamide-phenol, polyhydroxy-ethyl-aspanamide-phenol or poly (ethylene oxide)-polylysine substituted with palmitol residues. The compounds in this invention can also be coupled to a class of biodegradable polymers useful in producing controlled release of a drug, for example, poly(lactic acid), poly(epsilon-caprolactone), poly(hyroxybutyric acid), the polyortho esters, the polyacetals, the polydihydropyranes, the polycyanoacrylates and the reticulated or amphipathic sequenced hydrogel copolymers.

The dosage for the administration of the vectors or transporters in the invention, loaded with at least one substance of interest, is chosen depending on a diversity of factors including the type, species, age, weight, sex and medical condition of the subject; the seriousness of the condition being treated; the route of administration; the status of the subject's kidney and liver functions, and the nature of the particular compound or salt used. A regularly experienced physician or veterinarian will easily determine and prescribe the effective quantity of the vector or transporter loaded with the substance of interest in order to prevent, thwart or stop the progress of the medical condition being treated. Any of the above pharmaceutical compositions can contain from 0.1% to 99%, preferably 1% to 70%, of the active ingredient.

As examples, the oral dosages of the vectors or transporters in the invention, loaded with at least one substance of interest, when they are used for the effects indicated, will be between around 0.05 and 1,000 mg/day by the oral route and, preferably come in the form of tablets containing 0.5, 1.0, 2.5, 5.0, 10.0, 15.0, 25.0, 50.0, 100.0, 250.0, 500.0 and 1,000.0 mg of active ingredient. The effective plasma levels of the vectors or transporters loaded with at least one substance of interest will range from 0.002 mg to 50 mg per kilogram of body weight and per day.

The vectors or transporters in the invention, loaded with at least one substance of interest, may be administered in the form of single daily doses, or the total daily dose may be administered in two, three or four doses per day.

In one particular application, this invention relates to a diagnostic agent for in vitro use, composed of or containing at least one vector, one transporter and/or one cell according to the invention. Such a diagnostic agent can also be used in vivo.

The subject of this invention is therefore also a diagnostic kit that includes the diagnostic agent. More specifically, the diagnostic kit includes a predetermined quantity of a composition in the invention, in one or more containers.

Similarly, the amino acid sequence in the invention, or a vector and/or a transporter containing that amino acid sequence, or cells transfected with the help of the vector, can be used in vivo for preventative purposes, for example and in a non-limiting way, for the prevention of viral infections, metastases, cell apoptosis (e.g., degenerative diseases, tissue ischemia), or for therapeutic purposes, for example the treatment of infectious diseases (e.g., viral, bacterial), cancer and pathological neo-angiogenesis.

The invention provides methods of producing a translocatable conjugate between a peptide and a substance of interest, the method comprising: coupling the substance of interest to any one of the peptides of the invention to form a peptide-substance conjugate which is capable of crossing a biological membrane.

In another embodiment, the invention provides a method of translocating a substance of interest across a biological membrane of a eukaryotic cell, the method comprising: coupling the substance of interest to any one of the peptides of the invention to form a peptide-substance conjugate; and contacting a cell culture in the presence of the peptide-substance conjugate.

In another embodiment, the invention provides a method of translocating a substance of interest across a biological membrane of a eukaryotic cell, the method comprising: contacting a cell culture in the presence of the peptide-substance conjugate.

In yet another embodiment, the invention discloses a method of increasing the intracellular concentration of a substance of interest within a eukaryotic cell, the method comprising: coupling the substance of interest to any one of the peptides of the invention to form a peptide-substance conjugate; and contacting the cell with the peptide-substance conjugate, under conditions promoting active metabolism of the eukaryotic cell.

In yet another embodiment, the invention discloses a method of increasing the intracellular concentration of a substance of interest within a eukaryotic cell, the method comprising: contacting the cell with the peptide-substance conjugate, under conditions promoting active metabolism of the eukaryotic cell.

Also disclosed is a method of increasing the intracellular concentration of a substance of interest within a eukaryotic cell, the method comprising: producing a peptide substance of interest, wherein the peptide substance is any one of the peptides of the invention and contacting the cell with the peptide-substance conjugate, under conditions promoting active metabolism of the eukaryotic cell.

In a related embodiment, the invention provides a method of treating or preventing a disease, the method comprising administering to a subject in which such treatment or prevention is desired a composition according to the invention in an amount sufficient to treat or prevent the disease in the subject.

In another aspect, the invention provides for a method for producing a peptide of the invention comprising transfecting a production cell with a vector comprising a nucleic acid molecule encoding the peptide operably linked to an expression control sequence, culturing the production cell under conditions that permit production of the peptide, and isolating the peptide.

Other advantages and characteristics of the invention will appear from the examples of embodiment that follow and refer to the attached drawings.

EXAMPLES

Example 1

Materials and Methods

Cell Lines:
Normal Cells:
  PtK2, kangaroo rat kidney fibroblasts
  3T3, mouse embryo fibroblasts
  HUVEC, human endothelial cells
  CHO, Chinese hamster ovaries
  HUVEC, endothelial cells transfected by a cell multiplication gene
  CHO, hamster kidney cells
  CHO-745, cells from the CHO line defective for the synthesis of xylosyl transferase
Tumor Cells:
  H1299, human pulmonary carcinoma
  HH9, tumor epithelial cells from the human breast transfected by a gene coding for a growth factor
  MCF7, human tumor epithelial cells MCF7 ras, MCF7 cells transfected by the ras gene
HeLa, carcinoma from the neck of the human uterus
HCT 116, carcinoma from the human colon
HT-29, adenocarcinoma from the human colon
LS174T, adenocarcinoma from the human colon
B16-F10, cells from murine melanoma
Daudi, human Burkitt's lymphoma Cell Culture:

The cells are cultivated in a DMEM medium containing 2% L-glutamine, 1% sodium pyruvate, penicillin (100 U/ml), streptomycin (100 µg/ml) and 10% fetal calf serum (complete medium) at 37° C. in the presence of 5% $CO_2$.

Preparation of Peptides:

Chemical Synthesis:

Peptide synthesis is done by techniques known to a person skilled in the art (Altergen and Neosystem). They are used in solid phase on Fmoc resin. Cleaving is done with trifluoroacetic acid (TFA), and the peptides were purified on a semi-preparatory HPLC-CR C5 column and diluted with a 0.1% TFA solution and an acetonitrile gradient (10%-70%) in the TFA. The lyophilized peptides were dissolved in NaCl 0.15 M.

Molecular Construction Allowing Preparation of Proteins Containing the Peptides in the Invention:

Molecular biology techniques make it possible to construct plasmids which, once introduced into adequate cells, permit the synthesis of vectorized macromolecules.

Figure 10:
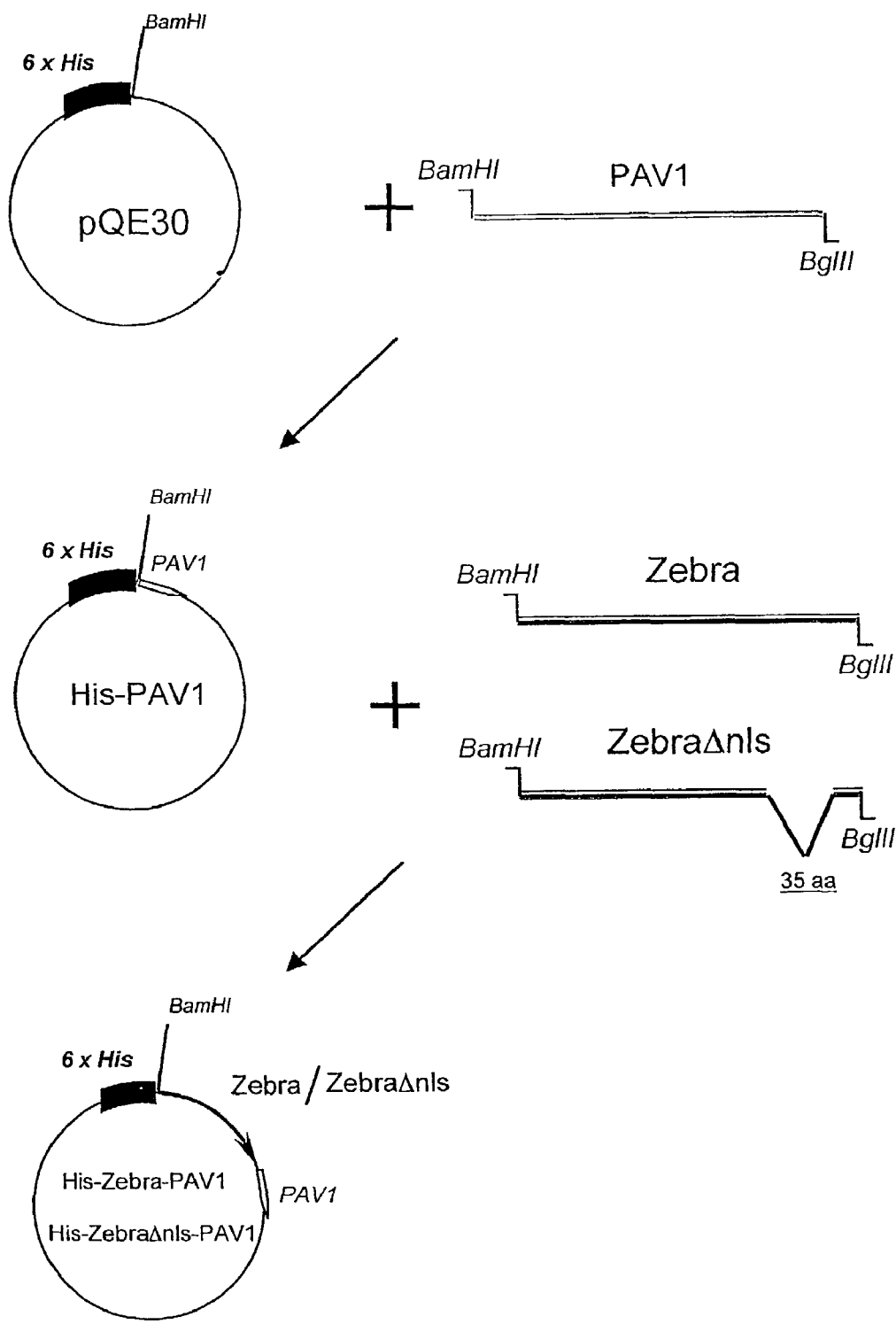
FIG. 10 shows a schematic description of the preparation of vectors for the expression of recombinant proteins containing the peptides of the invention.

Construction of Vectors for Expression of Recombinant Proteins:

FIG. 10 shows the preparation of vectors that permit the expression of recombinant proteins containing the peptide sequences in the invention. The prokaryotic vector pQE30 (Qiagen) permits the expression of genes in the form of fusion proteins (or recombinant proteins) with the sequence 6XHis. This vector carries the origin of replication ColE1, the strong promoter of phage T5, which can be induced by IPTG, the gene for β-lactase giving resistance to ampicillin and a multiple cloning site at 3' of the sequence coding the label 6XHis permitting the cloning of complementary DNA in phase with the 6XHis sequence.

The complementary oligonucleotides of 63-mer:

```
PAV1U: (SEQ ID NO: 49)
5' gatccgtaaaacgaggactaaaactacgacacgtacgaccacgagt
aacacgaatggacgtaa 3'

PAV1L: (SEQ ID NO: 50)
5' gatcttacgtccattcgtgttactcgtggtcgtacgtgtcgtagtt
ttagtcctcgttttacg-- 3'
``` are hybridized. The DNA segment obtained has a BamHI site at 5' and a BglII site at 3'. It codes for the peptide sequence PAV1: VKRGLKLRHVRPRVTRMDV (SEQ ID NO: 10). This fragment is cloned at the BamHI site of vector pQE30. The complementary DNA (DNAc) coding for the Zebra viral protein (BZLF1) of the Epstein-Barr virus (EBV) or the Zebra protein deleted from its nuclear localization site (nls) of 35 amino acids were obtained by PCR. They were cloned at the BamHI site of the vector His-PAV1 or pQE30. The resultant plasmids permit the expression of recombinant proteins $His_6$-Zebra-PAV1, $His_6$-ZebraΔnls-PAV1, $His_6$-Zebra and $His_6$-ZebraΔnls after transformation of the E. coli bacteria.

Induction, Extraction and Purification of Recombinant Proteins:

The production of recombinant proteins is induced at 37° C. by the addition of 1 mM of IPTG (isopropyl-β-D-thiogalactopyranoside) to the bacterial cultures in exponential growth phase in Luria Bertani medium supplemented with 40 µg/ml of ampicillin. 12 hours after adding IPTG, the bacteria are centrifuged at 5700 g for 15 min. at 4° C. The bacterial residue is put in 5 volumes of denatured lysis buffer (20 mM Tris-HCl pH 7.8; 0.5 M NaCl; 10% glycerol; 6 M guanidine-HCl). After 20 min. of incubation at ambient temperature with slow mixing, the lysate is clarified by centrifuging it for 30 min. at 15000 g at 4° C. The supernatant containing the recombinant protein is stored at −80° C.

The 6XHis recombinant proteins are purified by affinity chromatography on a "TALON" resin column (CLONTECH) pre-calibrated with denatured lysis buffer. After 3 successive washings of resin with 10 volumes of denatured lysis buffer containing 10 mM imidazole, the recombinant protein bonded to the column is renatured by a gradient of 6 to 0 M of guanidine-HCl in buffer 20 mM Tris-HCl pH7.8; 0.5 M NaCl; 10% glycerol; 0.5 mM PMSF. The recombinant protein is eluted with a gradient of 20 mM at 1 M of imidazole pH 8.0. The different eluates are analyzed on 12% SDS-acrylamide denatured gel. The fractions containing the purified protein are collected and dialyzed for 2 hours at 4° C. against the buffer 20 mM HEPES pH 7.5, 150 mM NaCl. The protein is concentrated, aliquoted and quick frozen in liquid nitrogen and stored at −80° C.

Peptides Used:

Non-Functionalized Peptides:

The following sequences (SEQ ID NO: 1 to SEQ ID NO: 48) are listed in the appendix.

SEQ ID NO: 1. Peptide reacting with heparin that comes from the amino acid sequence (3358-3372) of the human lipoprotein B, Cardin et al., Biochem. Biophys. Res. Com. 154:741 (1988), also called HBP1 below.

SEQ ID NO: 2. Peptide reacting with the heparin dimer of SEQ ID NO: 1, also called $(HBP1)_2$ below.

SEQ ID NO: 3. Peptide reacting with the heparin trimer of SEQ ID NO: 1, also called $(HBP1)_3$ below.

SEQ ID NO: 4. Peptide corresponding to the hypervariable area CD3 of the anti-DNA monoclonal murine antibody F4.1 (Avrameas et al., Proc. Natl. Acad. Sci. 95:5601 (1998)).

SEQ ID NO: 5 Peptide containing SEQ ID NO: 1 and SEQ ID NO: 4.

SEQ ID NO: 6. Peptide containing part of CDR2 and CDR3 regions of monoclonal murine antibody F4.1 (Avrameas et al., Proc. Natl. Acad. Sci. 95:5601 (1998)).

SEQ ID NO: 7. Peptide containing SEQ ID NO: 1 and SEQ ID NO: 6.

SEQ ID NO: 8. Peptide corresponding to the hypervariable CD3 region of human anti-DNA monoclonal antibody RTT79 (Stevenson et al., J. Autoimmunity 6:809 (1993)).

SEQ ID NO: 9. Peptide containing SEQ ID NO: 1 and SEQ ID NO: 8.

SEQ ID NO: 10. Peptide reacting with heparin and containing SEQ ID NO: 1 and the sequence of the peptide corresponding to the hypervariable area CDR3 of the human anti-DNA monoclonal antibody NE-1 (Hirabayashi et al., Scand. J. Immunol. 37:533 (1993)), also called No. 1047.

SEQ ID NO: 11. Peptide containing SEQ ID NO: 1 and the sequence of the peptide corresponding to the hypervariable area CDR3 of the human anti-DNA monoclonal antibody RT72 (Kalsi et al., Lupus 4:375 (1995)).

SEQ ID NO: 12. Peptide containing the sequence of the NLS (nuclear localization signal) of cells 3T3 and SEQ ID NO: 6.

SEQ ID NO: 13. Peptide containing SEQ ID NO: 1 and the sequence from CDR2 and CDR3 regions of the anti-DNA human monoclonal antibody NE-1.

SEQ ID NO: 14. Peptide containing part of CDR3 region of murine monoclonal antibody F4.1 and SEQ ID NO: 6.

SEQ ID NO: 15. Peptide containing twice the sequence of the peptide corresponding to the hypervariable CDR3 region of the anti-DNA human monoclonal antibody NE-1.

SEQ ID NO: 16. Peptide resulting from the inclusion, in position 13-19, of SEQ ID NO: 1 in SEQ ID NO: 15.

SEQ ID NO: 17. Peptide reacting with heparin derived from the amino acid sequence of the human lipoprotein E (Cardin et al., Biochem. Biophys. Res. Com. 154:741 (1988)), also called HBP4.

SEQ ID NO: 18. Peptide reacting with heparin derived from the amino acid sequence of agrine (Campanelli et al., Development 122:1663-1672 (1996)), protein of the extracellular matrix that regulates differentiation of the neuromuscular junction.

SEQ ID NO: 19. Dimer of SEQ ID NO: 18.

SEQ ID NO: 20. Peptide reacting with heparin derived from the amino acid sequence of insulin growth factor binding protein, also called HBP2 (Fowlkes et al., Endocrinol. 138:2280-2285 (1997)).

SEQ ID NO: 21. Peptide reacting with heparin and derived from the amino acid sequence of the C-terminal part of chain A of the platelet growth factor (Maher et al., Mol. Cell. Biol. 9:2251-2253 (1989)), also called HPB6.

SEQ ID NO: 22. Peptide containing 12 lysines (K) and SEQ ID NO: 6.

SEQ ID NO: 23. Peptide containing 12 lysines (K) and SEQ ID NO: 5.

SEQ ID NO: 24. Peptide having anti-microbial activity (Javadpour et al., J. Med. Chem. 39:3107-3113 (1996)).

SEQ ID NO: 25. Peptide reacting with heparin and corresponding to the sequence of the insulin-like growth factor-binding protein (Fowlkes et al., Endocrinol. 138:2280-2285 (1997)).

SEQ ID NO: 26. Peptide reacting with heparin and dimer of a peptide derived from the C-terminal part of the sequence of human dismutase superoxide (Inoue et al., FEBS 269:89-92 (1990)), also called (HBP3)$_2$.

SEQ ID NO: 27. Peptide reacting with heparin and corresponding to the sequence SEQ ID NO: 26 in which the amino acids are in configuration D.

SEQ ID NO: 28. Peptide reacting with heparin whose sequence is derived from SEQ ID NO: 26 and contains motif RGD selectively binding the αv integrins (21).

SEQ ID NO: 29. Peptide reacting with heparin and composed of peptides from SEQ ID NO: 1 and SEQ ID NO: 17, also called HBP1-HBP4 below.

SEQ ID NO: 30. Peptide reacting with heparin and derived from the C-terminal part of the sequence of the epidermal growth factor (EGF) (Arkonac et al., J. Biol. Chem. 273:4400-4405 (1998)), also called HBP7 below.

SEQ ID NO: 31. Peptide reacting with heparin and corresponding to the peptide whose sequence is SEQ ID NO: 12 where the amino acids are in front-back position.

SEQ ID NO: 32. Peptide reacting with heparin and corresponding to sequence SEQ ID NO: 30 in which the amino acids are in configuration D.

SEQ ID NO: 33. Peptide reacting with heparin and containing part of the sequence of the acid fibroblasts growth factor (aFGF) (Fromm et al., Arch. Biochem. Bioph. 343:92 (1997)), also called HBP8 below.

SEQ ID NO: 34. Peptide reacting with heparin and containing part of the sequence of the basic fibroblast growth factor (bFGF), also called HBP9 (Yayon et al., Cell 64:841-848 (1991)) below.

SEQ ID NO: 35. Peptide reacting with heparin and corresponding to a C-terminal part of the intestinal murine sequence (Gongqiao et al., Glyconjug J. 13:81-90 (1996)), also called HBP10 below.

SEQ ID NO: 36: Peptide reacting with heparin and containing part of the C-terminal sequence of human γ interferon (Lortat-Jacob & Grimaud, FEBS 280:152-154 (1991)), also called HBP11 below.

SEQ ID NO: 37: Peptide reacting with heparin and containing part of the sequence of subunit p40 of human interleukin 12 (Hasan et al., J. Immunol. 162:1064-1070 (1999)), also called HBP12 below.

SEQ ID NO: 38: Peptide reacting with heparin and containing part of the sequence of factor 1α derived from stromal cells (Amara et al., J. Biol. Chem. 272:200-204 (1999)), also called HBP13 below.

SEQ ID NO: 39: Peptide reacting with heparin and containing part of the sequence of the "heparin binding protein" (CAP 37) (Pohl et al., FEBS 272:200-204 (1990)), also called HBP15 below.

SEQ ID NO: 40: Peptide reacting with heparin corresponding to the peptide in sequence SEQ ID NO: 10 (1047) plus 13 N-terminal lysines.

SEQ ID NO: 41: Peptide reacting with heparin corresponding to the peptide in sequence SEQ ID NO: 28 (HBP3)2) plus 13 N-terminal lysines.

SEQ ID NO: 42: Peptide reacting with heparin corresponding to the peptide in sequence SEQ ID NO: 39 (HBP10) plus 13 N-terminal lysines.

SEQ ID NO: 43: Peptide with anti-microbial activity containing peptides in sequences SEQ ID NO: 10 (1047) and SEQ ID NO: 24.

SEQ ID NO: 44: Peptide with anti-microbial activity containing peptides in sequences SEQ ID NO: 24 and SEQ ID NO: 30 (HBP7).

SEQ ID NO: 45: Peptide with anti-microbial activity containing peptides in sequences SEQ ID NO: 24 and SEQ ID NO: 38 (HBP13).

SEQ ID NO: 46: Peptide containing the peptide in sequence SEQ ID NO: 26 (HBP3)$_2$ plus glycine-phthalcyl in N-terminal.

SEQ ID NO: 47: Peptide containing the peptide in sequence SEQ ID NO: 21 (HBP6) plus a salicylyl motif in N-terminal.

SEQ ID NO: 48: Peptide containing the peptide in sequence SEQ ID NO: 21 (HBP6) plus a salicylic motif in C-terminal.

Functionalized Peptides:

These peptides correspond to SEQ ID NO: 1 to 48 above, but carry, on the N-terminal side, either a cysteine that allows covalent coupling to some substances of interest (see below) or biotin allowing non-covalent combination of peptides with streptavidin or avidin conjugated with peroxidase (see points (1) and (2) below).

Example 2

Peptide Penetration Mechanism

Involvement of Glycosaminoglycans (GAG):

The peptides penetrate the cells by endocytosis mediated by the GAGs present on the membranes of all eukaryotic cells. Tests have been done to see their role in peptide penetration.

a) Heparin (50 μg/ml) was incubated with the cells for 1 hour before adding the peptide-peroxidase conjugates at 0.2 μg/ml for 2 hours. The cells were then lysed and the peroxidase dosed.

The 50 μg/ml of heparin totally inhibits the internalization of all peptides in cells H1299 and HeLa.

The quantity of heparin necessary to inhibit 50% penetration of the peptides coupled to peroxidase was evaluated with these two types of cells, by incubating the cells with the peptide-peroxidase conjugates with increasing concentrations of heparin. The results of inhibiting internalization of the peptides are expressed as the heparin concentration (μg/ml) in Table 2 below.

TABLE 2

|  | Peptide SEQ ID NO: 26 (HBP3)$_2$ | Peptide SEQ ID NO: 21 (HBP6) |
|---|---|---|
| 3T3 cells | 14.5μg/ml | 4.1 |
| HeLa cells | 8.5 | 2.3 |

These experiments demonstrate the role of the heparin sulfates in peptide penetration.

b) The CHO-745 cells are derived from CHO cells. They are deficient in xylosyl transferase, which helps in the formation of the chondroitin sulfate and heparin sulfate of the membrane. The peptide-avidin peroxidase complexes do not penetrate into the CHO-745 cells no matter which peptide was tested.

This shows the importance of the heparin sulfate chondroitins in the cell membrane in peptide penetration.

Involvement in Cell Metabolism:

To understand the biological mechanisms whereby the peptides penetrate into the cells and their compartmentalization, experiments are done with drugs whose action on certain cell compartments is specific. The peptide-peroxidases were incubated with H1299 cells at a concentration of 0.2 μg/ml for 2 hours in the presence, or not, of a drug. The cells were lysed, and the peroxidase dosed in the cellular lysate.

Table 3 below gives the percentage inhibition of peptide internalization calculated compared to the values given by the lysate of the cells incubated without the drug.

TABLE 3

|  | Peptide SEQ ID NO: 26 (HBP3)$_2$ | Peptide SEQ ID NO: 30 (HBP7) | Peptide SEQ ID NO: 35 (HBP10) |
|---|---|---|---|
| Temperature (4° C.) | 100 | 100 | 100 |
| Sodium azide (0.1%) | 70 | 70 | 50 |
| Sodium chloride (80 mM) | 51 | 69 | 27 |
| Ammonium chloride (50 mM) | 76 | 70 | 30 |
| Genistein (200 μM) | 59 | 68 | 70 |
| Chloroquin (100 μM) | 82 | 79 | 76 |

The penetration of the peptides tested is completely inhibited by incubating the cells at 4° C. with all peptides. It is partly inhibited by inhibitors of cell metabolism, like sodium azide (inhibitor of ATPase), genistein (inhibitor of tyrosine kinase and of the bond to ATP). The internalization mechanism is therefore dependent on the energy.

The penetration of peptides HBP3 and HBP7 is inhibited on the same order of magnitude by chloroquine, which reflects internalization in the same compartments of the cell cytoplasm (endosomal vesicles, endoplasmic reticulum), while sodium chloride and ammonium chloride (which prevent acidification of the endosomal vesicles, thus inhibiting intracellular traffic) is much less involved in internalization of the peptide in sequence SEQ ID NO: 35. This suggests that the peptides penetrate the cells by mechanisms similar to those used by different toxins, but without having toxicity. The intracellular routes up to the Golgi zone and the retrograde traffic seem distinct, depending on the peptides.

Example 3

Evaluation of the Capacity of the Peptides to React with DNA and Heparin

The capacity of peptides SEQ ID NO: 1 to 21 to attach themselves to DNA and heparin is evaluated on ELISA plates sensitized with DNA or heparin. Dilutions of biotinylated peptides are deposited on the plates and their fixation is shown using streptavidin conjugated with peroxidase. The activity of the peroxidase is revealed with orthodianisidine and $H_2O_2$ as a substrate. The avidity of each of the peptides for DNA or heparin is evaluated by the quantity ($\times 10^{-6}$ M) of peptides necessary to obtain 50% fixation. The results obtained are reported in Table 4 below.

TABLE 4

| SEQ ID NO | DNA | Heparin | Chondroitin A | Chondroitin B | Chondroitin C |
|---|---|---|---|---|---|
| 1 | >100 | >100 | >100 | >100 | >100 |
| 2 | 2.2 | 0.76 | 0.55 | 0.6 | 0.55 |
| 3 | 0.05 | 0.041 | 0.037 | 0.041 | 0.035 |
| 4 | 4 | 5 | 5.6 | 6.2 | 5 |
| 5 | 0.11 | 0.11 | 0.13 | 0.11 | 0.11 |
| 6 | 0.19 | 0.16 | 0.24 | 0.25 | 0.22 |
| 7 | 0.05 | 0.05 | 0.06 | 0.04 | 0.06 |
| 8 | >150 | >150 | >150 | >150 | >150 |
| 9 | 3.7 | 3.7 | 0.017 | 0.5 | >8 |
| 15 | 3 | >30 | 0.2 | 4 | 5 |
| 16 | 0.019 | 0.024 | 0.012 | 0.009 | 0.002 |
| 17 | >150 | >150 | >150 | >150 | >150 |
| 18 | >134 | >.134 | >134 | >134 | >134 |
| 19 | >74 | >74 | >74 | >74 | >74 |
| 20 | 0.09 | 0.07 | 0.06 | 0.04 | 0.1 |
| 21 | 0.2 | 0.07 | 0.12 | 0.12 | 0.12 |

This table shows that the affinity of SEQ ID NO: 1 for DNA is very small, while that of its dimer (SEQ ID NO: 2) and its trimer (SEQ ID NO: 3) is very great. It also appears that combining SEQ ID NO: 1 with peptic vectors substantially increases the affinity of those vectors for DNA (compare SEQ ID NO: 4 and 5, 6 and 7, 8 and 9, and 15 and 16). similarly, the affinity of SEQ ID NO: 17 and SEQ ID NO: 18 for DNA, heparin and the chondroitin sulfates is very small. On the other hand, the affinity for these molecules of the dimer of SEQ ID NO: 18 (SEQ ID NO: 19) is greater. SEQ ID NO: 20 and 21 contain a greater number of amino acids, among which a higher number of basic amino acids have a great affinity for DNA, heparin and the chondroitin sulfates.

The avidity of peptides SEQ ID NO: 25 to 39 for various proteoglycans (Kd$\times 10^{-9}$M), heparin and the chondroitin sulfates is evaluated by the quantity of peptides necessary to obtain 50% fixation on the different antigens. The results are reported in Table 5 below.

TABLE 5

| Peptides | Heparin | Chondroitin A | Chondroitin B | Chondroitin C |
|---|---|---|---|---|
| (HBP1)$_3$ | 41 | 37 | 41 | 35 |
| HBP2 | 70 | 60 | 40 | 100 |
| (HBP3)$_2$ | 20 | 51 | 43 | 6 |
| (HBP$_3$)2RGD | 407 | nt | nt | nt |
| HBP6 | 16 | 135 | 110 | 12 |
| HBP7 | 54 | 78 | 58 | 19 |
| HBP8 | 168 | 225 | 260 | 110 |
| HBP9 | 45 | 47 | 47 | 25 |
| HB010 | 78 | 112 | 229 | 39 |
| HBP11 | 382 | 287 | 301 | 205 |
| HBP12 | 295 | 176 | 173 | 93 |
| HBP13 | 56 | 56 | 38 | 16 |
| HBP15 | 100 | 100 | 100 | 100 |

This table shows that the avidity for heparin of peptides SEQ ID NO: 33 (HBP8), 36 (HBP11), and 37 (HBP12) is clearly smaller (>100×10$^{-9}$M) than that of the other peptides, which is on average between 20 and 80×10$^{-9}$M. The avidity of the different peptides with chondroitin sulfates A, B and C is, on the whole, on the same order of magnitude as that for heparin. Thus, the avidity of the peptides SEQ ID NO: 34 (HBP9) and SEQ ID NO: 38 (HBP13), for both heparin and the 3 chondroitins is 46-50×10$^{-9}$M, while that of peptides SEQ ID NO: 33 (HBP8), 36 (HBP11), and 37 (HBP12), for both heparin and the 3 chondroitins, is >100×10$^{-9}$M. The modified peptide SEQ ID NO: 28 ((HBP3)$_2$+RGD) lost its affinity for heparin.

Example 4

Evaluation of Penetration of Peptides Inside Cells

The cells are cultivated in the presence of the different peptides carrying, on the N-terminal side, biotin in decreasing concentrations (50 to 6 µg/ml) in the culture medium for variable times (1-18 hours).

At the end of the culture, the cells are washed three times with PBS (0.15 M NaCl buffered with 0.01 M potassium phosphate buffer pH 7.4) then fixed 15 minutes in ethanol at −20° C. The penetration of the peptide is evaluated after incubation for 30 minutes with streptavidin conjugated with peroxidase (abbreviated S-PO for streptavidin-peroxidase). Then, the S-PO is eliminated, and the cells are washed. The activity of the peroxidase internalized is revealed by diaminobenzidine in the presence of H$_2$O$_2$ and the cells are examined under a microscope (Ternynck & Avrameas, Editions INSERM (1987)). The microscopic examination showed that some of the peptides used (SEQ ID NO: 1, 4, 11, 12, 17 and 18) do not give any positive intracellular cytochemical coloration. With the other peptides, positive colorations, but of variable intensity, were noted. Faint coloration was observed with SEQ ID NO: 2, 6, 8 and 19, while, intensive colorations were obtained with the other peptides.

It is interesting to note that all peptides that contain SEQ ID NO: 1, that is HBP of human lipoprotein B, give a positive coloration except for SEQ ID NO: 1 itself (monomer) and SEQ ID NO: 11.

As far as SEQ ID NO: 1, 17 and 18 are concerned, they are short peptides that correspond to the HBP of human lipoproteins B and E and agrine. Unlike those monomer peptides, their dimers (SEQ ID NO: 2) and especially the trimer of SEQ ID NO: 3) give clearly positive colorations.

As for SEQ ID NO: 11, it is composed of SEQ ID NO: 1 and CDR3 of anti-DNA human monoclonal antibody RT72 (coded by the germinal line), which contains only one basic amino acid (K). Unlike SEQ ID NO: 11, SEQ ID NO: 5, 7, 9 and 10, which are composed of SEQ ID NO: 1 and CDR2 and/or CDR3 of anti-DNA monoclonal antibodies (coded by the germinal line), contain a high number of basic amino acids and give intense coloration.

On one hand, these results suggest that a minimum of 3 to 5 excess basic amino acids must be present in the peptide sequence so that the peptide is able to penetrate inside the cells. On the other hand, SEQ ID NO: 1 is capable of increasing the translocation power of anti-DNA CDR2 and/or CDR3 only when the latter have a high number of basic amino acids. The microscopic examination showed that all peptides SEQ ID NO: 25 to 48 give positive cytochemical coloration at a concentration of 6 µg/ml, although the intensity can vary depending on the peptides.

Example 5

Evaluation of Penetration into Cells of Peptide/Streptavidin or Peptide/Avidin Complexes Coupled to Peroxidase or Peptide/Peroxidase Conjugates A biotinylated/S-PO peptide or biotinylated/A-PO complex (A-PO for avidin-peroxidase) is prepared extemporaneously in two ways:

1) either in a peptide: S-PO or A-PO molar ratio of 4:1 (for example, 1.4 µg of peptide with a molecular weight of 3500 to 10 µg of S-PO; the weight of S-PO used varies depending on the peptides since their molecular weights are different).

2) or in a peptide: S-PO or A-PO molar ratio of 25:1 (for example 1.7 µg of peptide with a molecular weight of 3500 to 1 µg of S-PO).

The complexes are prepared by incubating the biotinylated peptide with S-PO or A-PO in PBS in a volume of 5 to 10 µl for 15 minutes at laboratory temperature. They are then diluted in 1 ml of complete culture medium, filtered on a 0.2 micron membrane and incubated with the cells for 4 hours. The cells are then washed three times with PBS.

To study the penetration of the complexes under a microscope, the cells are fixed as before for 15 minutes in ethanol at −20° C., they are washed with PBS, and the activity of the internalized peroxidase is shown by diaminobenzidine in the presence of H$_2$O$_2$. To measure the quantity of peptide/S-PO or A-PO complexes internalized, the cells are trypsinized, transferred into microtubes and counted. They are washed twice by centrifugation, then the residue is suspended in 200 µl of lysis buffer (Tris buffer, 0.1 M, pH8, 0.5% Nonidet). After 15 minutes, the peroxidase contained in the lysis buffer is dosed onto 96-well plates with ortho-dianisidine and H$_2$O$_2$ by comparison with a standard curve for S-PO. The reading is taken at 450 nm. The quantity contained in the different samples is expressed in picograms (pg) per 10$^4$ cells.

Generally, the results obtained by examining the cells under an optic microscope correlate well with the results obtained by measuring the internalized peroxidase. That is the reason that, in what follows, only the quantitative results obtained with a certain number of peptides are given in Table 6 and 7 and FIGS. 1 to 3.

Table 6 shows an evaluation of the capacity of peptides composed of different HBPs from varied proteins to penetrate H1299 cells, using peptide: S-PO complexes of 4:1 and a peptide concentration of 1 µg.

TABLE 6

| | H1299 Cells (pg/10⁴ cells) |
|---|---|
| SEQ ID NO: 1 | 3 |
| SEQ ID NO: 2 | 84 |
| SEQ ID NO: 3 | 642 |
| SEQ ID NO: 17 | 3 |
| SEQ ID NO: 18 | 3 |
| SEQ ID NO: 19 | 167 |
| SEQ ID NO: 20 | 431 |
| SEQ ID NO: 21 | 1680 |

The results clearly show that for a vector to be effective in intracellular transfer of the complex S-PO (MW=100,000), a minimum of 6 basic amino acids must be present (SEQ ID NO: 2, 3, 19-21).

Table 7 below reports the results of evaluating the influence of SEQ ID NO: 1 on the penetration of peptides coupled to SEQ ID NO: 1 into H1299 cells, where Concentration a: 25 peptides to one molecule of S-PO (1 µg), Concentration b: 4 peptides to one molecule of S-PO (10 µg).

TABLE 7

| PEPTIDES NOT INCLUDING SEQ ID NO: 1 (pg/10⁴ cells) | | PEPTIDES INCLUDING SEQ ID NO: 1 (pg/10⁴ cells) | |
|---|---|---|---|
| SEQ ID NO: 4 | | SEQ ID NO: 5 | |
| Conc. a | 2 | Conc. a | 100 |
| Conc. b | 280 | Conc. b | 6250 |
| SEQ ID NO: 6 | | SEQ ID NO: 7 | |
| Conc. a | 1 | Conc. a | 240 |
| Conc. b | 130 | Conc. b | 220 |
| SEQ ID NO: 8 | | SEQ ID NO: 9 | |
| Conc. a | 50 | Conc. a | 340 |
| Conc. b | 1310 | Conc. b | 8280 |
| SEQ ID NO: 15 | | SEQ ID NO: 16 | |
| Conc. a | 250 | Conc. a | 430 |
| Conc. b | 6670 | Conc. b | 5220 |

Table 7 shows that coupling SEQ ID NO: 1 with peptide vectors from anti-DNA human or murine antibodies substantially potentiates the translocation power of those vectors.

FIG. 1 is a bar graph illustrating the internalization of streptavidin-peroxidase transported by various biotinylated peptides one night at 37° C. at concentration a (0.5 nmole of biotinylated peptide to 0.02 nmole of streptavidin-peroxidase).

As can be seen from FIG. 1, coupling SEQ ID NO: 1 with a given vector (SEQ ID NO: 6), which opens onto SEQ ID NO: 7, significantly increases the transfer capacity of the vector. However, coupling a peptide the same length as SEQ ID NO: 1 whose composition of amino acids is close, with this same vector, which opens onto SEQ ID NO: 12, barely increases the translocation power of the vector. Even coupling a second CDR3 identical to the SEQ ID NO: 6, which opens onto SEQ ID NO: 14, does not result in as sharp an increase as coupling it with SEQ ID NO: 1. Generally, the combination of SEQ ID NO: 1 with vectors of human (SEQ ID NO: 10 and 13) or murine (SEQ ID NO: 5) origin produces particularly effective vectors.

Figure 2:
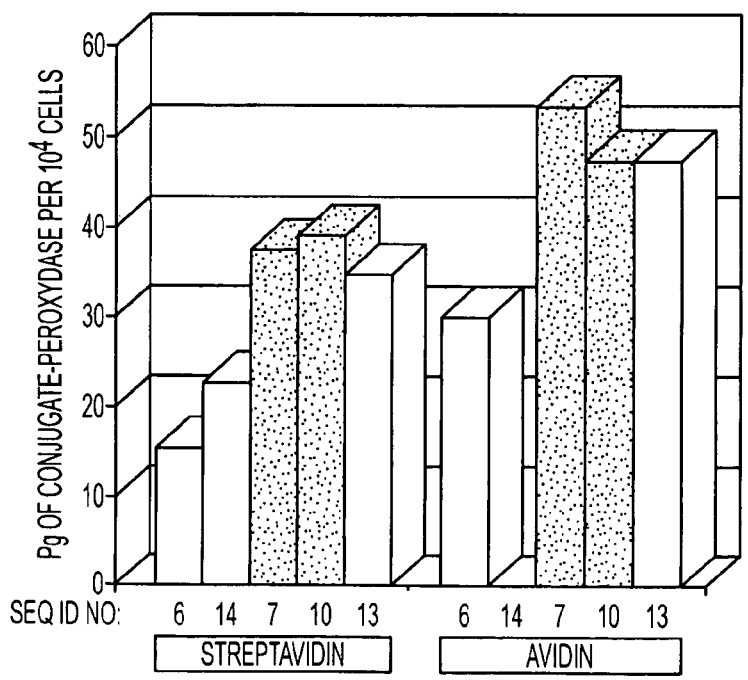
FIG. 2 is a bar graph comparing the internalization of S-PO and A-PO transported by various biotinylated peptides.

FIG. 2 is a bar graph illustrating the internalization of streptavidin-peroxidase (S-PO) and avidin-peroxidase (A-PO) transported by various biotinylated peptides (2 hours at 37° C.) at concentration b (0.25 nmole of biotinylated peptides to 0.01 nmole of S-PO or A-PO).

Figure 3:
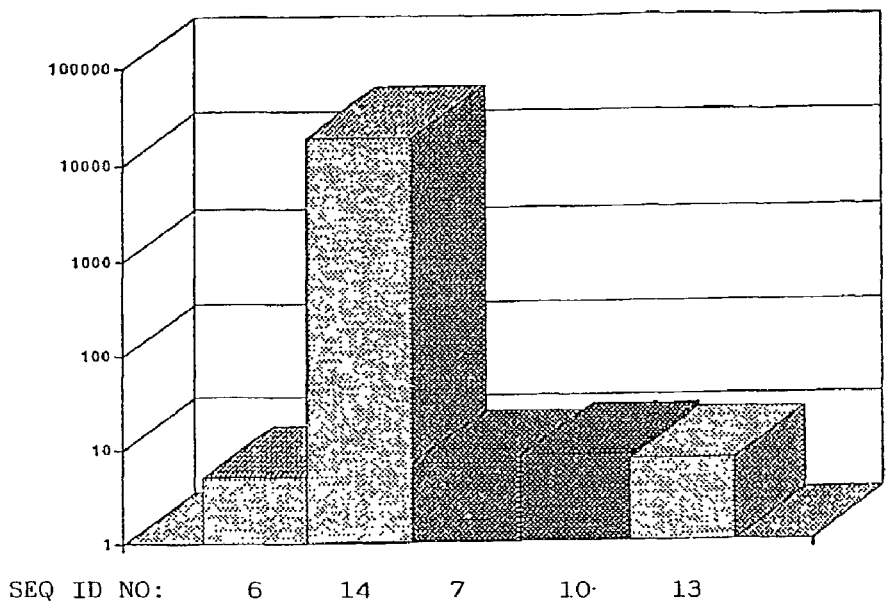
FIG. 3 is a bar graph illustrating the ratio between internalization of S-PO and internalization of A-PO by the biotinylated peptides (S-PO/A-PO).

FIG. 3 is a bar graph illustrating the ratio between the internalization of S-PO and that of A-PO by those same biotinylated peptides, 2 hours at 37° C., at concentration b (0.25 nmole of biotinylated peptide to 0.01 nmole of S-PO or A-PO).

The comparison in FIGS. 2 and 3 of the transfer of S-PO and A-PO by the vectors suggests that the nature of the substances being transferred influences the translocation capacity of the original all-murine vectors (SEQ ID NO: 14) more than that of the vectors containing HBP of human origin (SEQ ID NO: 7, 10 and 13).

Figure 4:
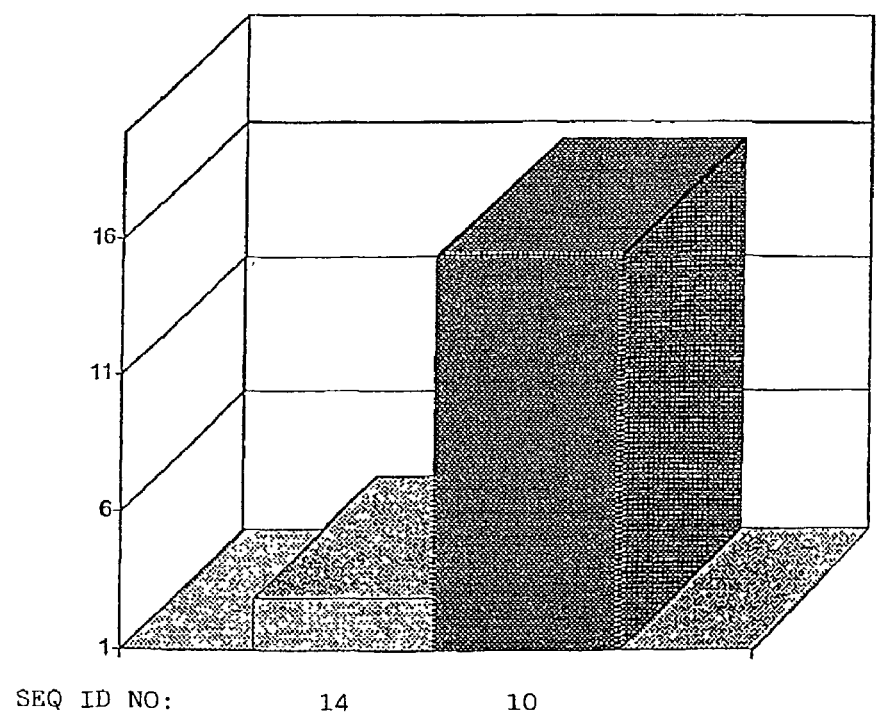
FIG. 4 is a bar graph illustrating the ratio between internalization of S-PO at 37° C. for 2 hours and at 4° C. for 2 hours by a biotinylated peptide of human origin (peptide 10) and one of murine origin (peptide 14).

FIG. 4 is a bar graph illustrating the relationship between the internalization of S-PO transported by two biotinylated peptides at 37° C. for 2 hours and at 4° C. for 2 hours. The results obtained indicate that the translocation power of the vector of human origin (SEQ ID NO: 10) is much more dependent on the temperature (active cell metabolism) than that of the vector of murine origin (SEQ ID NO: 14).

To evaluate more directly the penetration of the peptides, avoiding the avidin-peroxidase bias, some of the peptides in sequences SEQ ID NO: 25 to 48 were conjugated covalently with cysteine in the C-terminal position of the peptide to peroxidase. The peptides were coupled with peroxidase in the following way:

One mg of peroxidase activated with maleimide (Sigma) in 100 µl of sodium phosphate buffer, NaCl 0.15 M, EDTA 5 mM, had 1 mg of peptide added to it. After 2 hours at laboratory temperature, β-mercaptoethanol is added to a final concentration of 1.5 mM for 15 minutes. The uncoupled peptide is eliminated by centrifugation on ultrafiltration membranes (cut-off threshold=30,000 Daltons, Sartorius), followed by three washings in sodium phosphate buffer 0.1 M, pH 7.4 containing 0.15 M NaCl.

The H1299 cells are incubated for 2 hours with the conjugates at increasing concentrations of peptide-peroxidase in the culture medium, then washed with PBS. The cells are lysed and the quantity of peptide internalized is evaluated by the dosage of peroxidase in the lysate of the cells with reference to a curve established with peptide-peroxidase.

The quantity of peptide internalized (pg/10³ cells), depending on the concentrations of conjugates in the culture medium, is shown in Table 8 below.

TABLE 8

| | Concentration (µg/ml) | | | |
|---|---|---|---|---|
| | 0.01 | 0.1 | 0.5 | 1 |
| Peptide SEQ ID NO: 28 | 0.006 (0.006)* | 1.7 (1.6) | 37.9 (7.6) | 8860 (8.8) |
| Peptide SEQ ID NO: 34 | 0.002 (0.01) | 1.4 (1.4) | 40.7 (8.14) | 109 (10.9) |

*percentage of quantity of peroxidase internalized compared to quantity deposited.

It appears that the higher the concentration of peptide-peroxidase conjugate in the culture medium, the more the quantity internalized increases. To compare the penetration of the conjugates by cell type, the cells from different lines were incubated with 0.2 µg/ml of peptide-peroxidase conjugate for 2 hours, and the quantity of peroxidase dosed in the lysates. Table 9 and Table 9B below give the results expressed in pg/10³ cells. The quantity of each peptide internalized in the different lines generally varies only from single to double.

The internalization of peptides (HBP3)₂ (SEQ ID NO: 26) and HBP7 in configuration D (SEQ ID NO: 32) is on the same order of magnitude as that of the homologous peptides in configuration L. The same is true of the peptide in SEQ ID NO: 30 and its homolog in SEQ ID NO: 31, which has an amino acid sequence in the reverse position.

TABLE 9

Internalization of Peptide-peroxidase (pg/$10^3$ cells)

| Peptides | Cell Lines | | |
|---|---|---|---|
| | 3T3 | H1299 | HeLa |
| 1047 | 35 | 10 | 4.7 |
| (HBP1)$_3$ | 24.6 | 17.7 | 11.2 |
| (HBP3)$_2$ | 41 | 27.8 | 14.9 |
| HBP6 | 83.7 | 21.9 | 13.2 |
| HBP7 | 48.8 | 22.5 | 11 |
| HBP8* | 7.6 | 3.6 | 2.1 |
| HBP9* | 9 | 3.8 | 3.4 |
| HBP10 | 23.3 | 7.9 | 5.3 |
| HBP11 | 20.3 | 10.6 | 4.4 |
| HBP12* | 5.7 | 4.3 | 2.5 |
| HBP13 | 18.1 | 9.1 | 4.1 |

TABLE 9B

Internalization of peptide-peroxidase (pg/$10^3$ cells)

| Peptides | Cell Lines | | |
|---|---|---|---|
| | 3T3 | H1299 | HeLa |
| (HBP3)$_2$ | 72.9 | 67.4 | 11.4 |
| (HBP3)$_2$ D-configuration | 63.7 | 59.1 | 4.1 |
| HBP7 | 44.2 | 63.3 | 3.6 |
| HBP7 D-configuration | 50 | 56.7 | 7.7 |
| HBP7 front/back | 75.9 | 70.6 | 8.7 |

*at the limit of the dosage method and consequently significant.

Example 6

Evaluation of Penetration of Peptide-IgG Conjugates in Cells

Two mg of monoclonal IgG antibody or its fragment F(ab')2 in 1 ml of sodium phosphate buffer 0.1M, pH 7 containing 0.15 M NaCl are added to 200 µg of SMCC [succinimidyl 4-(N-maleimidomethyl)cyclohexane-1-carboxylate] in 10 µl of dimethylsulfoxide, and the solution is incubated for 30 minutes at laboratory temperature. The excess reagent is eliminated by centrifugation on ultrafiltration membranes [cutoff threshold=10,000 Daltons (Da), Vivascience], followed by three washings in sodium phosphate buffer 0.1 M, pH 7 containing 0.15 M of NaCl.

The peptide is then coupled in a molar ratio of 6 peptides to 1 IgG in sodium phosphate buffer, 0.1M, pH7, containing 0.15M NaCl for 3 hours at laboratory temperature. Then, the excess uncoupled peptide is eliminated by centrifugation on membranes, as in the preceding step.

To evaluate the penetration of the conjugates under a microscope, the cells are cultivated in the presence of the different antibody-peptide conjugates at decreasing concentrations (50 to 6 µg/ml) in the culture medium for 4 hours at 37° C. At the end of the culture, the cells are washed three times with PBS, then fixed for 15 minutes in ethanol at −20° C. The penetration of the IgG-peptide conjugate is evaluated after incubation for 1 hour with an anti-IgG mouse antibody coupled with peroxidase. The cells are then washed with PBS, and the activity of the peroxidase is revealed by diaminobenzidine in the presence of $H_2O_2$.

To measure the quantity of peptide-IgG conjugates internalized, the cells are trypsinized, transferred into microtubes and counted. They are washed twice by centrifugation, then the residue is suspended in 200 µl of lysis buffer (TRIS buffer, 0.1M, pH8, 0.5% Nonidet 40). The quantity of mouse IgG present in the lysate is measured by ELISA on plates coated with mouse anti-IgG sheep antibody and revealed by a mouse anti-IgG sheep antibody conjugate coupled with peroxidase, with reference to a standard curve established with the same monoclonal antibody that was conjugated with the peptide. The results are compiled in Table 10, which reports the penetration of murine monoclonal antibodies or their fragments F(ab')2 inside human H1299 cells, where:

a: specific murine monoclonal antibody of protein p53, and
b: specific murine monoclonal antibody of protein p21 from a rat-rat hybridoma.

TABLE 10

| Quantity of antibodies internalized | Conjugate SEQ ID NO: 10 IgG[b] | Conjugate SEQ ID NO: 10 F(ab')$_2$[b] | Conjugate SEQ ID NO: 10 F(ab')$_2$[a] |
|---|---|---|---|
| pg/$10^4$ cells | 137 | 620 | 383 |

As can be seen from the table, using vectors of human origin combined with SEQ ID NO: 1 permits effective internalization of the antibody into human cells. Note also that greater quantities of antibodies are transferred into the cells when the vectors are conjugated with F(ab')$_2$ rather than with the whole antibody.

Figure 5:
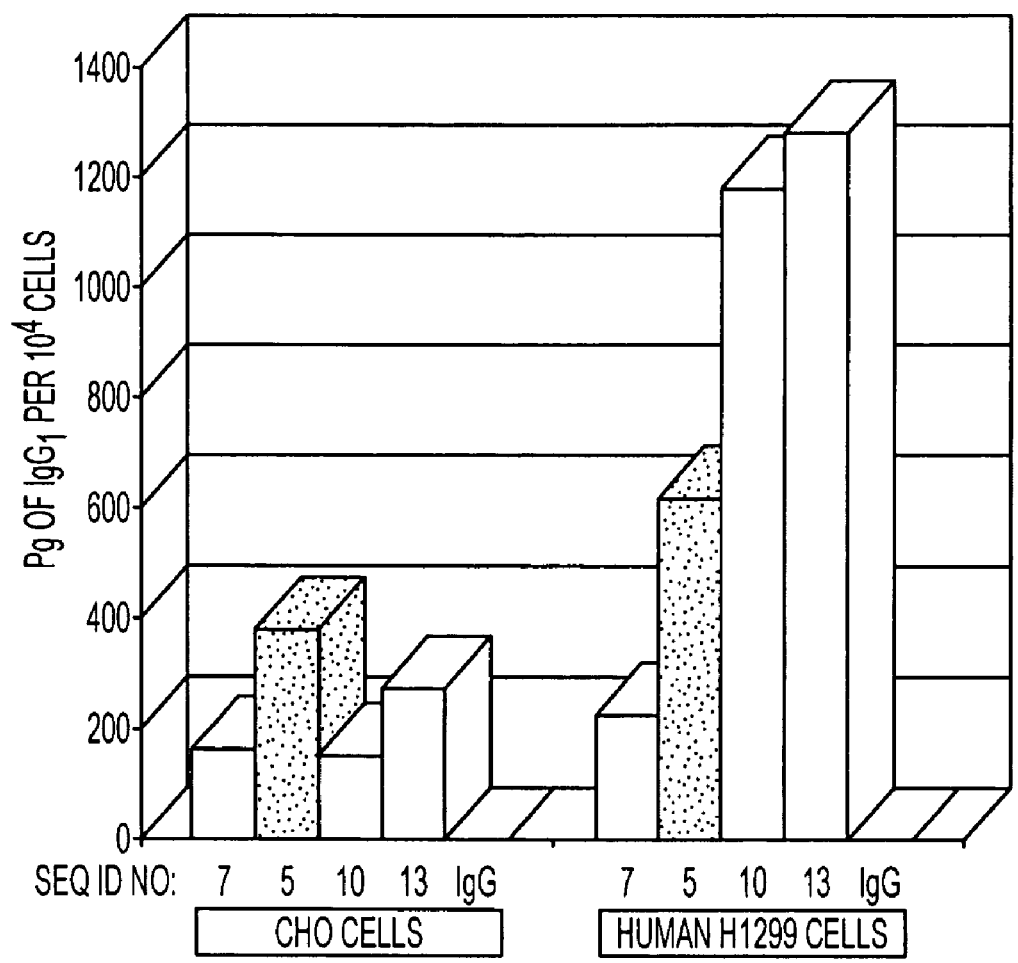
FIG. 5 is a bar graph illustrating the internalization into H1299 human cells and Chinese hamster ovary cells (CHO)of murine monoclonal IgG$_1$ coupled with different peptides.

FIG. 5 is a bar graph illustrating the internalization of a murine monoclonal antibody IgG$_1$ coupled with different peptides (4 hours at 37° C.; 30 µg/ml of conjugate deposited) on human H1299 cells and hamster ovary cells CHO.

As can be seen from this graph, the vectors of human origin (SEQ ID NO: 10 and 13) are more effective in transferring substances inside human cells than vectors of murine origin coupled to SEQ ID NO: 1 (SEQ ID NO: 7 and 5). The vectors of human origin (SEQ ID NO: 10 and 13) are also more effective in transferring substances inside human cells than inside hamster cells.

Example 7

Evaluation of Intracellular Penetration Capacities of Recombinant Proteins by Immunofluorescence HeLa cells are sown in a concentration of 0.5×$10^4$ cells on a plate with 24 wells, each containing a sterile lamella. 24 hours later, 50 µg/ml of recombinant protein is deposited on the cells. Six or eighteen hours after that, the cells are washed twice in PBS (phosphate-buffered saline) and fixed with a 4% PFA (paraformaldehyde) solution in PBS for 10 minutes at ambient temperature or dissociated with trypsin and cultured 18 hours on a lamella and then fixed. After three washings in PBS, the cells are permeabilized with a 0.25% solution of TritonX-100 in PBS for 5 minutes at ambient temperature. After three 5-minute washings in PBS, the cells are incubated for 1 hour at ambient temperature in a moist room with the monoclonal antibody anti-RGS.His (Qiagen) diluted to 1/50 in PBS 0.1% BSA (bovine serum albumin). After three 10-minute washings with PBS, the lamella are incubated for 30 minutes at ambient temperature in a moist room with conjugated goat anti-mouse IgG/FITC diluted to 1/200 in PBS-0.1% BSA. The cells are washed twice in PBS for 10 minutes, then the lamella are mounted on a blade with some mounting liquid (Mounting Medium from Sigma). The cells are observed under a confocal microscope (Leica).

Figure 17:
FIG. 17A-B shows immunofluorescence of Hela cells incubated with $His_6$-PAV1.
Figure 17:
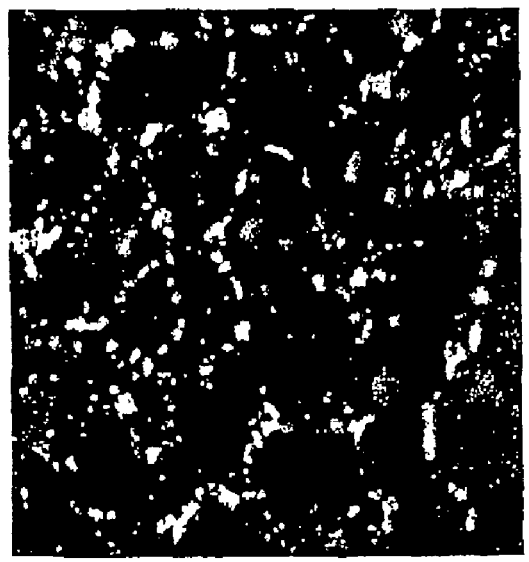
Figure 18:
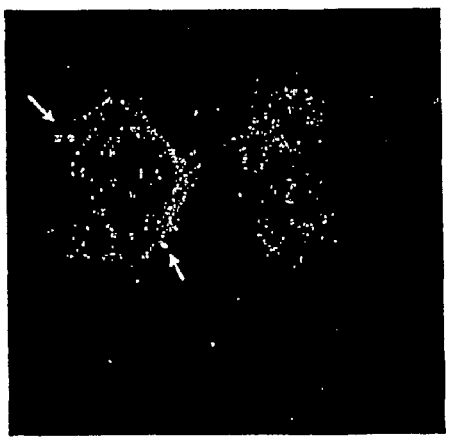
FIG. 18A-C shows immunofluorescence of Hela cells incubated with $His_6$-Zebra☐nls-PAV1.
Figure 18:
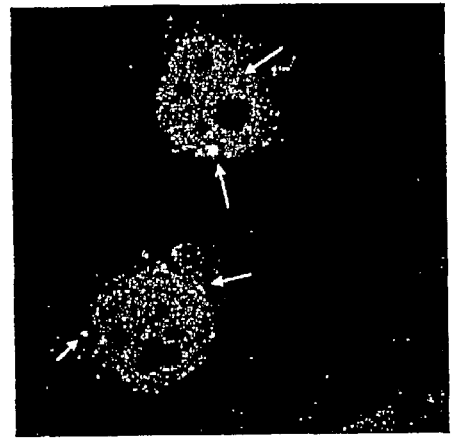
Figure 18:

The HeLa cells are incubated 18 hours with recombinant protein His$_6$-PAV1 and fixed (FIG. 17A) or dissociated and cultured 18 hours before fixation (FIG. 17B). Observation of the cells under the confocal microscope shows that the cells incubated 18 hours have major fluorescence on their surface. No intracellular fluorescence seems to be detected in this experiment. However, contra-coloration of the nuclei by DAPI or HOECHST would make it possible to confirm it. It cannot be ruled out that a small proportion of protein is internalized. It also appears that a single PAV1 peptide motif is sufficient to address a recombinant protein on the surface of the cells. After dissociation of the cells, the fluorescence localizes in some endosomal vesicles of different sizes. The recombinant protein His$_6$-Zebra-PAV1 is internalized, but does not seem to be nuclear despite the nls domain of the Zebra protein. The HeLa cells are incubated for 6 or 18 hours with the recombinant protein His$_6$-ZebraΔnls-PAV1 and fixed (FIGS. 18A and 18B) or dissociated after 18 hours and cultured 18 hours before fixation (FIG. 18C). After 6 hours, a nuclear fluorescence is observed that is accentuated at 18 hours. Nuclear areas indicated by arrows have greater fluorescence. For the dissociated cells, more marked fluorescence is located around the nucleoli. Contrary to recombinant protein His$_6$-Zebra-PAV1, recombinant protein His$_6$-ZebraΔnls-PAV1 deprived of the nls domain has a nuclear localization. Sequence PAV1 seems to address the protein in the nucleus.

For the HeLa control cells (without protein) or the Hela cells incubated with the recombinant proteins His$_6$-Zebra and His$_6$-ZebraΔnls, no fluorescence was observed.

Example 8

In Vitro Evaluation of Cytotoxic Activity of Ribonuclease A (RNase A) Conjugated with Peptides 5 mg of bovine RNase A is dissolved in 1 ml of sodium phosphate buffer 0.1M, pH 7 containing 0.15 NaCl.

1 mg of SMCC is dissolved in 50 μl of dimethylsulfoxide (final solution 20 mg/ml).

The RNase A is activated by adding 12.5 μl of SMCC solution into 200 μl of RNase A solution (molar ratio=10 molecules of SMCC to 1 molecule of RNase A).

The reaction takes 30 minutes at laboratory temperature.

The excess reagent is eliminated by centrifugation on ultra-filtration membranes (cutoff threshold=5,000 Da, Vivascience) followed by 3 washings with sodium phosphate buffer 0.1 M containing 0.15 M NaCl.

Figure 6:
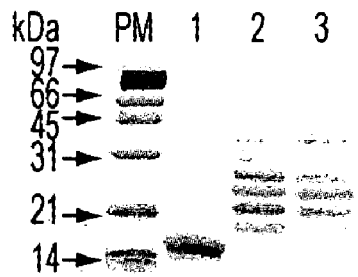
FIG. 6 is a gel comparing RNase A alone (lane 1) to RNase A coupled with SEQ ID NO: 10: human Cyst-HBP-CDR3 (lane 2) and human HBP-CDR3-Cyst (lane 3). PM indicates size markers.

The peptide is then coupled in a 6:1 molar ratio of peptide:RNase A in sodium phosphate buffer 0.1 M, pH 7, containing 0.15 M NaCl for 3 hours at ambient temperature. The excess uncoupled peptide is eliminated by centrifugation as in the preceding step. The quantity of peptide coupled to RNase A is evaluated by the molecular weight of the bands obtained after coupling on an SDS-polyacrylamide gel made of 15% acrylamide. The results of electrophoresis comparing RNase A alone (band 1) to RNase A coupled with SEQ ID NO: 10 are shown in FIG. 6, where two coupling tests are presented (bands 2 and 3).

Figure 7:
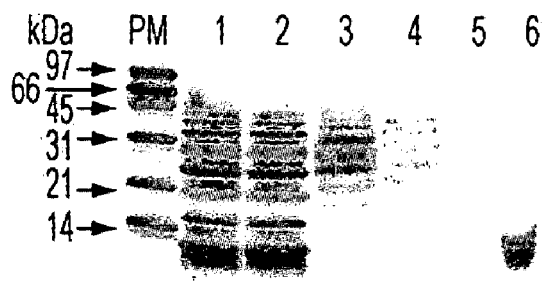
FIG. 7 is a gel comparing RNase A coupled to peptide 16, mouse P3CDR3 (lanes 1 & 2); RNase A coupled to peptide 5, mouse HBP-CDR3 (lane 3); RNase A coupled to peptide 10, human HBP-CDR3 (lane 4); RNase A alone (lane 5); and peptide 16 (SEQ ID NO: 14, mouse P3CDR3) alone (lane 6). PM indicates size markers.

FIG. 7 shows the results of electrophoresis, used in the same way, to compare the migration of RNase A alone (band 5) and that of SEQ ID NO: 14 alone (band 6) with that of the product of coupling RNase A with SEQ ID NO: 14 (two tests: bands 1 and 2), with SEQ ID NO: 5 (band 3) and with SEQ ID NO: 10 (band 4).

RNase A coupled with vectors of human origin (SEQ ID NO: 10, 15 and 16) were tested for its cytotoxic activity on HH9 cells in culture by comparison with natural RNase A.

Example 9

In Vitro Evaluation of Cytotoxic Activity of RNase on HH9 cells

The cells are sown at night on plates with 96 wells, at the rate of $10^3$ cells per well.

The next day, the supernatant is suctioned off and replaced with 100 μl of medium containing succession dilutions of RNase A-vector or natural RNase A and the culture continued for 72 hours.

The wells are then filled with 50 μl of a solution of MTT (3-(4,5-dimethylthiazol-2-yl)-2,5-diphenyl tetrazolium bromide) at 1 mg/ml in the culture medium and cultivated for 4 hours.

The supernatant is removed, and 100 μl of dimethylsulfoxide is added to the wells. After the crystals dissolve, the coloration is read at 550 nm.

The results are calculated as a percentage of the average optic density obtained in the wells of cells containing the dilutions of the samples being tested and the optical density of the wells that received only medium. These results are shown graphically in FIG. 8.

Figure 8:
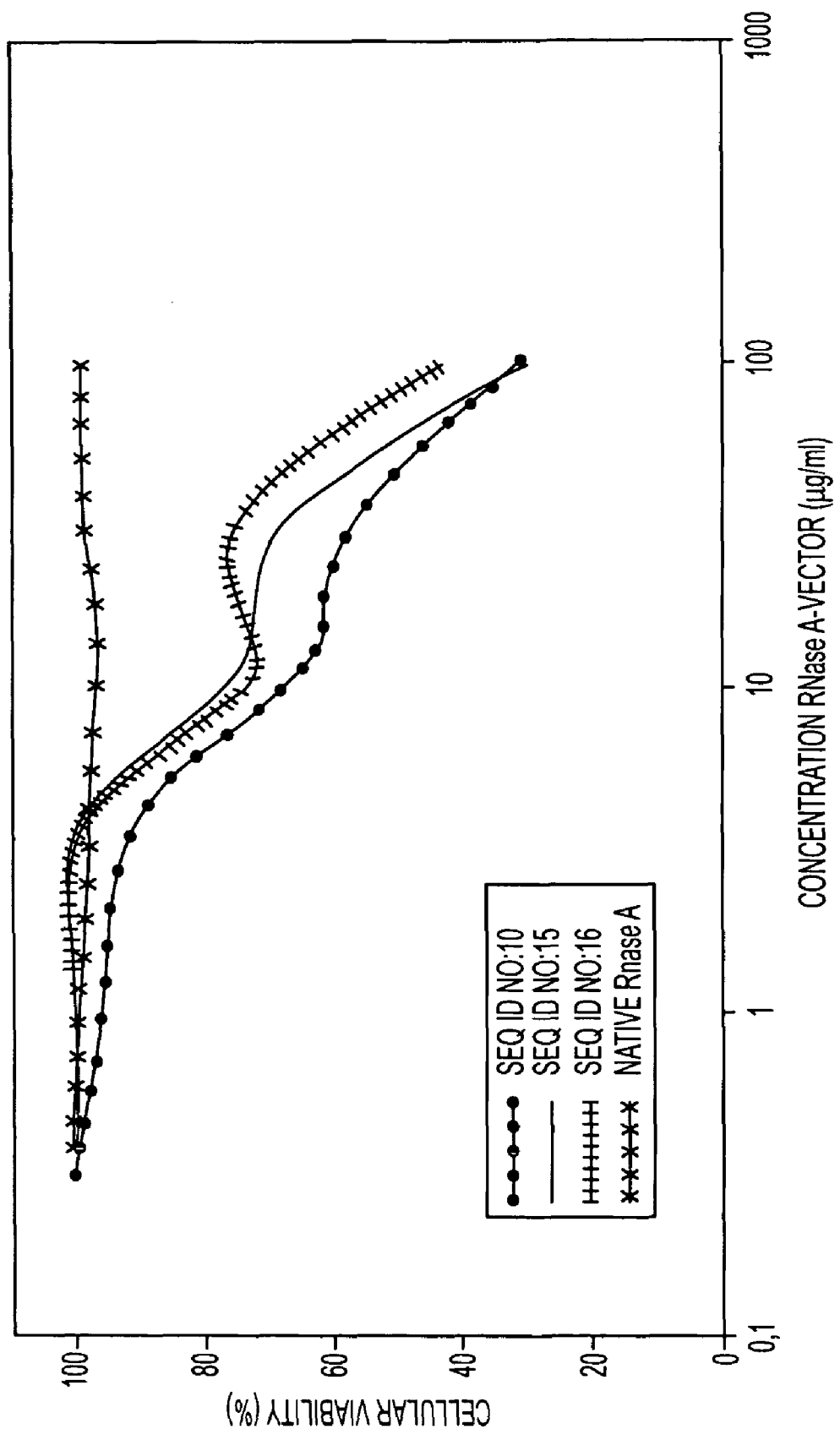
FIG. 8 is a graph of the cytotoxic effects of peptide-RNase A conjugates at various concentrations of conjugate added to HH9 cell culture.

As can be seen from FIG. 8, natural RNase A has no cytotoxic activity. The average cytotoxicity of 50% is obtained at concentrations of RNase A-vector between 33 and 100 μg/ml, i.e., between the molar concentrations of 2 to $7 \times 10^{-7}$M.

Example 10

In vitro Evaluation of Cytotoxic Activity of Peptide-RNase Conjugates on HeLa cells The different peptide-RNase conjugates were tested on varied cell lines. The results are expressed as IC50, which corresponds to the concentration of the peptide-RNase conjugate giving 50% inhibition of cell growth after 72 hours of culture. Table 11 summarizes the results obtained. It appears that all the conjugates have distinct cytotoxic activities and that some of them have little cytotoxic power.

TABLE 11

| Peptide-RNase | Cell Lines | | | | | | | |
|---|---|---|---|---|---|---|---|---|
| | HT29 | H1299 | HH9 | HUVEC | 3T3 | MCF7 | HeLa | B16.F10 |
| (HBP1)$_3$- | 70 | 100 | 20 | 80 | 40 | 90 | 60 | 25 |
| (HBP1)$_2$- | nt* | 25 | nt | nt | nt | nt | nt | nt |
| HBP1-4- | nt | 25 | nt | nt | nt | nt | 6 | nt |
| HBP3- | 10 | 12 | 2 | 15 | 3 | 15 | 7 | 12 |
| HBP6- | 45 | 3 | 3 | 50 | 3 | 20 | 12 | nt |

TABLE 11-continued

| Peptide-RNase | Cell Lines | | | | | | | |
|---|---|---|---|---|---|---|---|---|
| | HT29 | H1299 | HH9 | HUVEC | 3T3 | MCF7 | HeLa | B16.F10 |
| HBP7- | 45 | 50 | 2 | 50 | 6 | 25 | 15 | nt |
| HBP8- | nt | nt | nt | nt | nt | nt | >100 | nt |
| HBP9- | nt | nt | 100 | nt | nt | nt | >100 | nt |
| HBP10- | >100 | 150 | 33 | >100 | 50 | 150 | 25 | nt |
| HBP11- | >100 | >100 | 60 | >100 | 60 | >100 | 20 | nt |
| HBP12- | >100 | >100 | >100 | >100 | 40 | >100 | >100 | nt |
| HBP13- | 40 | 100 | 8 | 65 | 14 | >100 | 3 | nt |
| HBP14- | >100 | 250 | >100 | >100 | 55 | 90 | 25 | nt |
| 1047- | >100 | 250 | 60 | >100 | 55 | 90 | 30 | >100 |

*nt: not tested

Example 11

In vivo Evaluation of Cytotoxic Activity of RNase A Conjugated with Peptides on Human Tumors Grafted onto Athymic (nude) Mice Protocol 1:

Female nude mice 6 weeks old were injected subcutaneously with $3\times10^6$ HH9 cells, volume 50 µl, in the left side. On day 17 after the transplant, the tumors were measured, and the mice were divided into 3 groups: Group 1 (7 mice) injected with 100 µg of a coupling SEQ ID NO: 10/RNase A in 50 µl of PBS, Group 2 (7 mice) injected with 50 µg of natural RNase A in 100 µl of PBS, Group 3 (6 mice) injected with 50 µl of PBS. The injections were given three times a week under the same conditions. Each time, the tumors were measured, and their volume was calculated using the formula $V=4/3\pi \times L^2 1$ (L>1) where L is for the large diameter of the tumor and 1 for the small diameter of the tumor.

Figure 9:
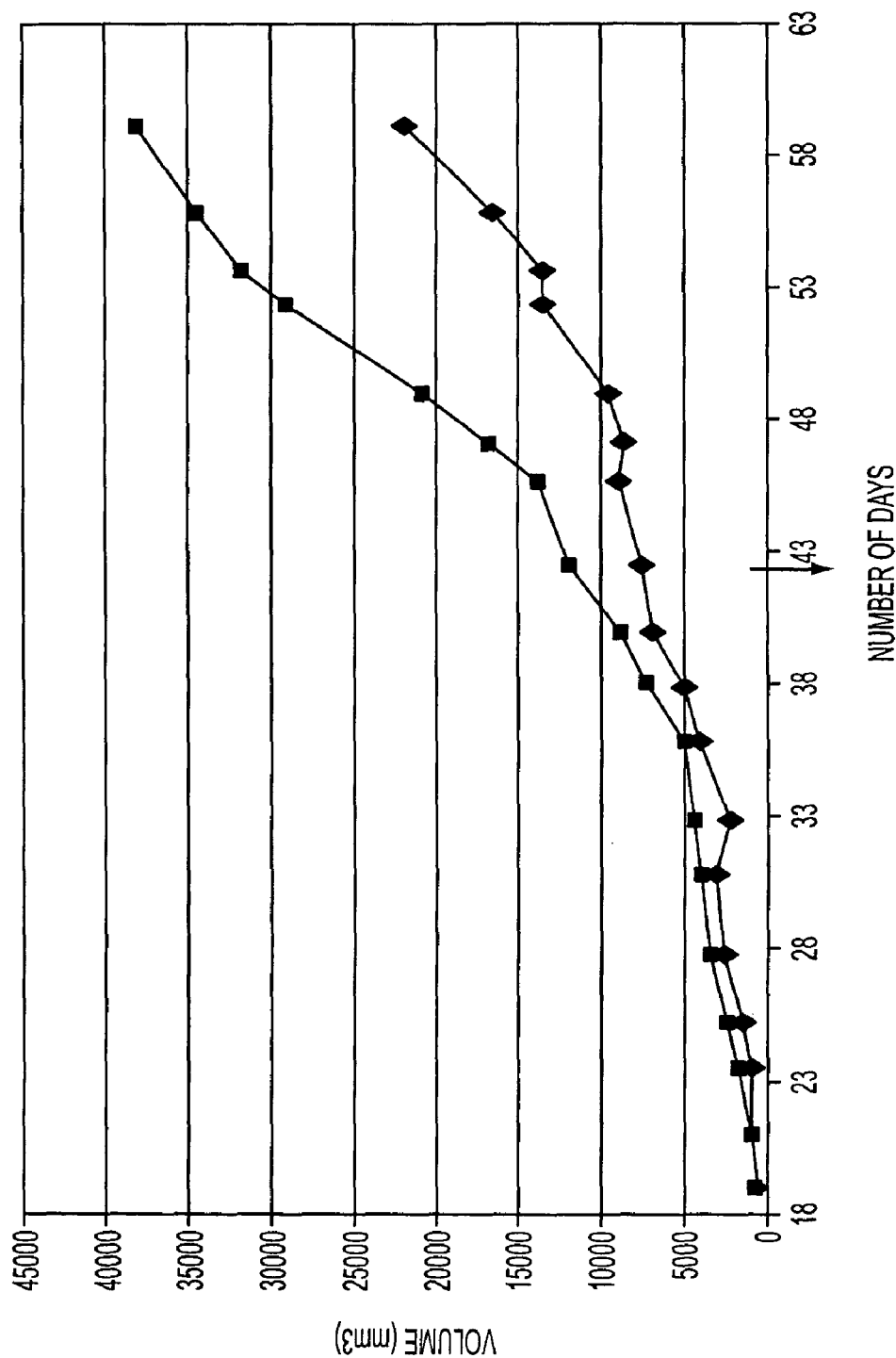
FIG. 9 is a graph of tumor volume over time for tumors generated by the injection of an RNase A-peptide 10 conjugate, RNase A alone, or buffer alone.

The results are shown graphically in FIG. 9.

As the figure shows, after the 33$^{rd}$ day, the progression of the volume of the tumors is clearly slowed by the RNase A coupled with SEQ ID NO: 10.

It would seem that there is less cytotoxicity for some tumor cells than for others.

Protocol 2:

The nude mice received subcutaneous transplants of HH9 tumor cells as described above. On day 9 after the transplant, the mice received twice a week, by peritumoral injection, 100 µg of RNase, or 65 µg of peptide (HBP3)$_2$ or 65 µg of peptide (HBP3)$_2$+100 µg of RNase, or 100 µg of peptide conjugate (HBP3)$_2$-RNase or HBP6-RNase conjugate. On day 26, the mice were killed and their tumors weighed.

The inhibition of the growth of the HH9 tumors treated with the peptide-RNase conjugates is given in Table 12. The inhibition of the growth of the tumors of the mice treated is calculated in relation to the average weight of the tumors of mice that received NaCl.

TABLE 12

| RNase group | NaCl | (HBP3)$_2$ | (HBP3)$_2$ + RNase | (HBP3)$_2$ − RNase | HBP6- RNase | HBP7- RNase |
|---|---|---|---|---|---|---|
| Tumors* | 1720 | 1560 | 1500 | 790 | 810 | 830 |
| Inhibition** | — | 10 | 13 | 54 | 53 | 52 |

*Average weight of tumors of 6 mice in the same group in mg.
**%

The 3 peptide-RNase conjugates inhibit the growth of tumors in an equivalent way, while the peptide alone or with RNase added has little effect.

Example 12

In vitro Transfection of Cells with Plasmid of Luciferase Using Peptides

Transfection of CHO Cells:

The plasmid used is PCMV-LUC (6.4 kb) carrying the luciferase gene under the control of the promoter of the human cytomegalovirus.

The plasmid-peptide complexes are prepared by adding 3 µg of plasmid to 50 µl of NaCl, 0.15 M and 3.3 nmoles of SEQ ID NO: 22 and 23 for 15 minutes. The complexes are prepared in triplicate.

CHO cells are cultivated in the complete medium MEM Alpha containing 6% fetal calf serum and sown with $5\times10^4$ cells per well on a 24-well plate the evening before the experiment. The wells are then emptied of the medium, and the plasmid-peptide complex is added to them (3 µg of plasmid and 3.3 nmoles of peptide in 0.5 ml of complete medium for 5 hours at 37° C.). The medium is then replaced with the complete medium, and the culture is continued for 18-20 hours. The cells are then washed three times with PBS, then lysed with 100 µl of lysis buffer (Promega) containing 1% Triton X-100 and 2 mM DTT.

Then a 15 µl sample of the lysate is taken to measure the luciferase with the Promega luciferin kit and 15 other µl to calculate the quantity of proteins in the lysate using the Bradford Test. The relative luciferase units (RLU) are reported in mg of proteins. The results are reported in Table 13 below.

TABLE 13

| | RLU 10$^6$/mg of proteins |
|---|---|
| SEQ ID NO: 22 | 1.9 |
| SEQ ID NO: 23 | 11.5 |

The results show that the expression of luciferase is possible by complexing the plasmid with one of the vectors and that the expression is increased 6 times (SEQ ID NO: 23) by adding HBP of apolipoprotein to SEQ ID NO: 22.

Transfection of 3T3 Cells

Technique: The plasmid pCMVLUC (carrying the gene for luciferase) provided by Qiagen is used according to their instructions. 3T3 cells are sown the night before in 24-well plates ($8\times10^4$ cells/well) in the complete culture medium.

The peptides and the plasmid are complexed in a ratio of 1.6 nmoles/µg in 50 µl of NaCl 0.15M for 20 minutes at laboratory temperature. The cells are then washed, and the peptide-plasmid complex added to the cells in 0.5 ml of complete medium. After 5 hours of incubation at 37° C., the reaction medium is eliminated, and 1 ml of complete medium is added to the cells. After 24 hours of culture, the cells are then washed 3 times with PBS and lysed with 100 µl of lysis buffer (Promega) containing 1% Triton X-100 and 2 mM DTT for 15 minutes. The luciferase test is done on the cell lysate after centrifugation. The quantity of protein in the lysate is measured using the Bradford Test (Bio-Rad) and calculated according to a curve established with bovine gamma globulins. The luciferase activity is estimated on 15 µl of lysate plus 100 µl of reagent of luciferase containing luciferin (Promega). The relative luciferase units (RLU) are measured in a luminometer (Berthold Systems) and reported in mg of protein.

Results: The quantity of luciferase expressed by the transfected cells is shown in Table 14 below.

TABLE 14

| pCMVLUC | alone | Peptide SEQ ID NO: 40 | Peptide SEQ ID NO: 41 | Peptide SEQ ID NO: 42 |
|---|---|---|---|---|
| RLU | 0.004* | 1.9 | 0.9 | 5 |

*x $10^6$/mg of protein

The peptide complexed to the plasmid permits its transfer inside the cells as well as expression of the gene for luciferase. The efficacy of the transfection expressed by the quantity of luciferase (RLU/mg of protein) varies depending on the peptides used. Peptide SEQ ID NO: 42 and peptide SEQ ID NO: 40 give values 5.5 times and 2.6 times higher, respectively, than peptide SEQ ID NO: 41.

Example 13

Evaluating the Penetration of Substances Using Transporters Coupled to Peptides

If we now take the transporters in the invention, Table 15 below gives some examples of transporters and substances of interest for which they have a strong affinity.

TABLE 15

| TRANSPORTERS | SUBSTANCES OF INTEREST |
|---|---|
| Peptide - Protein A | Human or rabbit IgG |
| Peptide - Protein G | Bovine, goat or mouse IgG |
| Peptide - anti-IgG F(ab1)2 | All IgG from the same species |
| Peptide - anti-peroxidase IgG | Peroxidase and any molecule containing peroxidase |
| Peptide - anti-RNase F(ab1)2 | Ribonuclease A |
| Peptide - Concanavalin A | A large number of glycoproteins |
| Peptide - Streptavidin-Avidin | Biotin and any molecule containing biotin |

In the table above, the general term "peptide" means "sequence of amino acids in the invention."

Protein A is a protein isolated from *Staphylococcus aureus* which has a molecular weight of 42,000 Da. The characteristic property of this protein is its great affinity for the Fc part of the IgG. This property makes it possible for it to attach 2 to 4 molecules of IgG without interacting with the active sites of the antibodies. Protein A is interesting for human, rabbit and rat IgG, and some mouse IgG.

Protein G, originally, was a protein from 30,000 to 35,000 Da isolated from the cell wall of bacterial strains C or D of streptococcus. Protein G sold by SIGMA is a recombinant protein of 17,000 Da that contains two IgG fixation domains. Like protein A, protein G has a strong affinity for the Fc fraction of the IgG, but it will be used mainly for bovine, mouse and sheep IgG.

F(ab')$_2$ come from antibodies. We will use as examples mouse anti-IgG sheep IgG obtained from sheep immune serum. They are purified by affinity chromatography in which the solid phase is composed of mouse IgG fixed on spheres of polyacrylamide-agarose. This is purification by immunoabsorbent that permits specific fixation of the mouse anti-IgG sheep IgG by an antigen-antibody reaction. This antigen-antibody bond is dissociated by an acid pH. Managed digestion of the IgG by proteolytic enzymes makes it possible to obtain fragments of different antibodies. Pepsin is used to obtain bivalent fragments F(ab')$_2$ reduced in size (MW=92,000 Da), and Fc fragments totally digested into small polypeptides. Eliminating the Fc fragment makes it possible to reduce the size of the antibodies and simplifies coupling with the peptides. Creating an anti-IgG peptide-F(ab')2 transporter will make it possible to internalize a great variety of mouse IgG in large quantities.

Anti-peroxidase IgG is a monoclonal antibody of isotype IgG1 that is isolated from mouse ascites. It is purified by affinity chromatography on protein G (GammaBind Plus Sepharose: Pharmacia). This antibody has a strong affinity for peroxidase and, by the same token, for all molecules containing peroxidase. Peroxidase (PO) is an enzyme extracted from the black radish with a molecular weight of 44,000 Da, which can be combined very easily with many molecules. Creating an anti-PO peptide-IgG will make it possible to internalize PO and any substance containing PO into the cells.

Concanavalin, extracted from *Canavalia ensiformis*, is a lectin that has an affinity for the terminal groups α-D-mannosyl and α-D-glucosyl of proteins. This property allows it to react with many glycoproteins. Creating a peptide-concanavalin transporter will make it possible to internalize many glycoproteins or glycolized molecules into cells.

Streptavidin, a molecule weighing 60,000 Da extracted from *Streptomyces avidinii*, and avidin, extracted from egg white, both have four biotin recognition sites. Their affinity constant for this small molecule is very high (KD=$10^{-13}$M) which allows them to interact with all substances containing biotin. Creating a peptide-streptavidin or peptide-avidin transporter will make it possible to internalize biotin and any molecule containing biotin into the cells.

The examples described below illustrate the creation and use of such transporters.

Example 14

Evaluating the Penetration of Bovine Ribonuclease A (RNase A) Transported by a Transporter Peptide-F(ab')$_2$, Anti-RNase Into the Cells Managed digestion of the anti-RNase IgG by a proteolytic enzyme, pepsin, makes it possible to obtain fragments F(ab')$_2$. This digestion, which is done in a sodium acetate solution pH 4.5 with 2% pepsin, makes it possible to fragment the fragment Fc of the IgG without altering the active sites of the antibody.

Two mg of antibody F(ab')$_2$ anti-RNase in 1 ml of potassium phosphate buffer 0.1 M pH 7.4 are added to 110 µg of SMCC [succinimidyl 4-(N-maleimidomethyl)cyclohexane-1-carboxylate] in 11 µl of dimethylsulfoxide. The solution is incubated for 45 minutes at laboratory temperature. The excess reagent is eliminated by centrifugation on ultrafiltration membranes (cutoff threshold=10,000 Da, Vivascience), followed by three washings in sodium phosphate buffer 10 mM, pH 7 containing 01.5 M of NaCl and 5 mM of EDTA. The coupling with the peptide is then done in a molar ratio of 6 peptides to 1 F(ab')$_2$ in the sodium phosphate buffer 10 mM, pH 7, containing 0.5 M of NaCl and 5 mM of EDTA for three hours at laboratory temperature. Then, the excess uncoupled peptide is totally eliminated by centrifugation on ultrafiltration membranes, as in the preceding step. These transporters [anti-RNase peptide-F(ab')$_2$)] are added to ribonuclease A in some complete culture medium, and the solution is incubated for 1 hour at laboratory temperature. The molar ratio of this reaction is 2 RNase/1 F(ab')$_2$.

To evaluate the penetration of RNase A under the microscope, the cells are cultivated in the presence of the complexes [anti-RNase peptide-F(ab')$_2$]-RNase A diluted to decreasing concentrations of RNase A (from 100 to 6 µg/ml) in some culture medium for 4 hours at 37° C.

At the end of the incubation, the cells are washed three times with PBS, then fixed for 15 minutes in absolute ethanol at −20° C. The penetration of the RNase is evaluated after incubation for 1 hour with an anti-RNase antibody coupled with peroxidase. The cells are then washed with PBS, and the peroxidase activity is revealed by diaminobenzidine in the presence of $H_2O_2$.

To measure the quantity of RNase A internalized, the cells are trypsinized, transferred into microtubes and counted. They are washed twice by centrifugation with PBS, then the residue is suspended in 220 µl of lysis buffer (tris buffer, 0.1 M, pH 8, 0.5% Nonidet 40). The quantity of RNase A present in the cell lysate is measured by ELISA on plates sensitized with anti-RNase A rabbit antibody and revealed by an anti-RNase A rabbit antibody conjugate coupled with peroxidase, with reference to a standard curve established with RNase. The results given in Table 16 illustrate the internalization of RNase A by the anti-RNase transporter F(ab')$_2$ and the internalization of the RNase coupled covalently to the peptide inside the HeLa cells.

TABLE 16

|  | Transporter + RNase A | Peptide– RNase A | Natural RNase |
|---|---|---|---|
| Quantity of RNase internalized (pg/10$^4$ cells) | 476 | 433 | 0 |

Example 15

Evaluation of Penetration of Mouse IgG Transported by a Peptide-F(ab')$_2$-Mouse Anti-IgG Transporter Inside Cells The peptide-F(ab')$_2$-mouse anti-IgG transporters are obtained by the technique described above.

These transporters [peptide-F(ab')$_2$ anti-IgG] are added to the mouse IgG in some NaCl 0.5M buffer. The solution is incubated for 1 hour at laboratory temperature. The molar ratio of this reaction is 1 F(ab')$_2$/1 IgG. After an hour of incubation, the complexes formed are diluted in some complete culture medium.

To evaluate the penetration of the IgG under the microscope, the cells are cultivated in the presence of complexes [peptide-F(ab')$_2$ anti-IgG]-IgG diluted to decreasing concentrations of IgG (from 100 to 6 µg/ml) in some complete culture medium for 4 hours at 37° C.

At the end of incubation, the cells are washed three times with PBS, then fixed for 15 minutes in absolute ethanol at −20° C. The penetration of the IgG is evaluated after incubation for 1 hour with an anti-IgG antibody coupled to peroxidase. The cells are then washed with PBS, and the activity of the peroxidase is revealed by diaminobenzidine in the presence of $H_2O_2$.

To measure the quantity of IgG internalized, the cells are trypsinized, transferred into microtubes and counted. They are washed twice by centrifugation with PBS, then the residue is suspended in 220 µl of lysis buffer (tris buffer 0.1M, pH 8, 0.5% Nonidet 40). The quantity of IgG present in the cell lysate is measured by ELISA on plates sensitized with anti-IgG sheep antibody and revealed by an anti-IgG sheep antibody conjugate coupled with peroxidase, with reference to a standard curve established with the IgG. The activity of the peroxidase is revealed with orthodianisidine and $H_2O_2$.

The same transporter [peptide-F(ab')$_2$ anti IgG] can transport a large variety of mouse IgG inside the cells.

The results given in Table 17 illustrate the internalization of different mouse IgG or potentially rat IgG inside HeLa cells via the same transporter [peptide-F(ab')$_2$ anti-IgG].

TABLE 17

|  | Quantity of IgG internalized (pg/10$^4$ cells) |
|---|---|
| Transporter + anti-p53 IgG | 1100 |
| Transporter + anti-p21 IgG | 1200 |
| Transporter + anti-PO IgG | 695 |
| Transporter + biotinylated IgG | 153 |
| Transporter + mouse IgG | 5960 |
| Transporter + F.4.1 | 3200 |
| F.4.1 | 1299 |

Anti-p53 IgG: specific murine monoclonal antibody of protein p53. Anti-p21 IgG:

specific monoclonal antibody of protein p21 that comes from a rat-rat hybridoma, reacting with mouse anti-IgG antibodies. Anti-PO IgG: specific murine monoclonal antibody of peroxidase. F.4.1: anti-DNA murine monoclonal antibody that penetrates inside cells by itself.

Example 16

Evaluation of Penetration of Peroxidase (PO) or Molecules Containing Peroxidase Transported by a Peptide-IgG Anti-PO Transporter into Cells Two mg of specific monoclonal IgG antibody of peroxidase or their fragment F(ab')$_2$ in 1 ml of potassium phosphate buffer 0.1 M, pH 7.4 are added to 110 µg of SMCC [succinimidyl 4-(N-maleimidomethyl)cyclohexane-1-carboxylate] in 11 µl of dimethylsulfoxide. The solution is incubated for 45 minutes at laboratory temperature. The excess reagent is eliminated by centrifugation on ultrafiltration membranes (cutoff threshold =10,000 Da, Vivascience), followed by three washings in sodium phosphate buffer 10 mM, pH 7 containing 0.5 M of NaCl and 5 mM of EDTA.

The peptide is then coupled in a molar ratio of 6 peptides to 1 IgG or 1 F(ab')$_2$ in the sodium phosphate buffer 10 mM, pH 7, containing 0.5 M of NaCl and 5 mM of EDTA for three hours at laboratory temperature. Then, the excess uncoupled peptide is totally eliminated by centrifugation on ultrafiltration membranes, as in the preceding step. These transporters [peptide-IgG anti-PO] are added to the peroxidase or the biotinylated peroxidase in some 0.5 M NaCl buffer. The solution is incubated for 1 hour at laboratory temperature. The molar ratio of this reaction is 2 PO/1 IgG or F(ab')$_2$.

To evaluate the penetration of the PO or the molecules containing PO under the microscope, the cells are cultivated in the presence of [peptide-IgG anti-PO]-PO complexes at decreasing concentrations of PO or molecules containing PO (100 to 6 μg/ml) in some culture medium for 4 hours at 37° C.

At the end of the culture, the cells are washed three times with PBS, then fixed for 15 minutes in absolute ethanol at −20° C. The cells are then washed with some PBS, and the penetration of the PO or the molecules containing PO is evaluated by the activity of peroxidase revealed by diaminobenzidine in the presence of $H_2O_2$.

To measure the quantity of PO internalized, the cells are trypsinized, transferred into microtubes and counted. They are washed twice by centrifugation with PBS, then the residue is suspended in 220 μl of lysis buffer (tris 0.1 M buffer, pH 8, 0.5% Nonidet 40). The quantity of PO present in the cell lysate is measured by ELISA on plates sensitized with anti-peroxidase mouse antibody and revealed with ortho-dianisidine and $H_2O_2$ with reference to a standard curve for PO.

The results given in Table 18 illustrate the internalization of the PO and the biotinylated PO inside HeLa cells via the transporter [peptide-IgG anti-PO].

TABLE 18

|  | Peroxidase (PO) | Biotinylated PO |
| --- | --- | --- |
| Quantity of molecules internalized (pg/$10^4$ cells) | 2100 | 1700 |

Example 17

Evaluation of Penetration of IgG Transported by a Peptide-Protein A Transporter into Cells One mg of protein A in 0.5 ml of sodium phosphate buffer 0.1 M, pH 7, is added to 120 μg of SMCC [succinimidyl 4-(N-maleimidomethyl)cyclohexane-1-carboxylate] in 12 μl of dimethylsulfoxide. The solution is incubated for 45 minutes at laboratory temperature. The excess reagent is eliminated by centrifugation on ultrafiltration membranes [cutoff threshold =10,000 Da, Vivascience], followed by three washings in sodium phosphate buffer 0.1 M, pH 7 containing 0.15M of NaCl.

The peptide is then coupled in a molar ratio of 6 peptides to 1 protein A in the sodium phosphate buffer 0.1 M, pH 7, containing 0.15 M of NaCl for three hours at laboratory temperature. Then, the excess uncoupled peptide is totally eliminated by centrifugation on ultrafiltration membranes, as in the preceding step.

These transporters [peptide-protein A] are added to some IgG in some 0.15 M NaCl buffer. The solution is incubated for 20 minutes at laboratory temperature. The molar ratio of this reaction is 2 IgG/1 protein A.

To evaluate the penetration of the IgG under a microscope, the cells are cultivated in the presence of [peptide-protein A]-IgG complexes diluted at decreasing concentrations of IgG (100 to 6 μg/ml) in some culture medium, for 4 hours at 37° C.

At the end of the culture, the cells are washed three times with some PBS, then fixed for 15 minutes in absolute ethanol at −20° C. The penetration of the IgG is evaluated after incubation for 1 hour with an anti-IgG antibody coupled with the PO or with PO alone for the anti-PO IgG. This step is not necessary in the internalization of IgG conjugated with PO (for example: rabbit IgG-PO). The cells are then washed with PBS, and the activity of the peroxidase is revealed by diaminobenzidine in the presence of $H_2O_2$.

To measure the quantity of IgG internalized, the cells are trypsinized, transferred into microtubes and counted. They are washed twice by centrifugation with PBS, and then the residue is suspended in 200 μl of lysis buffer (tris buffer 0.1M, pH 8, 0.5% Nonidet 40). The quantity of IgG present in the cell lysate is measured by ELISA on plates sensitized with anti-IgG antibody and revealed by an anti-IgG antibody conjugate coupled with peroxidase, with reference to a standard curve established with the IgG. The PO activity is revealed with ortho-dianisidine and $H_2O_2$. The results given in Table 19 illustrate the internalization of different IgGs inside HeLa cells via the transporter [peptide-protein A].

TABLE 19

|  | Rabbit IgG-PO | Mouse IgG Anti-PO | IVIg |
| --- | --- | --- | --- |
| Quantity of IgG internalized (pg/$10^4$ cells) | 10800 | 480 | 26000 |

Example 18

Transport of Anti-CEA Antibody in Colon Cancer Cells a) Experiments were done with anti-CEA 35A7 Ab and the peptides in sequence SEQ ID NO: 10, SEQ ID NO: 30 and SEQ ID NO: 35, also called 1047, HBP7 and HBP10, respectively.

Peptide 1047 was coupled with 35A7 and Herceptin®. After a test of the antibody activities of the conjugates by ELISA, the internalization was studied by immunofluorescence in comparison with the initial antibody at 37° C. and 4° C. On cells LS174T, human colon carcinoma CEA+, the conjugate 35A7-1047 internalizes after 1 hour 15 minutes, while 35A7 showed no internalization until 5 hours. On SKOv3 cells, human ovarian carcinoma ErbB2+, the conjugate Herceptin®-1047 presents rapid internalization close to that obtained with Herceptin®. After radiomarking with $^{125}$I, the conjugates demonstrate immunoreactivity close to the initial Ab on Ag immobilized on Sepharose. A gel filtration analysis shows the absence of aggregate.

b) Comparison of peptides 1047, HBP7 and HBP10. This comparison concerns only Ab 35A7.

In Vitro Experiments

A kinetic study of the internalization of different conjugates (35A7-1047, 35A7-HBP7 and 35A7-HBP10) on LS174T cells shows greater internalization with peptide HBP7 than with 1047 and HBP10. These two peptides give comparable results. On SKOv3 and CEA-cells, 1047 and HBP7 induce internalization comparable to that obtained on LS174T, while HBP10 gives results cut in half.

In Vivo Experiments

The 3 conjugates 35A7-1047, 35A7-HBP7 and 35A7-HBP10 marked with $^{125}$I were studied on nude mice with LS174T tumors compared with marked 35A7. $^{131}$I-35A7 shows around 13% tumor capture of the dose injected per gram (% ID/g) 6 hours post-injection. This capture is between 20% and 25% ID/g of tumor 24 hours post-injection. Conjugate $^{125}$I-35A7-1047 demonstrates somewhat faster elimination and slightly less tumor capture compared to $^{131}$I-35A7 (18.6% vs. 21.2% ID/g at 24 h). Conjugate $^{125}$I-35A7-HBP7 shows major hepatic capture after 6 h. This causes rapid elimination and low tumor capture (8.5% ID/g at 24 h). Conjugate [125]I-35A7-HBP10, with a biodistribution very close to that of the natural antibody, has the best tumor capture of the 3 conjugates.

c) the induction effect of internalization with peptide 1047 is particularly visible on 35A7, an Ab directed against CEA which is an Ag that does not internalize. The effect is less evident on Herceptin®, which internalizes quickly after fixation to its Ag, ErbB2.

Figure 11A:
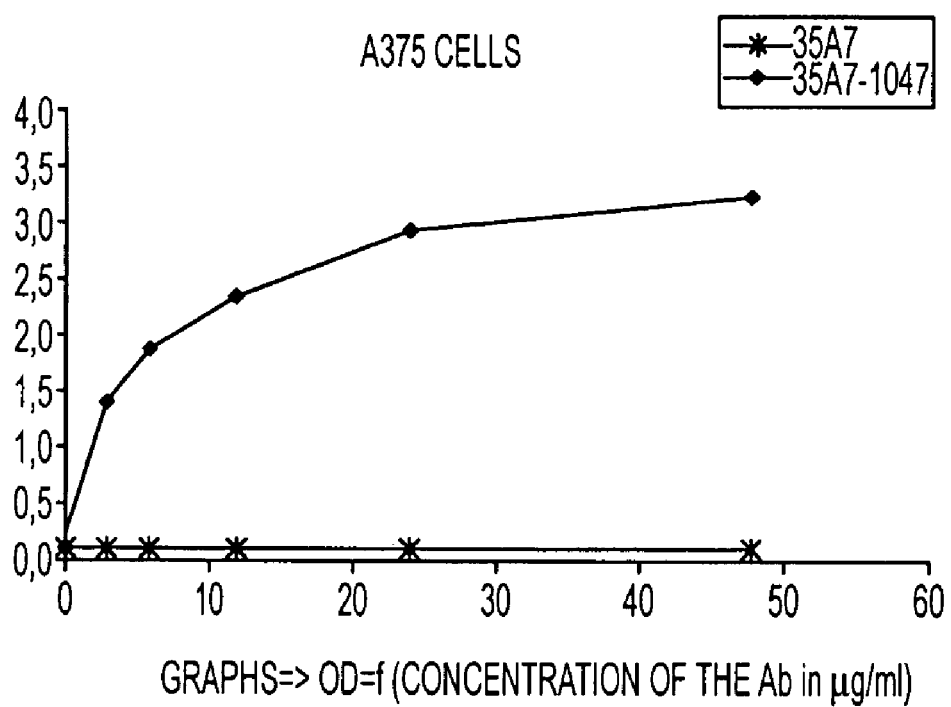
FIG. 11A-B show graphs depicting Test 1: on A375 cells, negative ACE, FIG. 11A and 5F12 cells, positive ACE, FIG. 11B.
Figure 11B:
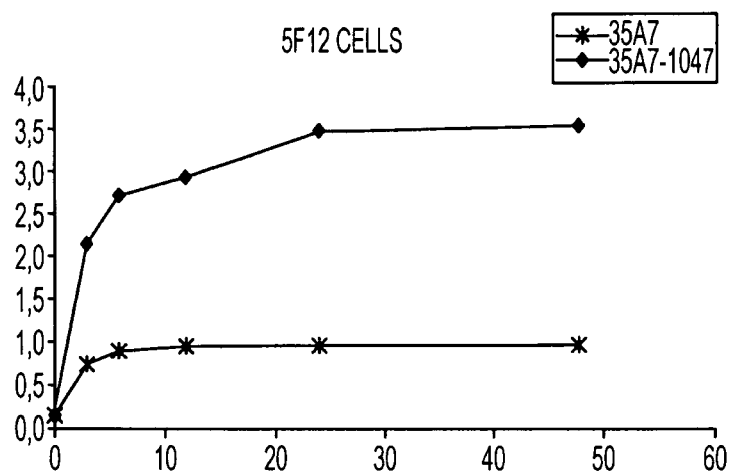

The in vitro experiments done with 1047, HBP7 and HBP10 show that the three peptides induce internalization of 35A7. HBP7 seems to be the most active, but HBP10 is the one that seems to respect most the specificity of the antibody (marked effect on CEA+ cells, reduced effect on CEA− cells). The in vivo experiments confirm the results obtained in vitro.

d) FIGS. 11 to 16 attached illustrate the results above.
The peptides:
1047: 2420 Da=>on anti-ACE and anti-erbB2 Ab
HBP7: 1827 Da=>on anti-ACE Ab only
HBP10: 1696 Da=>on anti-ACE Ab only
Coupling:

After refinement, the conditions set for coupling (preventing the formation of antibody aggregates) are: 18 SMCC/Ig and 12 pept/Ig-SMCC Internalization test on cells in cultures:

FIGS. 11A and B show Test 1: on A375 cells (negative ACE) and 5F12 cells (positive ACE), 40,000 cells per well (24-well box). Incubation with natural antibody (Ab): 35A7 versus conjugated Ab: 35A7-1047, 4 hours at 37° C. Washing, fixation, incubation with secondary-peroxidase Ab, OPD indicator, reading 490 nm. DO based on concentration of antibody in µg/ml.

Figure 12:
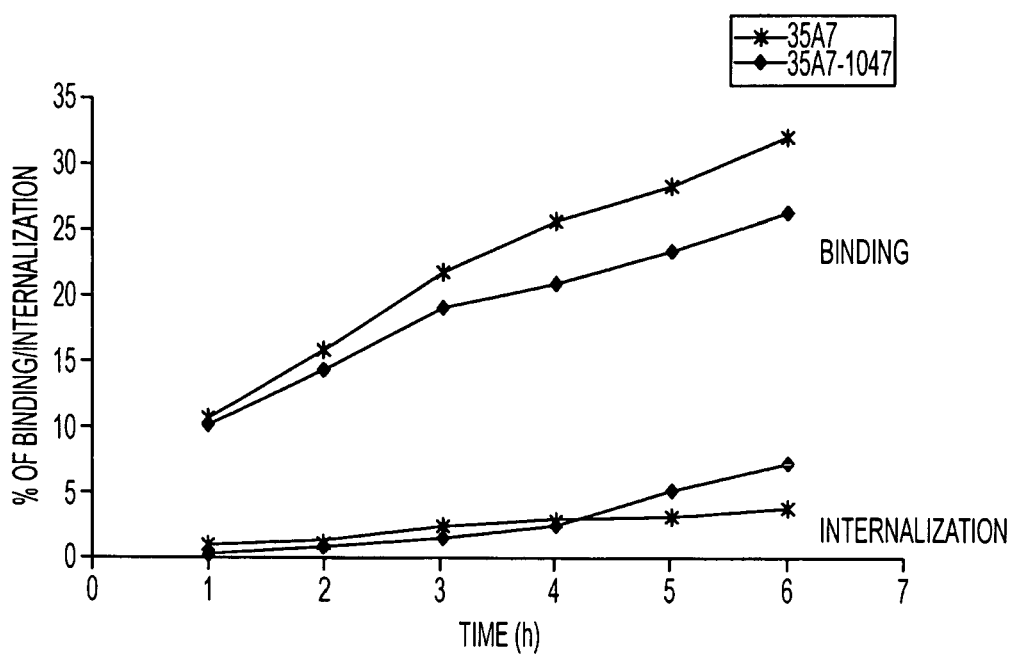
FIG. 12 shows a graph depicting the results of Test 1 with antibodies marked with iodine 125.

FIG. 12 shows Test 1 with the antibodies marked with iodine 125.

Figure 13A:
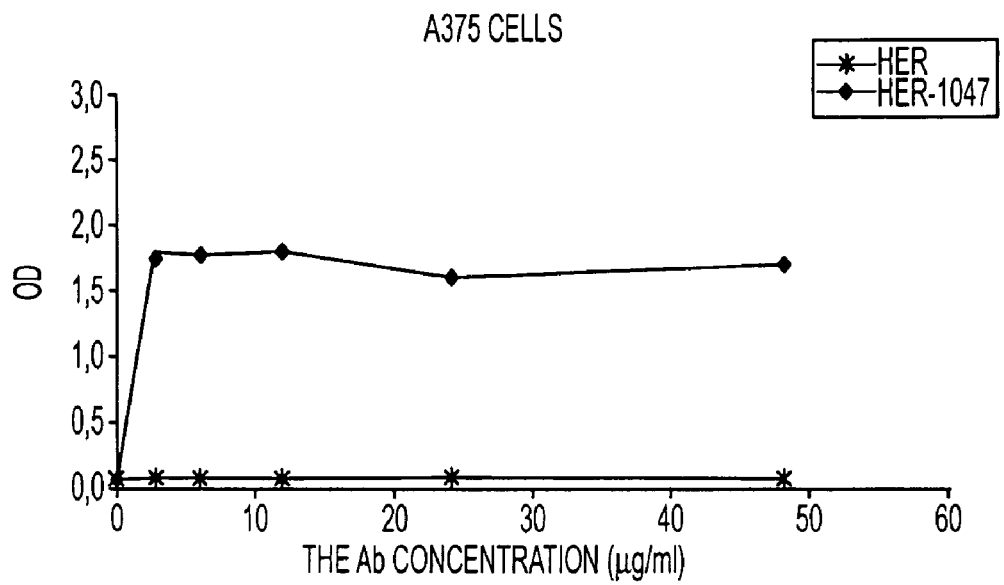
FIG. 13A-B show line graphs of Test 2: on A375 cells, negative erbB2, FIG. 13A, and SKOV3 cells, positive erbB2, FIG. 13B.
Figure 13B:
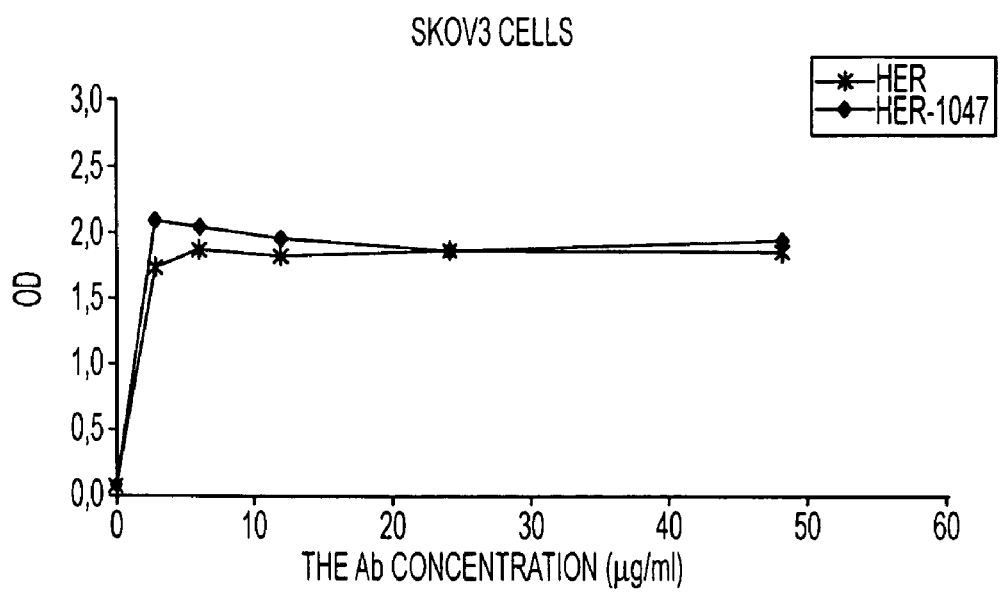

FIGS. 13A and B show Test 2: on A375 cells (negative erbB2) and SKOV3 cells (positive erbB2), 40,000 cells per well (24-well box). Incubation with natural antibody (Ab): Herceptin versus conjugated Ab: HER-1047, 4 h at 37° C. Washing, fixation, incubation with secondary-peroxidase Ab, OPD indicator, reading 490 nm.

Figure 14A:
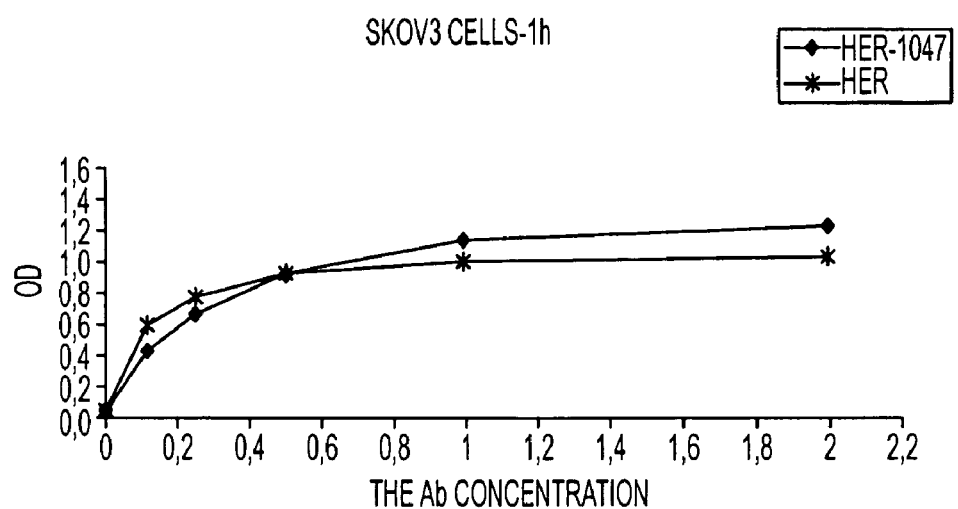
FIG. 14A-B show line graphs of Test 3 on SKOV3 cells, with varying concentrations of antibodies and different incubation times 1 h (FIG. 14A) or 4 h (FIG. 14B).
Figure 14B:
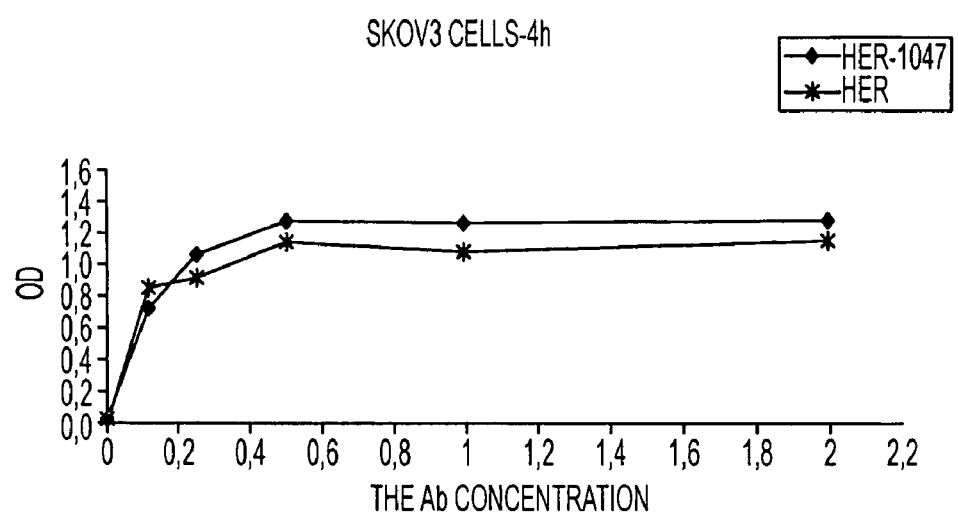
Figure 15A:
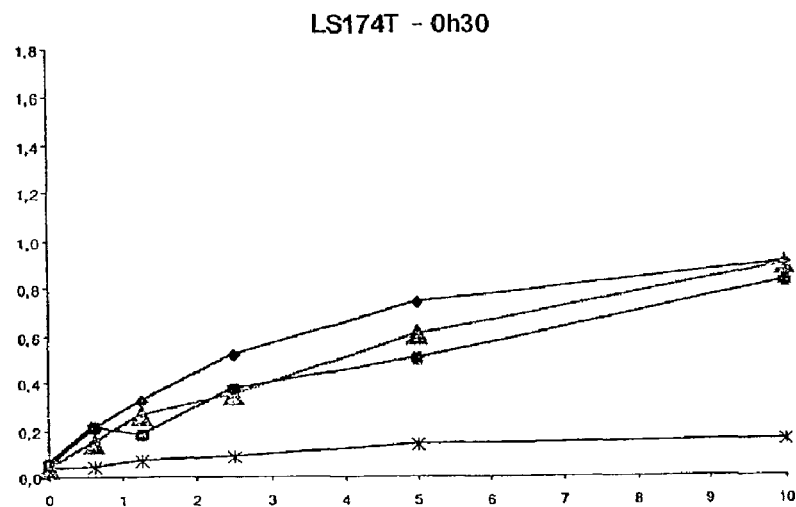
FIG. 15A-F show line graphs of Test 4 comparing the uptake of three peptides: 1047, HBP7, and HBP10 on LS174T (ACE+) cells at 0.5 h (FIG. 15A); at 1.0 h (FIG. 15B); at 2.5 h (FIG. 15C); and at 4.0 h (FIG. 15C); and on SKOV3 (ACE−) cells at 2.5 h (FIG. 15E); at 4.0 h (FIG. 15F).
Figure 15B:
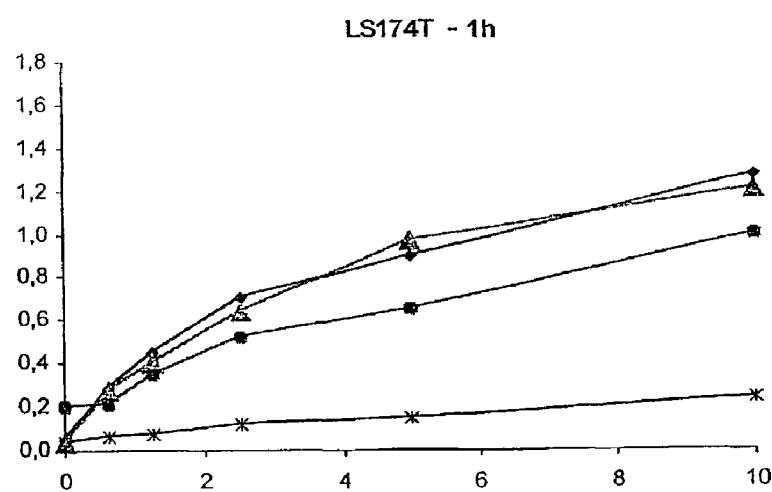
Figure 15C:
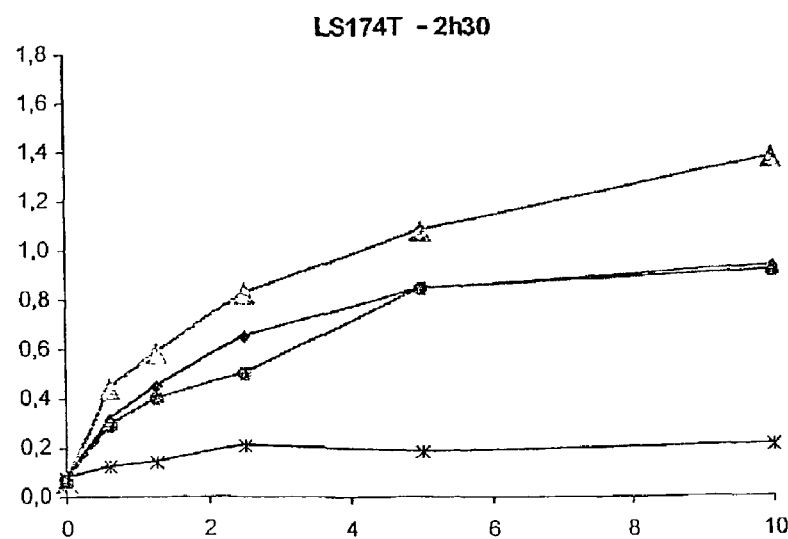
Figure 15:
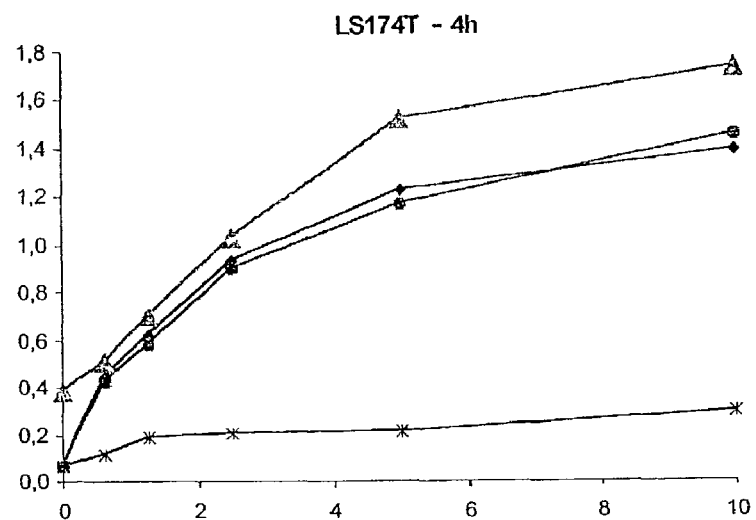
Figure 15:
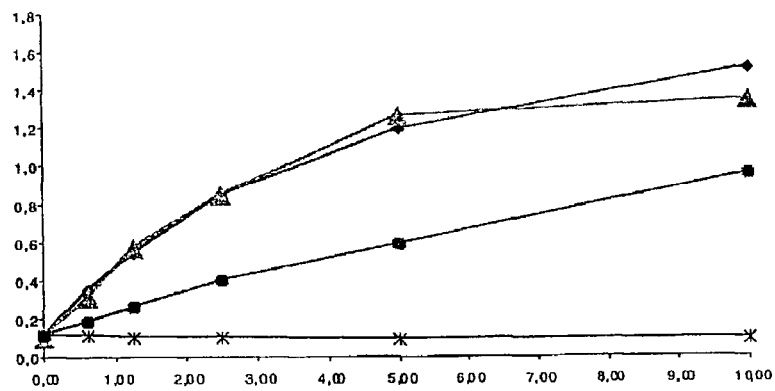
Figure 15:
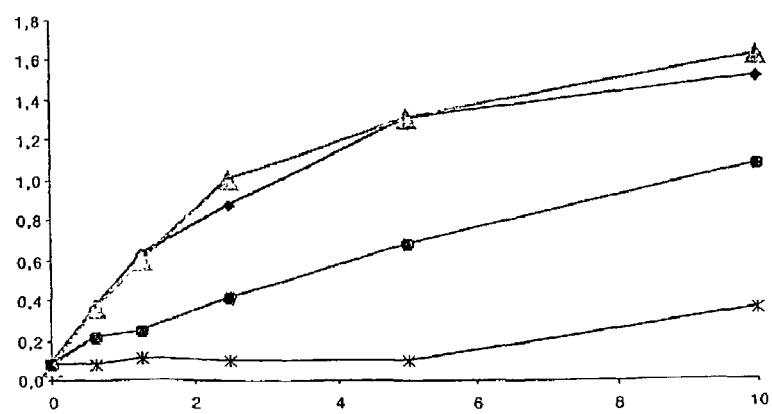
Figure 16A:
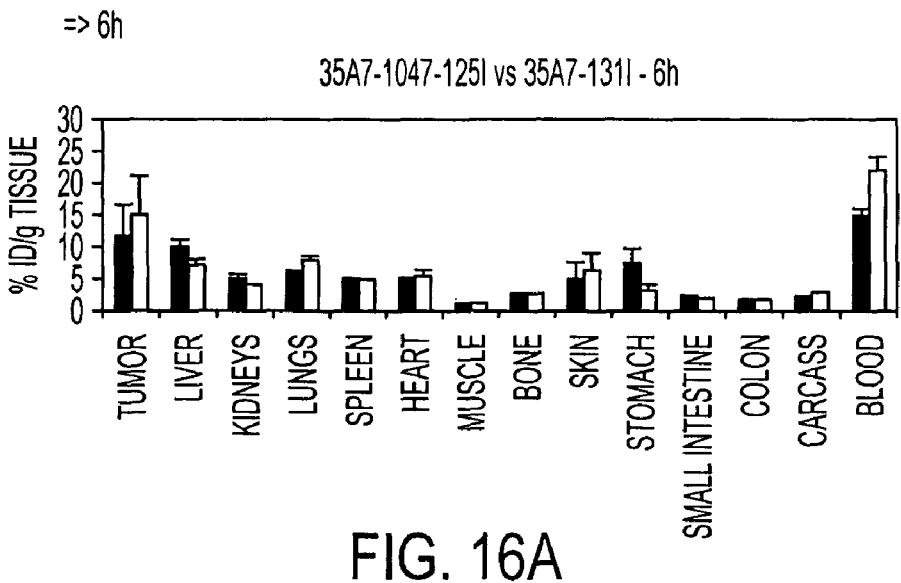
FIG. 16A-F are bar graphs comparing the in vivo distribution of conjugated 35A7 ($I^{125}$) with natural 35A7 ($I^{131}$) in mice, where the black bar indicates the conjugated antibody and the white bar indicates the natural antibody.
Figure 16B:
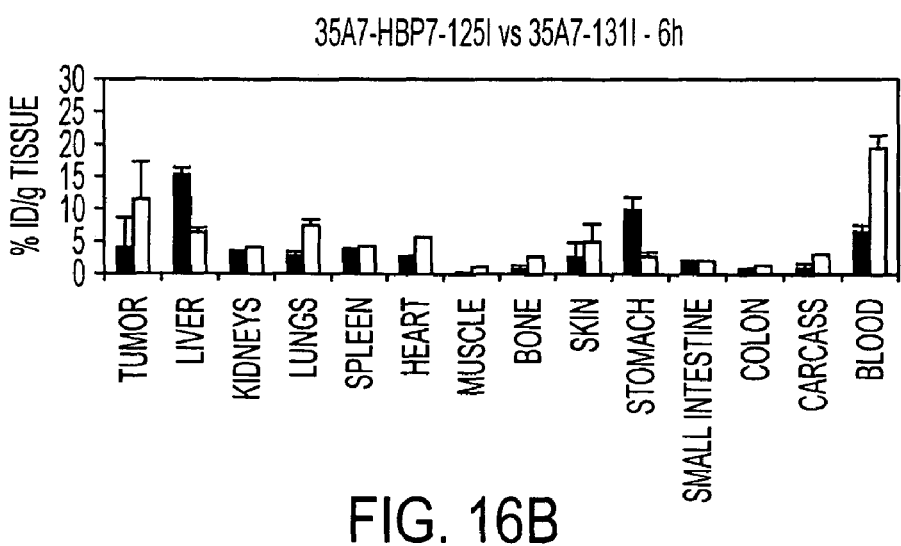
Figure 16C:
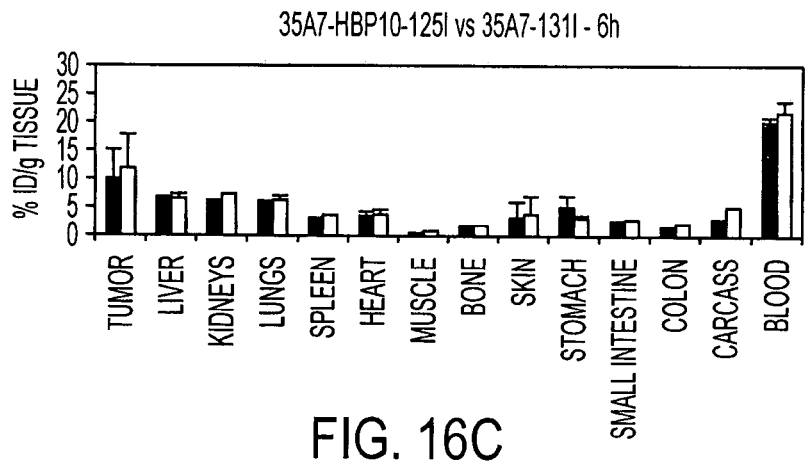
Figure 16D:
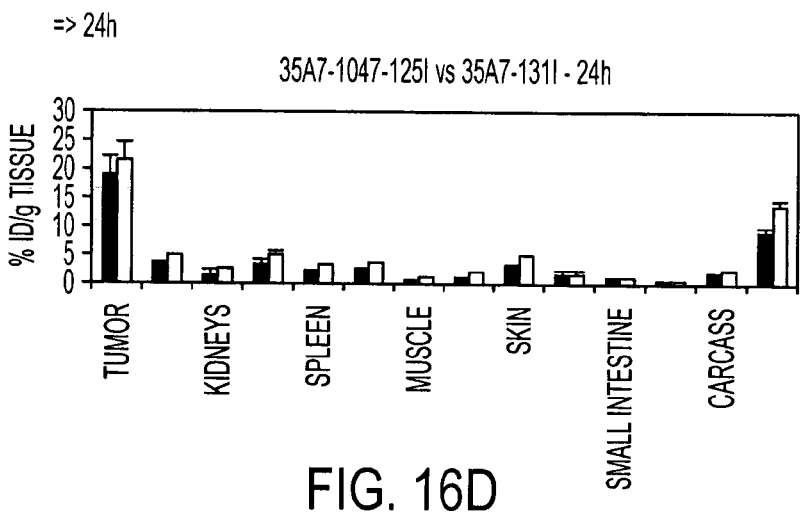
Figure 16E:
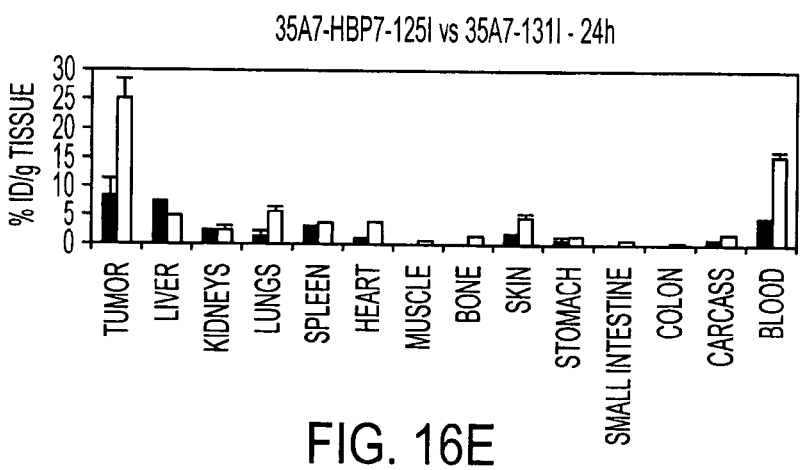
Figure 16F:
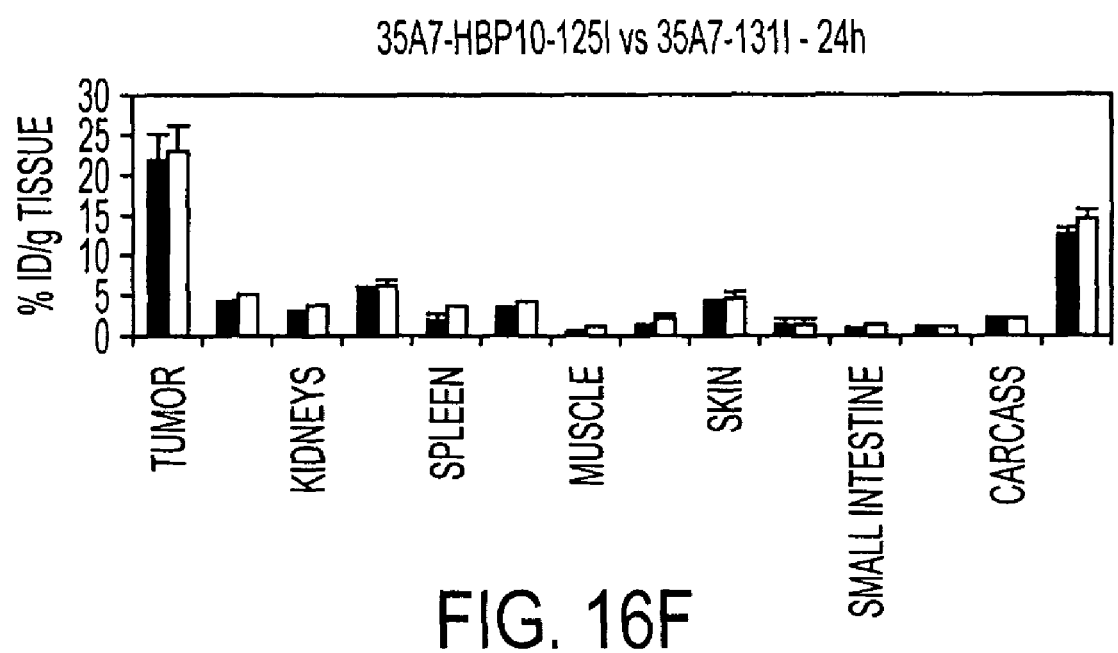

FIGS. 14A and B show Test 3: by reducing the concentration of antibodies and varying the incubation time 1 h or 4 h.

FIGS. 15A to F show Test 4: identical protocol but by comparing the three peptides (1047-HBP7-HBP10) on SKOV3 (ACE−) and LS174T (ACE+) cells.

FIGS. 16A to F illustrate the in vivo experimentation: distribution of antibodies 35A7-1047, 35A7-HBP7, 35A7-HBP10 radiomarked with iodine 125, versus 35A7-iodine 131; Swiss nude/nude mice implanted with LS174T (human colon carcinoma, CEA+); co-injection of 5 µg Ab-pept* and 5 µg of natural Ab* per mouse, by i.v.; dissection 6h/24 h post-injection, expression of the results as a percentage of the dose injected per gram of tissue. Black bar: conjugated Ab-125I white bar: natural Ab-131I.

Example 19

Transport of Particles Using a Peptide-IgG Derivative

The vector used in the following examples is a monoclonal mouse antibody (IgG1) coupled with the peptide in sequence SEQ ID NO: 10 (1047). The peptide was coupled with the monoclonal antibody as described above.
Fluorescent Spheres: Preparation of Peptide IgG Microsphere Complex:

Some 79-900 nm fluorescent polystyrene microspheres carrying anti-IgG mouse antibodies on their surface (Estapor, Merck eurolab) are diluted to 1/100 in NaCl 0.15M. 4 µl of this preparation is added to a volume of 50 µl containing 10 µg of monoclonal mouse IgG conjugated with peptide SEQ ID NO: 2 and left to incubate for 30 minutes at laboratory temperature. This reaction medium is deposited on the H1299 cells sown ($5 \times 10^4$ cells/well) the night before for 18 hours.

The cells are washed and observed under a fluorescence microscope: the cells incubated with the fluorescent peptide-IgG sphere complexes are highly marked, whatever the size of the spheres, while the controls (fluorescent spheres without peptide-IgG, or with normal IgG) are negative.
Colloidal Gold: Preparation of Peptide-IgG-Colloidal Gold Complex:

Spheres of colloidal gold (British Biocell International) of 10 nm are complexed to monoclonal mouse IgG, conjugated beforehand with peptide 1047, according to the manufacturer's instructions in a ratio of 750 µg of IgG per 1 ml of colloidal gold solution. For the penetration of the complex into the cells, the residue of the suspension is diluted in half in the culture medium.

Example 20

Evaluation of Internalization of Peptide-IgG Spheres Complexes

Fluorescent and Colloidal Mold Under the Electron Microscope.

Figure 19:
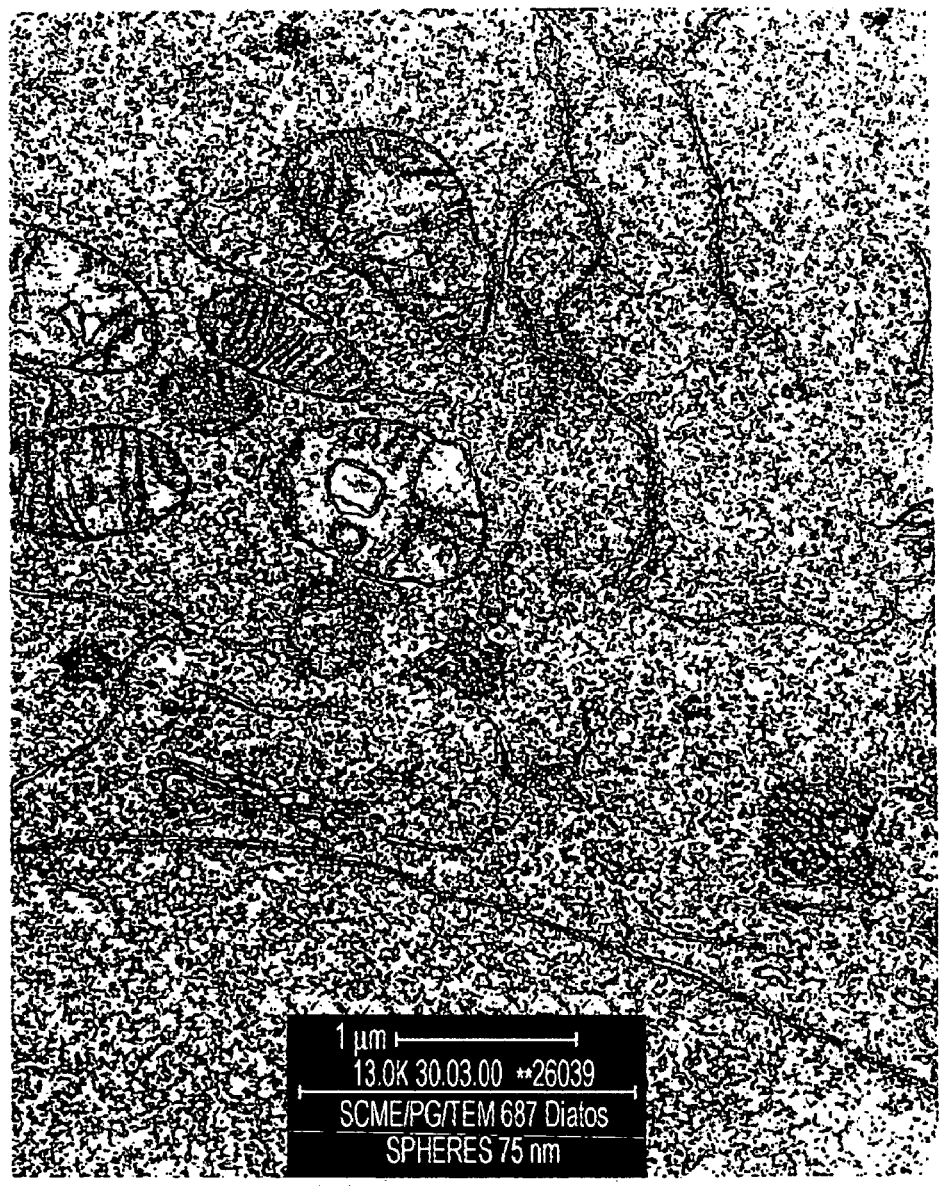
FIG. 19 is an electron micrograph of peptide IgG-microsphere complexes of 70 nm.
Figure 20:
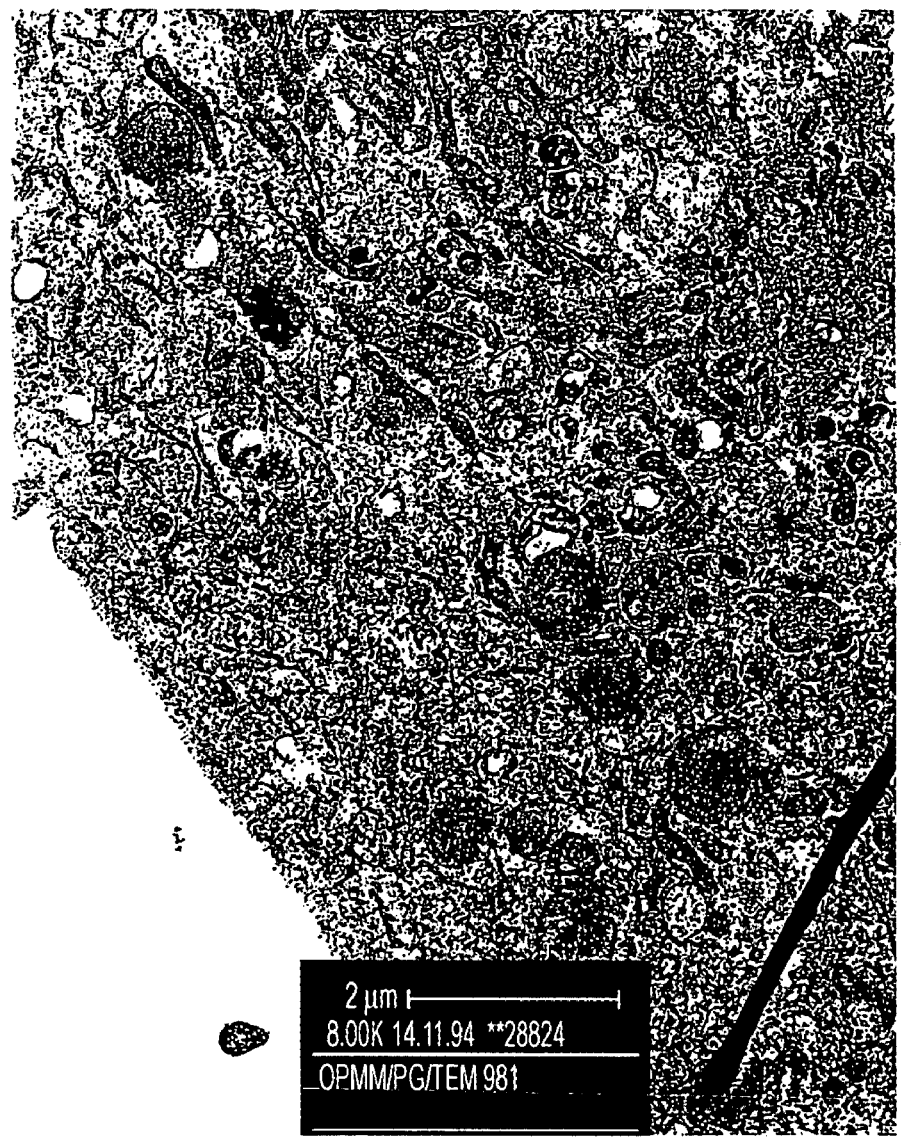
FIG. 20 is an electron micrograph of peptide-IgG-colloidal gold complexes.

After the conjugation steps, the preparations are deposited on H1299 cells cultivated since the night before as described above. After 18 hours of culture for the IgG-fluorescent spheres complex or 4 hours for the IgG-colloidal gold complex, the cells are washed with PBS three times, then fixed in a 1.6% glutaraldehyde solution in sodium phosphate buffer, 0.1M for one hour, then treated as usual for the electron microscope.
Results: The peptide IgG-microsphere complexes of 70 nm (FIG. 19) and the peptide-IgG-colloidal gold complexes (FIG. 20) are visible in some vesicles and in the endoplasmic reticulum of the cytoplasm and around the Golgi area.

Example 21

Transport of Doxorubicin

Anthracyclins like doxorubicin are among the most active agents in the treatment of human cancers. Their mode of entry into the cells is not yet resolved. What is known is that they are quickly transported into the nucleus of the cells. Their toxicity, probably due to their broad diffusion through the body, is a limitation in treatment, preventing the use of a large quantity.

We wanted to see if coupling doxorubicin to the HBP peptides would improve its power to inhibit the growth of human tumors while reducing the toxicity of the drug.
Coupling Peptides to Doxorubicin Doxorubicin, whose amino group is protected, is treated with 4-maleimidobutyric acid in the presence of carbodiimide, which results in the formation of an ester bond between the hydroxyl of doxorubicin and the carboxyl of maleimidobutyric acid. The maleimide group introduced into doxorubicin reacts with the cysteine present in terminal-C or -N of the peptide.

The following conjugates were prepared following the general plan:: 1047-doxorubicin; HBP1-doxorubicin; HBP3-doxorubicin; HBP6-doxorubicin; HBP7-doxorubidin; HBP10-doxorubicin; HBP13-doxorubicin.

Example 22

In Vitro Evaluation of the Biological Acitivity of Doxorubicin Conjugated with Peptides To evaluate the biological activity of peptide-doxorubicin conjugates, the inhibition of the growth of tumor cells in culture is measured.

The cells are sown the night before in 96-well plates at the rate of $10^3$ cells per well. The next day, the supernatant is suctioned off and replaced by 100 µl of medium containing successive dilutions of peptide-doxorubicin or natural doxorubicin ($10^{-6}$ M-$10^{-8}$ M) and the culture continued for 48 hours.

Then, the wells are filled with 50 µl of MTT (3-(4,5-dimethylthiazol-2yl)-2,5-diphenyl tetrazolium bromide) at 1 mg/ml in the culture medium and cultivated for 4 hours. The supernatant is removed, and 100 µl of dimethylsulfoxide is added to them. After the crystals dissolve, the coloration is read at 550 nm.

The results are calculated as a percentage of the mean optical density obtained in the wells of cells containing the dilutions of the samples being tested and the optical density of the wells that received only medium. They are expressed in a molar concentration giving 50% inhibition of the growth of the cells and are reported in Table 20 below.

TABLE 20

| | Cell Lines | | | | | | | |
|---|---|---|---|---|---|---|---|---|
| | H1299 | HH9 | HeLa | B16. F10 | K562 | K562 R* | MCF7 | MCF7R |
| Doxorubicin (natural) | $3 \times 10^{-7}$ | $3 \times 10^{-7}$ | $2 \times 10^{-7}$ | $1 \times 10^{-7}$ | $4 \times 10^{-8}$ | $3 \times 10^{-6}$ | $2 \times 10^{-7}$ | $2 \times 10^{-4}$ |
| (HBP1)$_3$-doxo | $7 \times 10^{-7}$ | nt* | nt* | nt* | $2 \times 10^{-7}$ | $5 \times 10^{-6}$ | $6 \times 10^{-7}$ | $1 \times 10^{-4}$ |
| (HBP3)$_2$-doxo | nt* | nt* | nt* | nt* | $1 \times 10^{-7}$ | $3 \times 10^{-6}$ | $5 \times 10^{-7}$ | $2.5 \times 10^{-4}$ |
| HBP6-doxo | nt* | nt* | nt* | nt* | $3 \times 10^{-7}$ | $5 \times 10^{-6}$ | $6 \times 10^{-7}$ | $6.5 \times 10^{-4}$ |
| HBP7-doxo | nt* | nt* | nt* | nt* | $1 \times 10^{-6}$ | $1 \times 10^{-5}$ | $7 \times 10^{-7}$ | $4 \times 10^{-4}$ |
| HBP10-doxo | nt* | nt* | nt* | nt* | $8 \times 10^{-7}$ | $1 \times 10^{-5}$ | $5 \times 10^{-7}$ | $3.5 \times 10^{-4}$ |
| HBP13-doxo | nt* | nt* | nt* | nt* | $4 \times 10^{-7}$ | $5 \times 10^{-5}$ | $6 \times 10^{-7}$ | $4.5 \times 10^{-4}$ |
| 1047-doxo | $7 \times 10^{-7}$ | nt* | $2.5 \times 10^{-7}$ | $5 \times 10^{-7}$ | $2 \times 10^{-7}$ | $5 \times 10^{-6}$ | $8 \times 10^{-7}$ | $1 \times 10^{-3}$ |

It appears that, in vitro, the sensitivity of the cells to the peptide-doxorubicin conjugates is on the same order of magnitude as that of natural doxorubicin. The lines resistant to doxorubicin (K562R and MCF7R) require a greater concentration of doxorubicin.

Example 23

In Vivo Evaluation of the Anti-Tumor Activity of Peptide-Doxorubicin Conjugates Nude mice are injected with $3 \times 10^6$ HH9 cells subcutaneously in the side. On day 19 after the cell implant, the tumors are measured, and 4 groups of 6 mice are formed that receive by peritumoral injection either NaCl, or natural doxorubicin, or 1047-doxorubicin, or HBP1-doxorubicin conjugates at the rate of 30 µg of doxorubicin or the equivalent of conjugates every two weeks. The tumors are measured and their volume calculated. On day 60, after injection of a total of 120 µg of doxorubicin or the equivalent, the tumor growth is inhibited by 77% with the 1047-doxorubicin conjugate, by 84% with the HBP1-doxorubicin conjugate and by 79% with the doxorubicin alone, respectively, which shows that in vivo these conjugates are at least as effective as natural doxorubicin.

Example 24

In Vivo Evaluation of the Toxocitiy of Peptide-Doxorubicin Conjugates

Injection of doxorubicin or doxorubicin-peptide by the intravenous route makes it possible to compare the toxicity of the different preparations. The estimate is made by the weight loss of the mice (5 mice per group). Two experiments were done:

Experiment 1: The mice received 200 µg per injection at 3-day intervals, or 600 µg of doxorubicin or the equivalent peptide-doxorubicin in all. The mice were weighed the day after the last injection.

Experiment 2: The mice received 2 injections of 200 -µg of doxorubicin or the peptide-doxorubicin equivalent at one week intervals, or 400 µg in all, and were weighed the day after the last injection.

Table 21 below reports the weight loss of the mice treated with doxorubicin or peptide-doxorubicin conjugates. The average weight loss is calculated in relation to the average weight of the mice that received NaCl.

TABLE 21

| Groups | NaCl | Doxo. | HBP3 | HBP6 | HBP7 | HBP10 | HBP13 |
|---|---|---|---|---|---|---|---|
| Exp. 1 | | | | | | | |
| Weight | 23.11 | 16.06 | 21.45 | 20.3 | 19.11 | 21.15 | **nt |
| Loss* | — | 31* | 8 | 12 | 18 | 9 | — |
| Exp. 2 | | | | | | | |
| Weight | 31.4 | 26.7 | 29.5 | 29.5 | 31.4 | 32.5 | 30 |
| Loss* | — | 15 | 6 | 6 | 0 | 0 | 4 |

*%
**not tested

At the 600 µg dose, the mice that received the natural doxorubicin lost 31% of their weight, while those that received peptide-doxorubicin lost only 18% to 8% of their weight. The 400 µg-dose entailed a 15% weight loss in mice that received natural doxorubicin, while the loss was not significant with the peptide-doxorubicin conjugates.

Example 25

Transport of Ubiquitin

Ubiquitin is a polypeptide of 76 amino acids, highly preserved during evolution, present in the organisms of all eukaryotes, with a molecular weight of 8500 Daltons. Intracellular ubiquitin is involved in various cell functions, such as breaking down proteins after their ligation with ubiquitin, the progression of the cell cycle, regulation of the activation of the transcription factor NF-kB. Extracellular ubiquitin has the property of inhibiting the proliferation of hematopoietic stem cells by induction of apoptosis.

Coupling Ubiquitin with a Peptide.

1 mg of ubiquitin in 0.3 ml of sodium phosphate buffer 0.1 m, pH 7 containing 0.15 M NaCl is added to 390 µg of SMCC (succinimidyl 4-(N-maleimidomethyl)cyclohexane-1-carboxylate) in 39 µl of dimethylsulfoxide, and the solution is incubated for 30 minutes at laboratory temperature. The excess reagent is eliminated by centrifugation on ultrafiltration membranes (cutoff threshold=5,000 Dalton, Sartorius), followed by three washings in sodium phosphate buffer 0.1M, pH 7 containing 0.15M NaCl. The peptide is then coupled in a molar ratio of 5 peptides to 1 ubiquitin in 1 ml of sodium phosphate buffer 0.1M, pH7, at laboratory temperature. Then, the excess uncoupled peptide is eliminated by centrifugation on membranes, as in the preceding step.

Evaluation of Penetration of Peptide-Ubiguitin Conjugates

Penetration of the peptide-ubiquitin conjugates is evaluated with conjugates prepared with peptides with a biotin on the N-terminal side.

HT29 cells are sown the night before in 24-well plates ($5 \times 10^4$/wells).

The different (biotinylated) peptide-ubiquitin conjugates are added to decreasing concentrations (100 to 25 µg/ml) in the culture medium for 4 hours at 37° C. At the end of the culture, the cells are washed three times with PBS, then fixed 15 minutes in ethanol at −20° C. The penetration of the peptide-biotin-ubiquitin conjugate is evaluated after incubation for 60 minutes with avidin coupled with peroxidase. The activity of the peroxidase is indicated by diaminobenzidine in the presence of $H_2O_2$.

The penetration, dependent on the concentration of the conjugates in the culture medium, is evaluated under a microscope by the intensity of the coloration expressed by crosses. Table 22 below gives the penetration of peptide-ubiquitin in the cells.

TABLE 22

| | Concentration (µg/ml) | | |
|---|---|---|---|
| | 100 | 50 | 25 |
| Natural ubiquitin | +/−* | +/− | +/− |
| 1047-ubiquitin | +++ | ++ | + |
| HBP7-ubuquitin | ++++ | +++ | ++ |
| HBP10-ubiquitin | +++ | ++ | ++ |

++++: very intense;
+++: intense;
++: positive;
+ slightly positive;
+/− at the limit of the reading.

Evaluation of Biological Activity of the Peptide-Ubiquitin Conjugates.

The proliferation of cells is measured by the test with MTT. Some Daudi ($3 \times 10^4$ cells/wells) were cultivated in 96-well plates for 48 hours at 37° C. in the complete culture medium RPMI plus decreasing concentrations (200-12.5 µg/ml) of natural ubiquitin or ubiquitin conjugated with peptides, and the culture was continued for 48 hours.

Then, the wells are filled with 50 µl of MTT (3-,(4,5-dimethylthiazol-2yl)-2.5-diphenyl tetrazolium bromide) at 1 mg/ml in the culture medium and cultured for 4 hours.

The supernatant is removed, and 100 µl of dimethylsulfoxide is added. After the crystals dissolve, the coloration is read at 550 nm.

Table 23 shows the inhibition of the growth of Daudi cells by the peptide-ubiquitin conjugates. The results, shown in Table 23, are calculated as a percentage of the average optical density obtained in the wells of cells containing the dilutions of the samples being tested and the optical density of the wells that had only medium. They are expressed as a concentration giving 50% inhibition of growth of the cells.

TABLE 23

| | Concentration (µg/ml) | | |
|---|---|---|---|
| | 200 | 100 | 50 |
| Natural ubiquitin | 0* | 0 | 0 |
| 1047-ubiquitin | 60 | 21 | 0 |
| HBP7-ubuquitin | 96 | 68 | 35 |
| HBP10-ubiquitin | 16 | 11 | 0 |

*% of inhibition calculated in relation to the growth of cells that received only culture medium.

Natural ubiquitin does not inhibit the growth of Daudi cells. The conjugate prepared with peptide HBP10 does not inhibit very much, while the conjugate prepared with peptide HBP7 is effective and still gives 35% inhibition at 50 µg/ml. The conjugate prepared with peptide 1047 gives intermediate inhibition values.

Example 26

Transport of Cytochrome C

Cytochrome C is a hemoprotein that constitutes the mitochondrial lipid-protein complex. It plays a vital role in the cellular oxidation of plants and mammals. It is made up of a single polypeptide chain of 104 amino acids (molecular weight 13,000 Daltons) with the hth group attached to the cysteine residues. Graining of cytochrome C of the mitochondria in cytosol causes apoptosis of the cells by activating the caspases.

Coupling Cytochrome C to Peptides

To 4 mg of cytochrome C in 930 µl of sodium phosphate buffer 0.1M, pH7 containing 0.15M NaCl is added 540 µg of SMCC (succinimidyl 4-(N-maleimidomethyl)cyclohexane-1-carboxylate) in 54 µl of dimethylsulfoxide, and the solution is incubated 30 minutes at laboratory temperature. The excess reagent is eliminated by centrifugation on ultrafiltration membranes (cutoff threshold=10,000 Daltons, Sartorius), followed by three washings in sodium phosphate buffer 0.1M, pH7 containing 0.15M NaCl.

The peptide is then coupled in a molar ratio of 10 peptides to 1 cytochrome C in 1 ml of sodium phosphate buffer 0.1M, pH7 containing 0.15 M NaCl, for 3 hours at laboratory temperature. Then, the excess uncoupled peptide is eliminated by centrifugation/filtration as in the preceding step.

Evaluating the Penetration of the Peptide-Cytochrome C Coniugates into the Cells The penetration of the peptide-cytochrome C conjugates is evaluated with some conjugates prepared with peptides having a biotin on the N-terminal side. H1299 cells are cultivated in the presence of the different (biotinylated) peptide-cytochrome C conjugates at decreasing concentrations (100 to 25 μg/ml) in the culture medium for 4 hours at 37° C. At the end of the culture, the cells are washed three times with PBS, then fixed 15 minutes in ethanol at −20°. The penetration of the peptide-biotin-cytochrome C conjugate is evaluated after incubation for 60 minutes with some avidin coupled with peroxidase. The cells are then washed with PBS, and the activity of the peroxidase is indicated by diaminobenzidine in the presence of $H_2O_2$.

The penetration dependent on the concentration of conjugates in the culture medium is evaluated under the microscope by the intensity of the coloration expressed by crosses. Table 24 indicates the penetration of the peptide-cytochrome C conjugates in the cells.

TABLE 24

|  | Concentration (μg/ml) | | |
|---|---|---|---|
|  | 100 | 50 | 25 |
| Natural cytochrome C | −* | − | − |
| 1047-cytochrome C | +++ | ++ | + |

+++ intense;
++ positive;
+ slightly positive;
− negative.

The table above shows that natural cytochrome C does not penetrate the cells and that the 1047-cytochrome C conjugate penetrates effectively up to 25 μl/ml.

Evaluating the Biological Activity in Vitro of Peptide-Cytochrome C Conjugates

H1299 or HT29 cells ($3\times10^4$ cells/well) are cultivated in 96-well plates for 48 hours at 37° C. in the complete culture medium RPMI with decreasing concentrations (200-3 μg/ml) of natural cytochrome C or cytochrome C conjugated with peptides added, and the culture is continued for 48 hours.

The wells are then filled with 50 μl of MTT (3-,(4,5-domethylthhiazol-2yl)-2,5-diphenyl tetrazolium bromide) at 1 mg/ml in the culture medium and are cultured for 4 hours. The supernatant is removed, and 100 μl of dimethylsulfoxide is added to the wells. After the crystals dissolve, the coloration is read at 550 nm.

The results are calculated as a percentage of the mean optical density obtained in the wells of cells containing the dilutions of the samples being tested, and the optical density of the wells that received only medium. Table 25 gives the inhibition of growth of the cells by the peptide-ubiquitin conjugates.

TABLE 25

|  | Concentration (μg/ml) | | | | | |
|---|---|---|---|---|---|---|
| On H1299 cells | 100 | 50 | 25 | 12.5 | 6 | 3 |
| Natural cytochrome C | 0* | 0 | 0 | 0 | 0 | 0 |
| 1047-cytochrome C | 46 | 40 | 29 | 15 | 14 | 0 |

|  | Concentration (μg/ml) | | | | |
|---|---|---|---|---|---|
| On HT29 cells | 200 | 100 | 50 | 25 | 12.5 |
| Natural cytochrome C | 12* | 19 | 10 | 0 | 0 |
| 1047-cytochrome C | 28 | 23 | 23 | 0 | 0 |
| HBP3-cytochrome C | 42 | 22 | 15 | 0 | 0 |
| HBP6-cytochrome C | 41 | 18 | 12 | 2 | 0 |
| HBP7-cytochrome C | 35 | 14 | 5 | 0 | 0 |

*% inhibition calculated in relation to the growth of cells that received only culture medium.

The table above shows the effectiveness of the peptide-cytochrome C conjugates on two types of cells. Natural cytochrome C does not inhibit the growth. At 50 μg/ml, the peptide most effective on HT29 cells is peptide 1047; peptides HBP3 and HBP6 give intermediate values, while peptide HBP7 is not very active at this concentration.

Example 27

Transporting Anti-Tumor and Anti-Inflammatory Substances Using the Peptides in the Invention.

Transporting an Aspirin Derivative.

Analgesics like aspirin, long used in therapy, have been shown to have other effects, for example, the prevention of tumors of the colon in men and women who take aspirin regularly over a long period of time. In animals, the anti-cancer effect has been shown on various tumors. These effects have been partly attributed to their ability to inhibit the production of prostaglandins, by inhibiting the enzyme prostaglandin H synthetase and the cyclooxygenases.

Two aspirin derivatives conjugated to the peptide in sequence SEQ ID NO: 30: a salicylyl-HBP6 in -N terminal derivative (peptide SEQ ID NO: 47) and an HBP6-salicylyl in −C terminal derivative (SEQ ID NO: 48) have been tested for their ability to inhibit the growth of HT29 tumor cells in comparison with the natural peptide.

HT29 cells ($3\times10^4$ cells/well) are cultured in 96-well plates for 48 hours at 37° C. in the complete culture medium DMEM with decreasing concentrations of aspirin or peptide-salicylyl conjugate added, and the culture continued for 48 hours.

The wells are then filled with 50 μl of MTT (3-,(4,5-dimethylthiazol-2yl)-2,5-diphenyl tetrazolium bromide) at 1 mg/ml in the culture medium and cultured for 4 hours. The supernatant is removed, and 100 μl of dimethylsulfoxide is added to the wells. After the crystals dissolve, the coloration is read at 550 nm.

The results inhibiting the growth of HT29 cells are shown in Table 26 and are calculated as a percentage of the mean optical density obtained in the wells of cells containing the dilutions of the samples being tested and the optical density of the wells that received only medium.

TABLE 26

|  | Concentration (μg/ml) | | | |
|---|---|---|---|---|
|  | 1000 | 500 | 200 | 100 |
| Natural aspirin | 48* | 6 | 3 | 0 |
| Salicylyl-HBP6 | 51 | 35 | 30 | 30 |
| HBP6-salicylyl | 50 | 45 | 20 | 20 |

*% inhibition

The addition of the peptide to the salicylic acid increases the aspirin's power to inhibit the growth of the cells.

Transporting a Phthalic Acid Derivative

N-phthalimidoglutarimide (thalidomide) is a molecule that has a great variety of properties, such as a teratogenic effect, reduction of the production of TNF-α by the monocytes and suppression of angiogenesis. It has been shown that the teratogenic activity depends on the glutarimide residue, while the antiangiogenic effect depends on the phthaloyl group. We therefore prepared peptide SEQ ID NO: 46 derived from peptide SEQ ID NO: 26 (HBP3)$_2$ and added glycyl phthaloyl in N-terminal. The technique used to test the activity of phthaloyl-HBP3 is the same as the one previously described for aspirin.

The results of the inhibition of the growth (%) of HT29 cells shown in Table 27 are calculated as a percentage of the mean optical density in the wells of cells containing dilutions of the samples being tested and the mean optical density of the wells of cells that received only medium.

TABLE 27

| | Concentration (µg/ml) | | | |
|---|---|---|---|---|
| | 1000 | 500 | 200 | 100 |
| Phthaloyl-HBP3 | 66 | 28 | 29 | 20 |
| HBP3 | 2 | 0 | 0 | |

*%

It appears that the phthaloyl derivative inhibits the growth of HT29 cells.

Example 28

Increasing the Activity of Anti-Microbial Substances Using the Peptides of the Invention Lysozyme Lysozyme is one of the major constituents of granules of human polynuclear lymphocytes. It is also found in secretions. It is a muraminidase. Lysozyme lyses and kills gram-positive microorganisms by modifying the peptidoglycans on their surface. As lysozyme does not easily penetrate the outer membrane of the bacteria, coupling lysozyme to peptides can help with their penetration.

Coupling Peptides to Lysozyme 8 mg of lysozyme in 2.7 ml of sodium phosphate buffer 0.1M, pH7 containing 0.15M NaCl is added to 1.8 mg of SMCC (succinimidyl 4-(N-maleimidomethyl cyclohexane-1-carboxylate) in 186 µl dimethylsulfoxide, and the solution is incubated 30 minutes at laboratory temperature. The excess reagent is eliminated by centrifugation on ultrafiltration membranes (cutoff threshold=5,000 Daltons, Sartorius), followed by three washings in sodium phosphate buffer 0.1M, pH 7 containing 0.15M NaCl.

The peptide is then coupled in a molar ratio of 5 peptides to 1 lysozyme in 1 ml of sodium phosphate buffer 0.1M, pH7 containing 0.15M NaCl, for 3 hours at laboratory temperature. Then, the excess uncoupled peptide is eliminated by centrifugation on membranes, as in the preceding step.

Evaluating the Activity of Lysozyme Coupled to Peptides.

The gram-positive bacterial strain Escherischia coli (ATCC25922) is cultured until the semi-logarithmic phase in Luria-Bertani (LB) medium. The bacteria are collected by centrifugation and resuspended in 1% bacto-peptone medium at a concentration of $5 \times 10^5$ cfu/ml (colony forming unit/ml). Lysozyme or the peptide-lysozyme conjugates are diluted half and half (256 to 0.5 µg/ml) in bacto-peptone medium, and 50 µl is distributed in 96-well plates. 50 µl of the bacterial dilution is then added to each well. After 16 hours of incubation at 37° C., 10 µl from each well is smeared on gelose plates in LB medium. After 18 hours of incubation at 37° C., the minimal bactericide concentration (MBC) is determined as the concentration of lysozyme or lysozyme-peptide that inhibits 75% of the growth.

Results

Table 28 reports the inhibition of the growth of E. coli (MBC µg/ml).

TABLE 28

| Natural lysozyme | >256 |
|---|---|
| 1047-lysozyme | 32 |
| (HBP1)$_3$-lysozyme | 4 |
| (HBP3)$_2$-lysozyme | 16 |
| HBP6-lysozyme | 16 |

The peptide-lysozyme conjugates have an antibacterial activity more effective than that of the natural lysozyme.

Antimicrobial Peptides

For several years, there has been considerable interest in studying the structure-function of short peptides having antibacterial and antifungal activities. Many natural peptides with varied sequences found in the animal and vegetable world have similar modes of action against a wide variety of microbes.

The antimicrobial peptides generally have an equivalent number of polar and non-polar residues within amphipathic areas and enough basic residues to give a peptide with an overall positive charge at neutral pH.

The peptides that are the subject of this invention are also mainly alkaline peptides, with a high affinity for heparin, and in the examples given below, it is shown that several of them have antibacterial activity in vitro at concentrations at which they are not toxic to eukaryotic cells.

Evaluating the Antibacterial Activity of Cationic Peptides

The gram-positive bacterial strains are: Enterococcus faecalis (ATCC 29212), and Staphylococcus aureus (ATCC 25923) and the gram-negative strains are: Escherichia coli (ATCC 25922), Pseudomonas aeruginosa (ATCC 27853) and Salmonella typhimurim (clinical isolate), Salmonella typhiTy2 (WHO). The bacteria are cultured with shaking all night at 37° C., then recultured at a dilution of 1:50 in some fresh Luria-Bertani (LB) medium for 2 hours. The bacterial concentration is adjusted to 106 cfu/ml, and 50 µl is distributed in 96-well plates with an equal volume of peptides diluted half and half (256-0.5 µg/ml) in LB medium. After 16 hours at 37° C., the minimum inhibiting concentration (MIC) is determined as the smallest concentration that totally inhibits the growth of the bacteria (total absence of turbidity). To determine the minimum bactericide concentration, 10 µl from each well is spread on gelose plates in LB medium. After 18 hours of incubation at 37° C., the minimum bactericide concentration (MBC) is defined as the peptide concentration that allows only 0.01% of live bacteria to subsist.

Results.

The results are expressed as the peptide concentration in MBC (µM).

TABLE 29

| Peptide strains | E. coli | S. typhimurium | S. typhi-Ty2 | P. aeruginosa | S. aureus | E. faecalis |
|---|---|---|---|---|---|---|
| SEQ ID NO: 2 | >160* | >160 | nt | >160 | >160 | >160 |
| SEQ ID NO: 3 | 13.25 | 13.25 | 1.65 | 26.5 | >106 | >106 |
| SEQ ID NO: 38 | >170 | >170 | >170 | >170 | >170 | >170 |

TABLE 29-continued

| Peptide strains | E. coli | S. typhimurium | S. typhi-Ty2 | P. aeruginosa | S. aureus | E. faecalis |
|---|---|---|---|---|---|---|
| SEQ ID NO: 24 | 55 | 110 | 27.5 | 27.5 | >110 | >110 |
| SEQ ID NO: 44 | 1.7 | 1.27 | 0.64 | >110 | >110 | >110 |
| SEQ ID NO: 45 | 1 | 1 | 0.66 | 0.5 | >680 | >680 |
| Ampicillin | 22 | 11 | 5.5 | >696 | <0.68 | 2.75 |

*µM

The results in the above table show that peptide $(HBP1)_3$ has bactericide activity, while peptides $(HBP1)_2$ and HBP13 are not active. However, when peptide HPB13 (SEQ ID NO: 38) is coupled with peptide SEQ ID NO: 24, it enhances its activity by a factor of 50 to 100 (peptide SEQ ID NO: 45). The same is true when peptide SEQ ID NO: 24 is coupled with peptide SEQ ID NO: 30 (HPB7) which itself has no anti-microbial activity. The minimum bactericide concentration (MBC) of all the peptides in the above table is equivalent to the MIC or differs by a dilution (MBC=2×MIC). None these peptides are active on gram-positive bacteria.

Example 29

Integrity of the Caco-2 Barrier Model

Caco-2 cells were seeded at a density of 160000 cells/cm$^2$ on a polyethylene terephtalate microporous membranes, previously coated with bovine dermal collagen, in a synthetic serum-free medium (Basal Defined Medium, BDM). Culture medium was changed three times a week and cells were maintained at 37° C. in a an atmosphere of 5% $CO_2$ for 18 days. As a negative control to check the integrity of the Caco-2 barrier, $10^6$ dpm/ml D-[$^{14}$C]-mannitol was used. As a positive control, L-[$^3$H]-proline was used: active transport- $10^6$ dpm/ml, 10 µM as final concentration. Other controls included D-[$^{14}$C]-mannitol/L-[$^3$H]-Proline+HBP7 30 µg/ml and D-[$^{14}$C]-mannitol/L-[$^3$H]-proline+HBP10 30 µg/ml.

Trans-epithelial transport experiments were carried out. The trans-epithelial electrical resistance (TEER) was measured to check the integrity of the Caco-2 cell monolayers. The cell monolayers were preincubated in Hanks' balanced salt solution (HBSS, 5 mM glucose, supplemented with 10 mM Hepes) for 8 hours at 37° C. At 1, 2, 4 and 8 hours, 100 µl of medium was collected from the lower compartment and replaced by fresh HBSS. At the end of the experiment (8 hours), the cell monolayers were washed three times with PBS and TEER was measured. The cells were then collected in 400 µl of Tris-HCl 0.1 M pH 8.0, 0.5 % Triton X100 and disrupted by ultrasonication. The radioactivity contained in 100 µl of cell homogenate was measured. The amount of radioactive material was analyzed by liquid scintillation spectrometry using a Packard Tri-carb 1600CA instrument (Packard Instrument company, Meriden, Conn., USA) after light dispersion in 2 ml of Aqualuma coktail (Lumac/3M bv, Schaesberg, the Netherlands).

Figure 21:
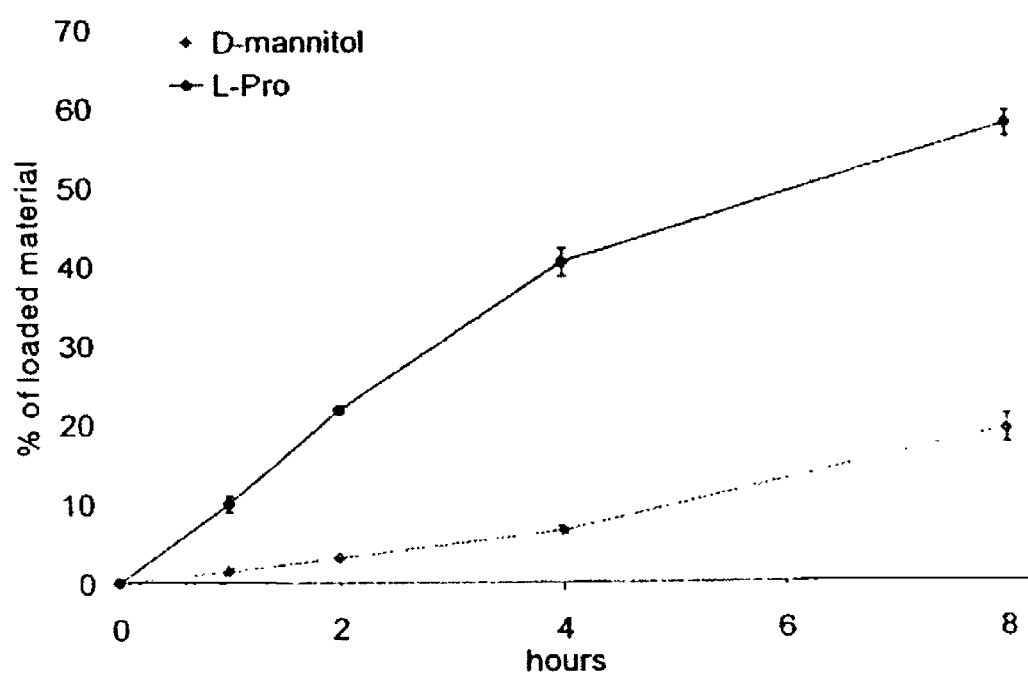
FIG. 21 is a line graph showing kinetics of the transport of D-[$^{14}$C]-mannitol and L-[$^3$H]proline.

FIG. 21 shows the transport of D-[$^{14}$C]-mannitol and L-[$^3$H]-proline. The results indicate that the trans-epithelial transport of D-[$^{14}$C]-mannitol and L-[$^3$H]-proline is proportional to the duration of the experiment during the first 4 hours. The transport of L-[$^3$H]-proline (positive control) was higher than that of D-[$^{14}$C]-mannitol (negative control), indicating that the Caco-2 intestinal barrier model could be used to estimate the transport of the HBP-insulin compounds.

Between 4 and 8 hours of incubation, the transport of L-[$^3$H]-proline slowed down and the transport of D-[$^{14}$C]-mannitol significantly increased. This observation resulted from an alteration of the cell monolayers by the long incubation in HBSS. A drastic decrease in TEER values measured at the end of the transport experiment (after 8 hours of incubation in HBSS) is in correlation with these observations (Table 30).

Figure 22:
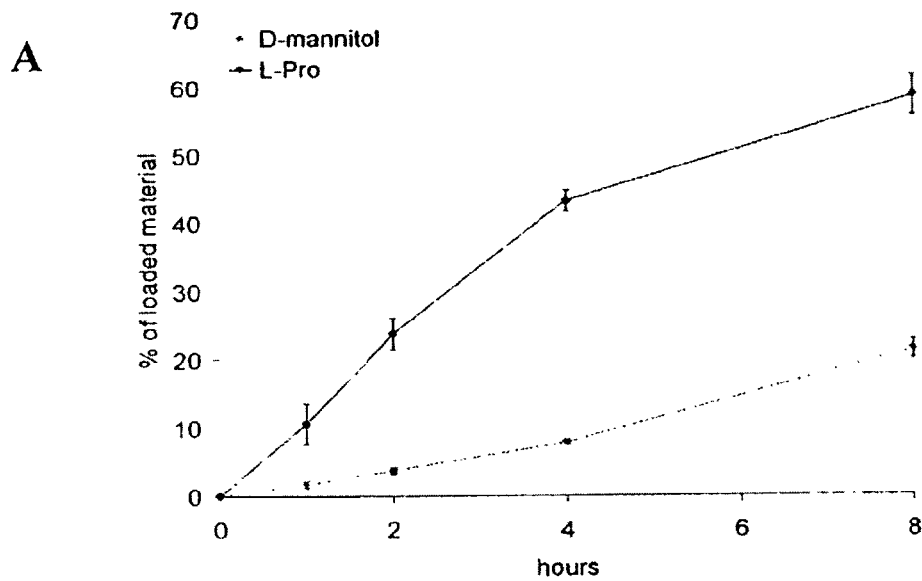
FIG. 22 is a line graph showing kinetics of the transport of D-[$^{14}$C]-mannitol and L-[$^3$H]pr in the presence of 30 μg/ml of DVP7-insulin (A) or DPV10-insulin (B).
Figure 22:
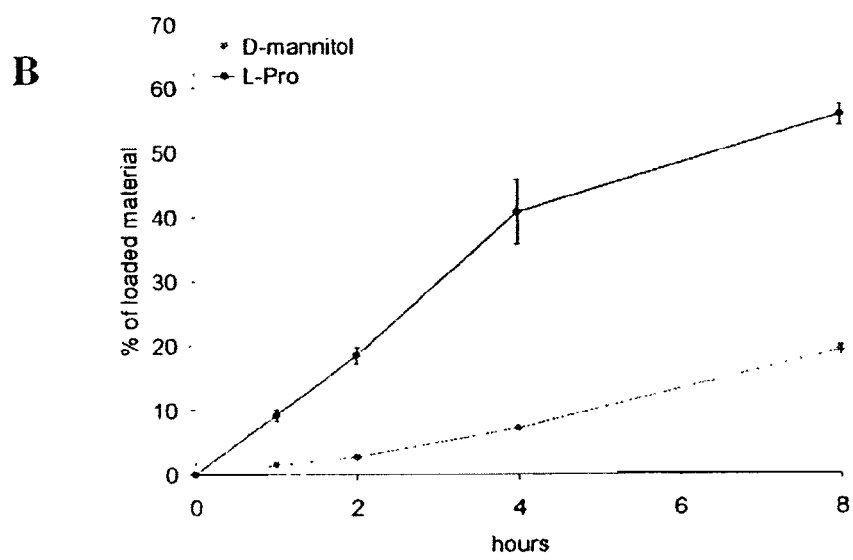
Figure 23:
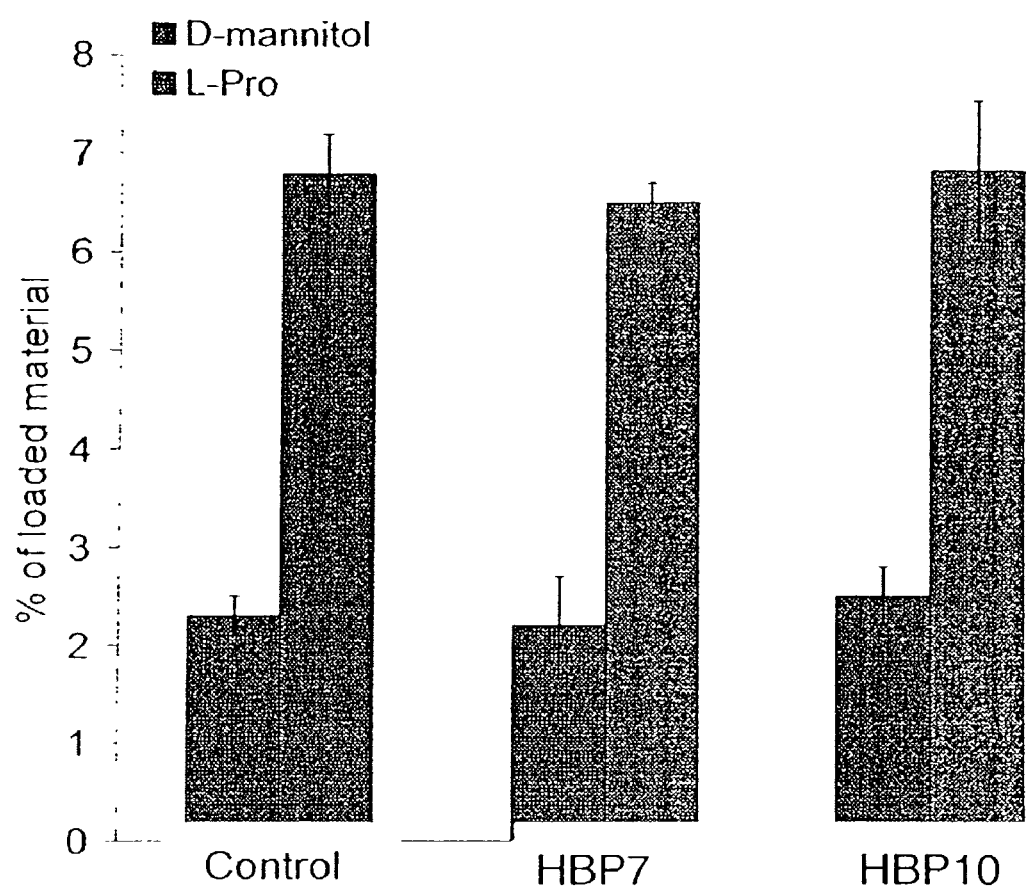
FIG. 23 is a bar graph showing D-[$^{14}$C]-mannitol and L-[$^3$H]proline associated with the cells at 8 hours post-incubation when they were incubated alone (control) or in the presence of 30 μg/ml of DVP7 or DVP10.

The presence of 30 µg/ml of HBP7 or HBP10 did not affect the transport of D-[$^{14}$C]-mannitol or L-[$^3$H]-proline (FIG. 22), nor the amounts of D-[$^{14}$C]-mannitol and L-[$^3$H]-proline associated with the cells at the end of the experiment (FIG. 23).

TABLE 30

TEER Measurements

| | Insert n° | TEER before incubation ($\Omega \cdot cm^2$) | TEER after incubation ($\Omega \cdot cm^2$) |
|---|---|---|---|
| Control | 1 | 540 | 143 |
| | 2 | 495 | 173 |
| | 3 | 512 | 124 |
| HBP7 | 1 | 506 | 117 |
| | 2 | 828 | 145 |
| | 3 | 545 | 129 |
| HBP10 | 1 | 500 | 153 |
| | 2 | 458 | 201 |
| | 3 | 501 | 201 |

Example 30

Insulin and HBP-Insulin Conjugates Trans-Epithelial Transport

HBP-insulin conjugates were synthesized. Briefly, insulin was activated by a 10 molar excess of a hetero-bifunctionnal cross-linking agent, SMCC. After several washing steps, HBP7 or HBP10 was added in a 5 fold molar excess. The samples were washed again to eliminate uncoupled materials, and the conjugates were checked by SDS-Page electrophoresis analysis. Insulin, HBP7-insulin, and HBP10-insulin were diluted in NaCl 0.15 M to obtain a final concentration of 0.65 mg/ml. 30 µg of each molecule was incubated on the Caco-2 cell monolayers.

Trans-epithelial transport experiments were carried out. The trans-epithelial electrical resistance (TEER) was measured to check the integrity of the Caco-2 cell monolayers. The cell monolayers were preincubated in Hanks' balanced salt solution (HBSS, 5 mM glucose, supplemented with 10 mM Hepes) for 30 minutes at 37° C. The insulin compounds were added at a concentration of 60 µg/ml in 0.5 ml of HBSS medium in the upper compartment of the insert, facing the apical side of the cells. The upper and lower compartmrent contained 0.5 and 1.25 ml of HBSS respectively. The cell monolayers were incubated at 37° C. for 1, 4 or 8 hours with insulin compounds. The media of the upper and lower compartments were collected. The cell monolayers were washed three times with PBS and TEER was measured. The cells were collected in 400 µl of Tris-HCl 0.1 M pH 8.0, 0.5% Triton X100. For each condition, three inserts were used (triplicates).

Table 31 shows the values of TEER measured before and after incubation with the compounds. The results indicate that HBP7-insulin induced a significant decrease in TEER after 1 and 4 hours of incubation, indicating that the integrity of the Caco-2 cell monolayer was affected by HBP7-insulin at these two time points. This TEER breakdown and this change in the cell morphology were not observed for insulin and HBP10-insulin. The results also showed a significant decrease in TEER after 8 h of incubation with the three compounds. This is in agreement with the results from Example 25, indicating that a time of incubation in HBSS longer than 4 hours alters the Caco-2 cell barrier.

TABLE 31

TEER Measurements

|  | Insert n° | TEER before incubation ($\Omega \cdot cm^2$) | TEER after transport ($\Omega \cdot cm^2$) |
|---|---|---|---|
| Insulin 1 h | 1 | 458 | 478 |
|  | 2 | 592 | 561 |
|  | 3 | 445 | 425 |
| Insulin 4 h | 1 | 510 | 305 |
|  | 2 | 451 | 324 |
|  | 3 | 606 | 325 |
| Insulin 8 h | 1 | 442 | 151 |
|  | 2 | 451 | 145 |
|  | 3 | 498 | 151 |
| HBP7-insulin 1 h | 1 | 515 | 143 |
|  | 2 | 434 | 202 |
|  | 3 | 542 | 178 |
| HBP7-insulin 4 h | 1 | 639 | 129 |
|  | 2 | 548 | 112 |
|  | 3 | 600 | 116 |
| HBP7-insulin 8 h | 1 | 543 | 123 |
|  | 2 | 583 | 95 |
|  | 3 | 473 | 112 |
| HBP10-insulin 1 h | 1 | 553 | 537 |
|  | 2 | 656 | 660 |
|  | 3 | 599 | 573 |
| HBP10-insulin 4 h | 1 | 678 | 553 |
|  | 2 | 451 | 386 |
|  | 3 | 498 | 416 |
| HBP10-insulin 8 h | 1 | 650 | 194 |
|  | 2 | 613 | 190 |
|  | 3 | 605 | 186 |

Example 31

Detection and Quantification of Insulin Compounds

Free insulin concentrations were measured with an ELISA kit from Dako (ref. K6219). HBP-insulin conjugates were detected by a self-manufactured assay. Briefly, HBP-insulin conjugates were absorbed on heparin-coated wells in 96-well microtiter plates. The levels of HBP-insulin conjugates were quantified by an ELISA-derived assay using a mouse anti-insulin monoclonal antibody and a peroxydase-coupled secondary antibody.

Figure 24:
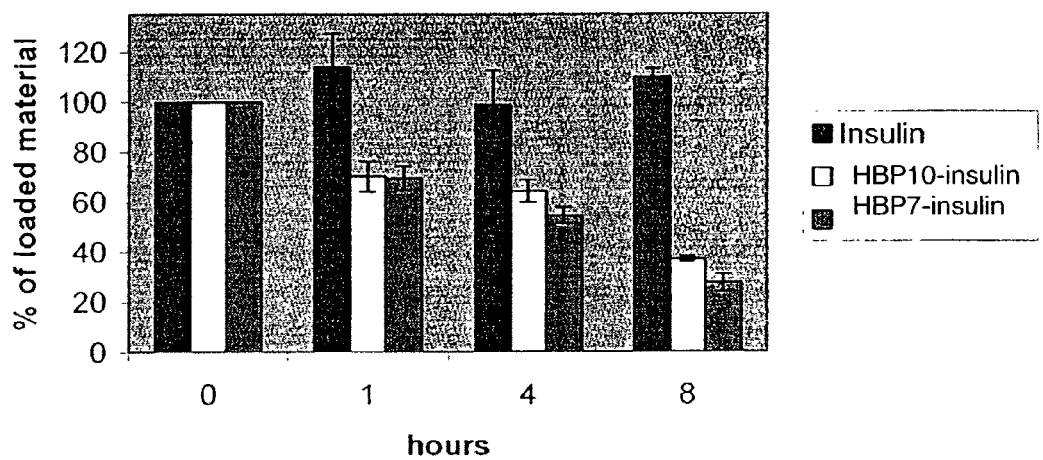
FIG. 24 is a bar graph showing levels of insulin and DPV-insulin conjugates in the apical medium.

The samples colected after incubation with the Caco-2 cells were transferred in BSA coated microtubes and at −20° C. until insulin levels were measured. Free insulin levels stayed stable in the apical medium during the whole experiment. In contrast, the apical concentration of HBP-insulin conjugates decreased as a function of the time. At 8 hours, the levels of HBP7-insulin and HBP10-insulin corresponded to 25% and 35% respectively of the initial loading (FIG. 24). Significant decreases in HBP-insulin conjugate levels were also observed at 1 and 4 hours (FIG. 24). At these two time points, the levels of HBP-insulin conjugates were 70% of the initial loading at 1 hour for both conjugates. 54% and 64% of the initial loading at 4 hours, for HBP7-insulin and HBP10-insulin respectively.

A small quantity of free insulin was detected in the basolateral medium, (0.2% of the loaded material). No significant amounts of HBP-insulin conjugates were detected in the basolateral medium, possibly because the assay for the detection of HBP-insulin conjugates is 1000 fold less sensitive than the Dako assay for the detection of free insulin. Taking this difference of sensitivity into account, it would have been unlikely to detect such a small quantity of HBP-insulin conjugate.

Figure 25:
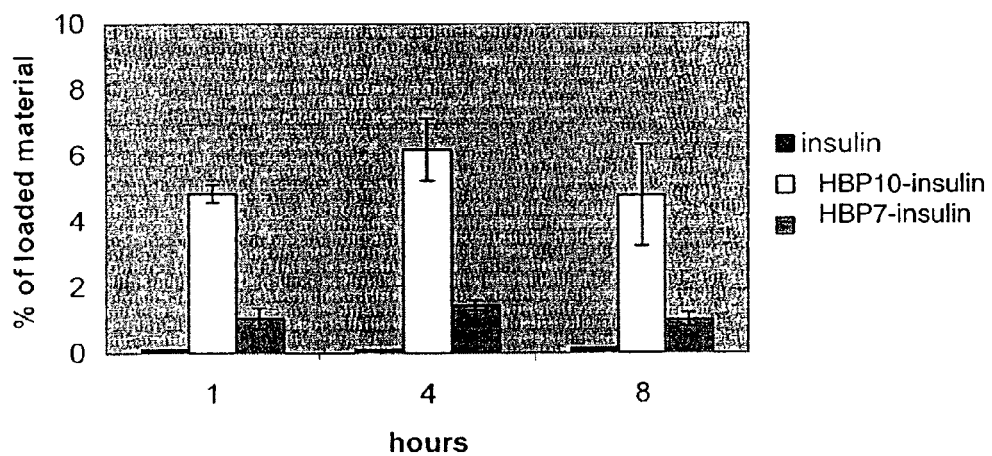
FIG. 25 is a bar graph showing levels of DPV-insulin conjugates in the cell lysates as a function of time.

A very small quantity of free insulin was found in the cell lysate, (approximately 0.004% of the initial loading). In contrast, the quantity of HBP7-insulin and HBP10-insulin detected in the cell lysate after one hour of transport reached 1% and 4% of the initial loading, respectively (FIG. 25). These levels were stable throughout the experiment, suggesting that the compounds did not accumulate intracellularly, and could exit the Caco-2 cells.

The filters on which Caco-2 cells were grown were also analysed for the presence of insulin and HBP-insulin conjugates. Free and HBP-insulin conjugates were detected on the filters using the same quantitation assay, allowing a direct comparison of the quantities of compounds that remained on the filters.

Results indicated that only a small amount of free insulin was remaining on the filters. In contrast, when coupled to HBP10 or HBP7, insulin conjugates clearly stayed trapped on the cell culture inserts.

Example 32

In Vitro Quantification of HBP-Insulin Conjugates

HBP-insulin conjugates were synthesized as described in Example 30. In order to validate the measurement of conjugate concentration, several tests are performed. Recognition of insulin-HBP conjugates is verified using an RIA test. A standard concentration curve is established in vitro for each conjugate, in parallel with free insulin, so as to make sure that the conjugates are recognized by the anti-insulin antibody as well as to determine whether the conjugates can be quantified with a correct sensibility using the RIA test.

Example 33

In Vivo Quantification of HBP-Insulin Conjugates

HBP-insulin conjugates were synthesized as described in Example 30. The activity of HBP-insulin conjugates are assessed in vivo, after a subcutaneous injection of appropriate levels of conjugates in hyperglycemic rats. Controls are injected with either free insulin or NaCl. Blood samples are collected at predetermined time points and analyzed for both insulin and glucose concentrations, using an ELISA and glucose oxidase method, respectively. An increase in blood insulin concentration and a subsequent decrease in blood glucose levels indicates that the HBP-insulin conjugates are biologically active.

Example 34

In Vivo Evaluation of HBP-Insulin Conjugates After Oral Administration

In order to assess the passage of the intestinal barrier by the HBP-insulin conjugates, compounds are inserted into the ileal lumen of hyperglycemic rats. Controls are administered with either free insulin or NaCl, before evaluation of the passage of insulin in the blood of the treated rats.

Glycemia is controlled for all animals every 15 minutes for at least three hours following administration, then every hour for the following 12 hours. Blood samples are collected at predetermined time points and analyzed for glucose concentrations using a glucose oxidase method. A decrease in blood glucose levels indicates the passage of insulin through the intestinal barrier.

For those animals in which the in vivo tests indicate no biological activity of insulin however, in vitro quantification was possible using the RIA test, blood is taken at one time point after the subcutaneous injection and the level of insulin conjugate is determined by RIA in each blood sample. This direct detection of the insulin allows for the determination whether the conjugate has crossed the intestinal barrier.

Example 35

Morphological and Immunocytochemical Studies

Small intestinal ileal tissue of the hyperglycemic rats contacted with the HBP-insulin conjugates is collected in order to verify the integrity of the tight junctions. An immunocytochemical study is performed after a single time point (30 or 60 minutes) to demonstrate transcellular transport of insulin.

What is claimed:

1. A peptide comprising the amino acid sequence of SEQ ID NO:10 coupled to a substance of interest selected from the group consisting of a toxin, an antibiotic, an antiviral compound, a nucleic acid molecule, a plasmid, an enzyme, an antibody, and a fragment of an antibody, and wherein the peptide translocates via receptor mediation across a cell membrane that is a phospholipid bilayer.

2. The peptide of claim 1, wherein the substance of interest is doxorubicin.

3. A composition comprising SEQ ID NO:10 and a pharmaceutically acceptable carrier.

4. A kit comprising in one or more containers the composition of claim 3.

* * * * *